US012594281B2

(12) United States Patent
Wanaski et al.

(10) Patent No.: US 12,594,281 B2
(45) Date of Patent: Apr. 7, 2026

(54) PHARMACEUTICAL DOSAGE FORMS AND METHODS OF USE

(71) Applicant: EMALEX BIOSCIENCES, INC., Chicago, IL (US)

(72) Inventors: Stephen P. Wanaski, Chicago, IL (US); Virginia D. Schmith, Cocoa Beach, FL (US); Jay A. White, Newmarket (CA); Timothy M. Cunniff, Chicago, IL (US)

(73) Assignee: EMALEX BIOSCIENCES, INC., Chicago, IL (US)

( * ) Notice: Subject to any disclaimer, the term of this patent is extended or adjusted under 35 U.S.C. 154(b) by 0 days.

(21) Appl. No.: 19/210,898

(22) Filed: May 16, 2025

(65) Prior Publication Data

US 2025/0288594 A1 Sep. 18, 2025

Related U.S. Application Data

(63) Continuation of application No. PCT/US2025/020111, filed on Mar. 14, 2025.

(60) Provisional application No. 63/565,834, filed on Mar. 15, 2024.

(51) Int. Cl.

*A61K 31/55* (2006.01)
*A61K 9/00* (2006.01)
*A61K 9/20* (2006.01)
*A61P 25/14* (2006.01)

(52) U.S. Cl.

CPC .............. *A61K 31/55* (2013.01); *A61K 9/006* (2013.01); *A61K 9/2018* (2013.01); *A61P 25/14* (2018.01)

(58) Field of Classification Search

CPC ....... A61K 31/55; A61K 9/006; A61K 9/2018
See application file for complete search history.

(56) References Cited

U.S. PATENT DOCUMENTS

| | | | |
|---|---|---|---|
| 4,477,378 | A | 10/1984 | Gold et al. |
| 4,973,586 | A | 11/1990 | Berger et al. |
| 5,302,716 | A | 4/1994 | Berger et al. |
| 5,607,967 | A | 3/1997 | Friedman et al. |
| 6,132,724 | A | 10/2000 | Blum |
| 7,202,233 | B2 | 4/2007 | Penkler |
| 9,949,983 | B2 | 4/2018 | Chipkin |
| 10,751,327 | B2 | 8/2020 | Clemens et al. |
| 11,298,361 | B2 | 4/2022 | Chipkin et al. |
| 12,161,755 | B2 | 12/2024 | Bushara |
| 12,220,404 | B2 | 2/2025 | Clemens et al. |
| 2003/0109532 | A1 | 6/2003 | Sonesson et al. |
| 2004/0122065 | A1 | 6/2004 | Lerner et al. |
| 2007/0202057 | A1 | 8/2007 | Fankhauser et al. |
| 2009/0042956 | A1 | 2/2009 | Bozik et al. |
| 2009/0156581 | A1 | 6/2009 | Dillon et al. |
| 2010/0168085 | A1 | 7/2010 | Eisenbach-Schwartz et al. |
| 2010/0255086 | A1 | 10/2010 | Ovil |
| 2010/0273767 | A1 | 10/2010 | Wang et al. |
| 2011/0206782 | A1 | 8/2011 | Zhang |
| 2011/0262442 | A1 | 10/2011 | Hamilton et al. |
| 2018/0110738 | A1 | 4/2018 | Zerbe et al. |
| 2021/0275540 | A1 | 9/2021 | Chipkin et al. |
| 2022/0290159 | A1 | 9/2022 | Zakharenko et al. |
| 2024/0189331 | A1 | 6/2024 | Bilal et al. |

FOREIGN PATENT DOCUMENTS

| | | | |
|---|---|---|---|
| CA | 2465869 | A1 | 5/2003 |
| EP | 0351733 | B1 | 12/1995 |
| EP | 2872145 | B1 | 3/2022 |
| JP | 10-509139 | A | 9/1998 |
| WO | 93/01702 | A1 | 1/1993 |
| WO | 93/13073 | A1 | 7/1993 |
| WO | 95/25102 | A1 | 9/1995 |
| WO | 96/13257 | A1 | 5/1996 |
| WO | 99/21540 | A2 | 5/1999 |
| WO | 2002/100350 | A2 | 12/2002 |
| WO | 03/39468 | A2 | 5/2003 |
| WO | 2011/057199 | A1 | 5/2011 |
| WO | 2012/039660 | A1 | 3/2012 |
| WO | WO-2012/033874 | A1 | 3/2012 |
| WO | WO-2014/012063 | A1 | 1/2014 |
| WO | WO-2024/074986 | A1 | 4/2024 |
| WO | WO-2024/102381 | A1 | 5/2024 |

OTHER PUBLICATIONS

Salehi, "Improving Dissolution Behavior and Oral Absorption of Drugs with pH-Dependent Solubility Using pH Modifiers: A Physiologically Realistic Mass Transport Analysis", Mol. Pharmaceutics 2021, 18, 3326-3341.*

Aldawsari et al., "Enhanced pharmacokinetic performance of dapoxetine hydrochloride via the formulation of instantly-dissolving buccal films with acidic pH modifier and hydrophilic cyclodextrin: Factorial analysis, in vitro and in vivo assessment," Journal of Advanced Research, 24:281-290 (2020).

Clinical Trails—NCT01408394, "Safety and Tolerability Comparison of Immediate and Controlled Release Formulations of Ecopipam," 10 pages (2024).

Clinical Trials—NCT04902105, "Drug-Drug Interaction Study to Evaluate the Effect of Inhibition of UGTs on the PK of Ecopipam and Its Active Metabolite," 21 pages (2021).

Clinical Trials—NCT05841160, "Thorough QT/QTc Study to Evaluate the Effects of Ecopipam (EBS-101) on Cardiac Repolarization," 27 pages, (2023).

Gilbert et al., "A D1 Receptor Antagonist, Ecopipam, for Treatment of Tics in Tourette Syndrome," Clinical Neuropharmacology, 37(1):26-30 (2014).

(Continued)

*Primary Examiner* — Sahar Javanmard

(74) *Attorney, Agent, or Firm* — MARSHALL, GERSTEIN & BORUN LLP

(57) ABSTRACT

Pharmaceutical dosage forms of D1/D5 receptor antagonists, and related methods of their use, are disclosed.

30 Claims, 7 Drawing Sheets

(56) References Cited

OTHER PUBLICATIONS

Gilbert et al., "Ecopipam for Tourette Syndrome: A Randomized Trial," Pediatrics, 151(2):10 pages (2023).
He et al., "Microenvironmental pH Modification in Buccal/ Sublingual Dosage Forms for Systemic Drug Delivery," Pharmaceutics 15:637, 18 pages (2023).
Maguire et al., "Ecopipam as a pharmacologic treatment of stuttering," Annals of Clinical Psychiatry, 31(3):164-168 (2019).
Ondo et al., "Exploratory cross-over, trial of augmented RLS with the dopamine receptor 1/5 antagonist ecopipam D1/D5 antagonist ecopipam for augmented RLS," International Journal of Neuroscience, 132(8):778-782 (2022).
Qiang et al., "Discovery of new SCH 39166 analogs as potent and selective dopamine D1 receptor antagonists," Bioorganic & Medicinal Chemistry Letters, 20:836-840 (2010).
Sabra et al., "Buccal Absorption of Biopharmaceutics Classification System III Drugs: Formulation Approaches and Mechanistic Insights," Pharmaceutics, 16:1563, 15 pages (2024).
Schmith et al., "The Effect of UGT Inhibition on the Pharm Aco Kin-Etics of Ecopipam and Its Metabolites," Dialog, Supplement 1, 113, S71 (2023).
Study Details—NCT06194864, "Drug Interaction Study", 20 pages (2024).
Tephly et al., "Studies on the Glucuronidation of Dopamine D-1 Receptor Antagonists, SCH 39166 and SCH 23390, by Human Liver Microsomes," Drug Metabolism and Disposition, 22(5):713-718 (1994).
Wanaski et al., "The Effect of Ecopipam and its Metabolites on Cardiac Repolarization, QTcF (P10-5.014)", Neurology, 104, 3 pages (2025).
International Search Report and Written Opinion from International Application No. PCT/US2025/020111 dated Jun. 26, 2025.
Smith, "American Society for Clinical Pharmacology and Therapeutics", Clinical Pharmacology and Therapeutics, 113(S1), pp. 1-96 (2023).
"Acute Oral and Intraperitoneal Toxicity Studies of SCH 39166 (HCl) in Mice", Report No. P-5326, Study No. 88089, 88090 (Oct. 24, 1988).
"Acute Oral and Intraperitoneal Toxicity Studies of SCH 39166 (HCl) in Rats", Report No. P-5325, Study No. 88087, 88088 (Oct. 24, 1988).
"Examination Report corresponding to European Application No. 16837850.3 dated Apr. 6, 2021".
"Summons to attend oral proceedings corresponding to European Application No. 16837850.3 dated Sep. 2, 2022".
Allen et al. "A randomized, double-blind, 6-week, dose-ranging study of pregabalin in patients with restless legs syndrome" Sleep Medicine, 11(6):512-519 (2010) (Abstract only).
Allen et al. "Augmentation of the restless legs syndrome with carbidopa/levodopa" Sleep, 19(3):205-213 (1996) (Abstract only).
Allen et al. "Restless legs syndrome/Willis-Ekbom disease diagnostic criteria: updated International Restless Legs Syndrome Study Group (IRLSSG) consensus criteria—history, rationale, description, and significance" Sleep Medicine, 15(8):860-873 (2014) (Abstract only).
Allouche et al. "Opioid receptor desensitization: mechanisms and its link to tolerance" Frontiers in Pharmacology 5(280):1-20 (2014).
Anonymous: "Clinical Trials Archive—History of Changes for Study: NCT0124463333", May 8, 2012 (May 8, 2012).
Anonymous: "Ecopipam tablets to Study Tourette's syndrome in children and adolescents (DIAMOND)", Apr. 21, 2022, pp. 1-21.
Arnt et al., The citalopram/5-HTP-induced head shake syndrome is correlated to 5-HT2 receptor affinity and also influenced by other transmitters., Acta Pharmacol Toxicol (Copenh), 55(5):363-372 (1984).
Ashurst, John et al., Developmental and Persistent Developmental Stuttering: An Overview For Primary Care Physicians, Journal of American Osteopathic Associations, 111, 576-580, 2011.
Astrup et al., "Randomized Controlled Trials of the D1/D5 Antagonist Ecopipam for Weight Loss in Obese Subjects," Obesity, 15(7):1717-1731 (2007).
Baier et al. "Circadian variation in restless legs syndrome" Sleep Medicine, 8(6):645-650 (2007) (Abstract only).
Barriere et al. "The restless legs syndrome" Progress in Neurobiology, 77(3):139-165 (2005) (Abstract only).
Bayard et al. "Decision-making, Reward-Seeking Behaviors and Dopamine Agonist Therapy in Restless Legs Syndrome" Sleep, 36(10):1501-1507 (2013).
Beaulieu and Gainetdinov, The Physiology, Signaling, and Pharmacology of Dopamine Receptors, Pharmacol Rev 63(1):182-217 (2011).
Bedard et al., The 'wet dog shake' behaviour in the rat and 5-hydroxytryptamine, Br J Pharmacol 59(3): 450P-451P (1977).
Bekhit, M.H. "Opioid-induced hyperalgesia and tolerance" American Journal of Therapeutics, 17(5):498-510 (2010) (Abstract only).
Berge, et al., Pharmaceutical Salts, Journal of Pharmaceutical Sciences 66(1): 1-19 (1977).
Blomgren, Michael, Behavioral Treatments For Children and Adults Who Stutter: a Review, Psychol. Res. Behav. Management, 6:9-19, 2013.
Bonnier et al., Ketanserin treatment of Tourette's Syndrome in children, American Journal of Psychiatry 156(7):1122a-1123 (1999).
Borowski et al., Blood Pressure Response to Thyrotropin-Releasing Hormone in Euthyroid Subjects, J Clin Endocrinol Metab 58(1):197-200 (1984).
Bothe, AK et al., Stuttering Treatment Research 1970-2005. I: Systematic Review Incorporating Trial Quality Assessment of Behavioral, Cognitive, and Related Approaches, American Journal of Speech-Language Pathology, 15:321-341, 2006.
Boyd, A et al., Pharmacological Agents for Developmental Stuttering in Children and Adolescents: A Systemic Review, J. Clin. Psychopharmacol., 31(6):740-744, 2011.
Braun, et al. "Selective D-1 dopamine receptor agonist effects in hyperkinetic extrapyramidal disorders," Journal of Neurology, Neurosurgery and Psychiatry (1989) vol. 52, pp. 631-635.
Breese et al. "Peripheral inflammation selectively increases TRPV1 function in 114-positive sensory neurons from adult mouse" Pain, 115(1-2):37-49 (2005) (Abstract only).
Brett et al., "The Genetic Susceptibility to Gilles de la Tourette Syndrome in a Large Multiple Affected British Kindred: Linkage Analysis Excludes a Role for the Genes Coding for Dopamine D1, D2, D3, D4, D5 Receptors, Dopamine Beta Hydroxylase, Tyrosinase, and Tyrosine Hydroxylase," Biol. Psychiatry, 37(8):533-540 (1995).
Brewer et al. "Dopamine D3 receptor dysfunction prevents anti-nociceptive effects of morphine in the spinal cord" Frontiers in Neural Circuits, 8:62-01-62-10 (2014).
Bubenikova-Valesova et al. "The effect of a full agonist/antagonist of the D1 receptor on locomotor activity, sensorimotor gating and cognitive function in dizocilpine-treated rats" International Journal of Neuropsychopharmacology, 12(7):873-883 (2009).
Buchel et al., What Causes Stuttering?, PLoS Biology, 2(2):159-163 (2004).
Castellano et al., Post-training dopamine receptor agonists and antagonists affect memory storage in mice irrespective of their selectivity for D1 or D2 receptors. Behav Neural Biol 56(3):283-91 (1991).
Cavanna et al., The Behavioral Spectrum of Gilles de la Tourette Syndrome, Journal of Neuropsychiatry and Clinical 'Jeurosciences 13-23 (2009).
Chahine et al. "Restless legs syndrome: a review" CNS Spectrums, 11(7):511-520 (2006) (Abstract only).
Chipkin et al., Pharmacological Profile of SCH39166: A Dopamine D1 Selective Benzonaphthazepine With Potential Antipsychotic Activity, Journal of Pharmacology and Experimental Therapeutics 247(3) : 1093-1102 (1988).
Cianchetti, C. et al. "Pergolide improvement in neuroleptic-resistant Tourette cases: various mechanisms causing tics," Neurol. Sci. (2005) vol. 26, No. 2, pp. 137-139.
Civelli et al., Molecular Diversity of the Dopamine Receptors, Annual Review of Pharmacology and Toxicology, 32:281-307 (1993).

(56) References Cited

OTHER PUBLICATIONS

Clemens et al. "Conversion of the Modulatory Actions of Dopamine on Spinal Reflexes from Depression to Facilitation in D3 Receptor Knock-Out Mice" The Journal of Neuroscience, 24(50):11337-11345 (2004).
Clemens et al. "Restless legs syndrome: revisiting the dopamine hypothesis from the spinal cord perspective" Neurology, 67(1):125-130 (2006).
Clemens et at. "Opposing modulatory effects of D1- and D2-like receptor activation on a spinal central pattern generator" Journal of Neurophysiology, 107(8):2250-2259 (2012).
ClinicalTrials.gov "Ecopipam Treatment of Tourette's Syndrome in Subjects 7-17 Years" https://clinicaltrials.gov/ct2/show/study/NCT02102698#wrapper (9 pages) (2014).
Communication pursuant to Article 94(3) EPC in European Application No. 13815988.4, dated Apr. 19, 2017, in 4 pages.
Communication pursuant to Article 94(3) EPC in European Application No. 13815988.4, dated Jun. 25, 2018.
Connor et al. "Postmortem and imaging based analyses reveal CNS decreased myelination in restless legs syndrome" Sleep Medicine, 12(6):614-619 (2011).
Corne et al., A Method for Assessing the Effects of Drugs on the Central Actions of 5-Hydroxytryptamine, Brit J Pharmacol 20: 106-120 (1963).
Costa, Daniel et al., Stuttering: an Update for Physicians, Canadian Medical Association Journal, 162:1849-1855, 2000.
Cote et al. "In vitro and in vivo characterization of the agonist-dependent D3 dopamine receptor tolerance property" Neuropharmacology, 79:359-367 (2014) (Abstract only).
Crosley, Decreased serotoninergic activity in Tourette syndrome, Ann. Neurol., 5(6):596-7 (Jun. 1979).
Cruz-Trujillo et al. "D3 dopamine receptors interact with dopamine D1 but not D4 receptors in the GABAergic terminals of the SNr of the rat" Neuropharmacology, 67:370-378 (2013) (Abstract only).
Darmopil et al. "Genetic inactivation of dopamine D1 but not D2 receptors inhibits L-DOPA-induced dyskinesia and histone activation" Biological Psychiatry, 66(6):603-613 (2009) (Abstract only).
Dauvilliers et al. "Restless legs syndrome: update on pathogenesis" Current Opinion in Pulmonary Medicine, 19(6):594-600 (2013) (Abstract only).
Davies S. "Rotigotine for restless legs syndrome" Drugs Today (Barc), 45(9):663-668 (2009) (Abstract only).
De Beaurepaire et al., "An Open Trial of the D1 Antagonist SCH 39166 in Six Cases of Acute Psychotic States," Psychopharmacology, 121:323-327 (1995).
Deandrade et al. "Motor restlessness, sleep disturbances, thermal sensory alterations and elevated serum iron levels in Btbd9 mutant mice" Human Molecular Genetics 21(18):3984-3992 (2012).
Den Boer et al., "Differential Effects of the D1-DA Receptor Antagonist SCH39166 on Positive and Negative Symptoms of Schizophrenia," Psychopharmacology, 121:317-322 (1995).
Diagnostic and Statistical Manual of Mental Disorders [DSM-IV-TR], Fourth Edition, American Psychiatric Association (2000). Table of Contents.
Dinkins et al. Long-term treatment with dopamine L3 receptor agonists induces a behavioral switch that can be rescued by blocking the dopamine D1, Sleep Medicine 40:47-52 (2017).
Djouhri et al. "Spontaneous pain, both neuropathic and inflammatory, is related to frequency of spontaneous firing in intact C-fiber nociceptors" The Journal of Neuroscience, 26(4):1281-1292 (2006).
Dougherty et al. "Properties of mouse spinal lamina I GABAergic interneurons" Journal of Neurophysiology, 94(5):3221-3227 (2005).
Drago et al. "Altered striatal function in a mutant mouse lacking D1A dopamine receptors" Proc Nat[ Acad Sci USA, 91(26):12564-12568 (1994).
Duffy et al., In vivo autoradiography of [3H]SCH 39166 in rat brain: selective displacement by D1/D5 antagonists, Journal of Chemical Neuroanatomy 19:41-46 (2000).
Dunlap, "TSA: Psyadon to collaborate on drug trial", https://xmssouiitsa.ors:/2011/05/12/lsa-psvadon-to-coliaboiBte-on-dmg-tfial/. May 12, 2011, Missouri.
Dursun, S.M. et al., "Similarities in the pharmacology of spontaneous and DOI-induced head-shakes suggest 5HT2A receptors are active under physiological conditions," Psychopharmacology (1996) vol. 128, No. 2, pp. 198-205.
Dziewczapolski et al. "Opposite roles of D1 and D5 dopamine receptors in locomotion revealed by selective antisense oligonucleotides" Neuroreport, 9(1):1-5 (1998) (Abstract only).
Earley et al. "Altered Brain iron homeostasis and dopaminergic function in Restless Legs Syndrome (Willis-Ekbom Disease)" Sleep Medicine, 15(11):1288-1301 (2014) (Abstract only).
Earley et al. "Increased synaptic dopamine in the putamen in restless legs syndrome" Sleep, 36(1):51-57 (2013).
Earley, C.J. "Latest guidelines and advances for treatment of restless legs syndrome" The Journal of Clinical Psychiatry, 75(4):e08 (2014) (Abstract only).
Ecopipam, Wikipedia, Apr. 26, 2013, Retrieved from the Internet: URL:https://en.wikipedia.org/wiki/Ecopipam, 4 Pages.
Emilien et al., Dopamine receptors—physiological understanding to therapeutic intervention potential, Pharmacology and Therapeutics 84:133-156 (1999).
England et al. "L-Dopa improves Restless Legs Syndrome and periodic limb movements in sleep but not Attention-Deficit-Hyperactivity Disorder in a double-blind trial in children" Sleep Medicine, 12(5):471-477 (2011).
Erman, M.K. "Selected sleep disorders: restless legs syndrome and periodic limb movement disorder, sleep apnea syndrome, and narcolepsy" The Psychiatric Clinics of North America, 29(4):947-967; abstract viii-ix (2006) (Abstract only).
European Patent Application No. 13815988.4, Communication Pursuant to Article 94(3) EPC, dated Jul. 11, 2019.
European Patent Application No. 13815988.4, Intention to Grant and related communication under Rule 71(3) EPC with text intended for grant, May 19, 2021.
European Patent Application No. 13815988.4, Summons to Attend Oral Proceedings Pursuant to Rule 115(1) EPC, Oct. 19, 2020.
European Search Report issued in connection with European Patent Application No. 14854586.6, dated Sep. 5, 2017, 10 pages.
Extended European Search Report corresponding to European Application No. 16837850.3 dated May 22, 2019.
Extended European Search Report for Application No. 13815988.4, dated Nov. 3, 2015.
Felling and Singer, Neurobiology of Tourette Syndrome: Current Status and Need for Further Investigation, Journal of Neuroscience 31(35):12387-12395 (2011).
Fenu et al., Differential involvement of dopamine D1 receptors in morphine- and lithium-conditioned saccharin avoidance Physiology & Behavior 96: 73-77 (2009).
Ferini-Strambi (Restless legs syndrome augmentation and pramipexole treatment, Sleep Medicine, vol. 3, Supplement, 2002, pp. S23-S25, ISSN 1389-9457).
Fiorentini et al. "Reciprocal regulation of dopamine D1 and D3 receptor function and trafficking by heterodimerization" Molecular Pharmacology, 74(1):59-69 (2008).
First Office Action issued in Chinese Patent Application No. 2013800369039, dated Jan. 6, 2016.
Fourth Office Action issued in Chinese Patent Application No. 2013800369039, dated May 9, 2018.
Garcia-Borreguero et al. "Algorithms for the diagnosis and treatment of restless legs syndrome in primary care" BMC Neurology, 11:28 (2011).
Garcia-Borreguero et al. "Augmentation as a treatment complication of restless legs syndrome: concept and management" Movement Disorders, 22(S18):S476-S484 (2007) (Abstract only).
Garcia-Borreguero et al. "Diagnostic standards for dopaminergic augmentation of restless legs syndrome: report from a World Association of Sleep Medicine—International Restless Legs Syndrome Study Group consensus conference at the Max Planck Institute" Sleep Medicine, 8(5):520-530 (2007) (Abstract only).

(56) References Cited

OTHER PUBLICATIONS

Garcia-Borreguero et al. "Dopaminergic augmentation of restless legs syndrome" Sleep Medicine Reviews, 14(5):339-346 (2010) (Abstract only).
Garcia-Borreguero et al. "Epidemiology of restless legs syndrome: the current status" Sleep Medicine Reviews, 10(3):153-167 (2006) (Abstract only).
Garcia-Borreguero et al. "Systematic evaluation of augmentation during treatment with ropinirole in restless legs syndrome (Willis-Ekbom disease): results from a prospective, multicenter study over 66 weeks" Movement Disorders, 27(2):277-283 (2012) (Abstract only).
Garcia-Borreguero et al. "The long-term treatment of restless legs syndrome/Willis-Ekbom disease: evidence-based guidelines and clinical consensus best practice guidance: a report from the International Restless Legs Syndrome Study Group" Sleep Medicine, 14(7):675-684 (2013).
Garcia-Borreguero et al. "Treatment of restless legs syndrome with pregabalin: a double-blind, placebo-controlled study" Neurology, 74(23):1897-1904 (2010).
Garcia-Borreguero et al. "Validation of the Augmentation Severity Rating Scale (ASRS): a multicentric, prospective study with levodopa on restless legs syndrome" Sleep Medicine, 8(5):455-463 (2007) (Abstract only).
Gelernter et al., "Exclusion of close Linkage of Tourette's Syndrome to D1 Dopamine Receptor," Am. J. Psychiatry, 150(3):449-453 (1993).
Gil-Mast et al. "An amino acid residue in the second extracellular loop determines the agonist-dependent tolerance property of the human D3 dopamine receptor" ACS Chemical Neuroscience, 4(6):940-951 (2013).
Gilbert et al. "Tourette's syndrome improvement with pergolide in a randomized, double-blind crossover trial," Neurology (2000) vol. 54, No. 6, pp. 1310-1315.
Gilbert et al., "Ecopipam, a D1 receptor antagonist, for treatment of tourette syndrome in children: A randomized, placebo-controlled crossover study", Internationlal Perkinson and Movement Disorder Society, vol. 33, No. 8, Aug. 1, 2018, pp. 1272-1280.
Gilbert, D.L. et al. "Tic reduction with pergolide in a randomized controlled trial in children," Neurology (2003) vol. 60, No. 4, pp. 606-611.
Gobira et al., Animal models for predicting the efficacy and side effects of antipsychotic drugs, Revista Brasileira de Psiquiatria 35: S132-S139 (2013).
Godar et al., Animal models of tic disorders: A translational perspective, J. Neurosci. Methods, 238:54-69 (Dec. 2014).
Granado et al. "D1 but not D4 dopamine receptors are critical for MDMA-induced neurotoxicity in mice" Neurotoxicit Research, 25(1):100-109 (2014).
Grant et al., "A Single-Blind Study of 'As-Needed' Ecopipam for Gambling Disorder," Annals of Clinical Psychiatry, 26(3): 1 79-186 (2014).
Griesemer, D.A. "Pergolide in the management of Tourette Syndrome," Journal of Child Neurology (1997) vol. 12, No. 6, pp. 402-403.
Guitart et al. "Functional Selectivity of Allosteric Interactions within G Protein-Coupled Receptor Oligomers: The Dopamine D1-D3 Receptor Heterotetramer" Molecular Pharmacology, 86(4):417-429 (2014).
Haile et al., The dopamine D1 receptor agonist SKF-82958 serves as a discriminative stimulus in the rat, European Journal of Pharmacology 388: 125-131 (2000).
Hall et al. "Changes in mood, depression and suicidal ideation after commencing pregabalin for neuropathic pain" Australian Family Physician, 43(10):705-708 (2014).
Han Dley et al., Serotonin and Tourette's Syndrome: Movements Such as Head-Shakes and Wet-Dog Shakes May Model Human Tics, pp. 235-253 In: Bradley et al. (eds), Serotonin, CNS Receptors and Brain Function, Proceedings of the Serotonin '91 Conference held in Birmingham, United Kingdom on Jul. 14-17, 1991, Pergamon Press (1992).
Han et al. "Dopaminergic modulation of spinal neuronal excitability" The Journal of Neuroscience, 27(48):13192-1320 (2007).
Han et al. "Modulation of AMPA currents by D(1)-like but not D(2)-like receptors in spinal motoneurons" Neuroscience, 158(4):1699-1707 (2009).
Haney et al., Controversies in Translational Research: Drug self-administration, Psychopharmacology, 1 99(3):403-41 9 (2008).
Haugbol et al., Cerebral 5-HT2A receptor binding is increased in patients with Tourette's syndrome, Int. J. Neuropsychopharmacol., 10(2):245-52 (Apr. 2007).
Hayslett et al., Effects of donepezil on DOI-induced head twitch response in mice: implications for Tourette syndrome, Pharmacol. Biochem. Behav., 76(3-4):409-15 (Dec. 2003).
Hayslett et al., Effects of donepezil, nicotine and haloperidol on the central serotonergic system in mice: implications for Tourette's syndrome, Pharmacol. Biochem. Behav., 81 (4):879-86 (Aug. 2005).
Himle et al., Establishing the feasibility of direct observation in the assessment of tics in children with chronic tic disorders, Journal of Applied Behavior Analysis 39: 429-440 (2006).
Hogl et al. "Progressive development of augmentation during long-term treatment with levodopa in restless legs syndrome: results of a prospective multi-center study" Journal of Neurology, 257(2):230-237 (2010).
Hollis et al., Clinical effectiveness and patient perspectives of different treatment strategies for tics in children and adolescents with Tourette syndrome: a systematic review and qualitative analysis, Health Technology Assessment, vol. 20, Issue 4, 496pp (Jan. 2016).
Huang et al. "Smad3 mediates cardiac inflammation and fibrosis in angiotensin II-induced hypertensive cardiac remodeling" Hypertension, 55(5):1165-1171 (2010).
Hubble, J.P. "Pre-clinical studies of pramipexole: clinical relevance" European Journal of Neurology, 7(S1 ):15-20 (2000) (Abstract only).
Ingham, Roger et al., Towards a Functional Neural Systems Model of Developmental Stuttering, J. Fluency Disord., 28(4):297-317, 2003.
International Application No. PCT/US23/36986, International Preliminary Report on Patentability, mailed May 22, 2025.
International Application No. PCT/US23/36986, International Search Report and Written Opinion, mailed Feb. 21, 2024.
International Preliminary Report on Patentability for Application No. PCT/U52014/061080, dated Apr. 19, 2016.
International Search Report and the Written Opinion of the International Searching Authority corresponding to International Patent Application No. PCT/US2016/047591 (14 pages) (mailed Nov. 30, 2016).
International Search Report and Written Opinion for Application No. PCT/US2014/061080, dated Dec. 24, 2014.
International Search Report and Written Opinion of the International Searching Authority for PCT/US2013/050337, Nov. 14, 2013.
Iuga et al. "ROS initiated oxidation of dopamine under oxidative stress conditions in aqueous and lipidic environments" The Journal of Physical Chemistry B, 115(42):12234-12246 (2011).
Jankovic et al., "Tourette's Syndrome and the Law," J. Neuropsychiatry Clin. Neurosci, 18(1):86-95 (2006).
Jankovic J., Tourette's Syndrome, The New England Journal of Medicine, 345(16): 1184-1192 (2001).
Johnson et al. "The dopamine D3 receptor knockout mouse mimics aging-related changes in autonomic function and cardiac fibrosis" PLoS One, 8(8):e74116 (2013).
Karlsson et al., Evaluation of SCH 39166 as PET ligand for central D1 dopamine receptor binding and occupancy in man, Psychopharmacology (Berl) 121(3):300-308 (1995).
Karlsson et al., Lack of apparent antipsychotic effect of the D1-dopamine receptor antagonist SCH39166 in acutely ill schizophrenic patients, Psychopharmacology (Berl) 121(3): 309-316 (1995).
Karson et al., Eye-blink rate in Tourette's syndrome, J Nerv Ment Dis 173(9): 566-569 (1985).

(56) References Cited

OTHER PUBLICATIONS

Keeler et al. "Increased excitability of spinal pain reflexes and altered frequency-dependent modulation in the dopamine D3-receptor knockout mouse" Experimental Neurology, 238(2):273-283 (2012) (Abstract only).
Keeler et al. "Opposing aging-related shift of excitatory dopamine D1 and inhibitory D3 receptor protein expression in striatum and spinal cord" Journal of Neurophysiology, 115:363-369 (2016).
Kenney et al., Tourette's Syndrome, American Family Physician 77(5):651-658 (2008).
Khasnavis et al., A double-blind, placebo-controlled, crossover trial of the selective dopamine D1 receptor antagonist ecopipam in patients with Lesch-Nyhan disease, Mol. Genet. Metab., 118:160-6 (2016).
Kraft, SJ et al., Genetic Bases of Stuttering: The State of the Art, 2011, Folia Phoniatr Logop, 64(1):34-47, 2012.
Kurlan, "Tourette's Syndrome" The New England Journal of Medicine 363 2332-2338, 2010.
Kustermann et al. "Depression and attempted suicide under pregabalin therapy" Annals of General Psychiatry, 13(1):37 (2014).
Kuzhikandathil et al. "Activation of human D3 dopamine receptor inhibits P/Q-type calcium channels and secretory activity in AtT-20 cells" The Journal of Neuroscience, 19(5):1698-1707 (1999).
Kuzhikandathil et al. "Identification and characterization of novel properties of the human D3 dopamine receptor" Molecular and Cellular Neurosciences, 26(1):144-155 (2004) (Abstract only).
Leckman et al., "Tic Disorders: When Habit Forming Neural Systems Form Habits of Their Own?" Chinese Medical Journal (Taipei), 64:669-692 (2001).
Leckman et al., Course of Tic Severity in Tourette Syndrome: The First Two Decades, Pediatrics 102:14-19 (1998).
Lipinski, J.F. et al. "Dopamine agonist treatment of Tourette disorder in children: Results of an open-label trial of pergolide," Movement Disorders (1997) vol. 12, No. 3, pp. 402-407.
Luo et al. "The long-term effects of the dopamine agonist pramipexole in a proposed restless legs syndrome animal model" Sleep Medicine, 12(1):41-46 (2010) (Abstract only).
Machacek et al. "Serotonin 5-HT(2) receptor activation induces a long-lasting amplification of spinal reflex actions in the rat" The Journal of Physiology, 537(Pt 1):201-207 (2001).
Mackie et al. "Long-Term Treatment of Restless Legs Syndrome (RLS): An Approach to Management of Worsening Symptoms, Loss of Efficacy, and Augmentation" CNS Drugs, 29(5):351-357 (2015).
Maggio et al. "Heterodimerization of dopamine receptors: new insights into functional and therapeutic significance" Parkinsonism and Related Disorders, 15(Suppl 4):S2-S7 (2009) (Abstract only).
Maguire, G. et al., Exploratory Randomized Clinical Study of Pagoclone in Persistent Developmental Stuttering: The Examining Pagoclone for Persistent Developmental Stuttering Study., J. Clin. Psychopharmacol. 30:48-56, 2010.
Maguire, Gerald et al., Alleviating Stuttering with Pharmacological Interventions, Expert Opinion on Pharmacotherapy, vol. 5, No. 7, 1565-1571, Jan. 2004.
Maguire, Gerald et al., Risperidone for the Treatment of Stuttering, Journal of Clinical Psychopharmacology, vol. 20, No. 4, 479-482, Aug. 2000.
Malik et al. "The effects of dopamine D3 agonists and antagonists in a nonhuman primate model of tardive dyskinesia" Pharmacology, Biochemistry, and Behavior, 78(4):805-810 (2004) (Abstract only).
Manconi et al. "First night efficacy of pramipexole in restless legs syndrome and periodic leg movements" Sleep Medicine, 8(5):491-497 (2007) (Abstract only).
Manconi et al. "Preferential D2 or preferential D3 dopamine agonists in restless legs syndrome" Neurology, 77(2):110-117 (2011).
Marek, Behavioral evidence for mu-opioid and 5-HT2A receptor interactions, Eur. J. Pharmacol., 474(1):77-83 (Aug. 2003).
Markham, Pergolide: A Review of its Pharmacology and Therapeutic Use in Parkinson's Disease, 3NS Drugs 7(4):328-340 (1997).
Massad et al. "Vitamin B-sensitized photo-oxidation of dopamine" Photochemistry and Photobiology, 84(5):1201-1208 (2008) (Abstract only).
McCreary, et al., The thyrotrophin-releasing hormone analogue MK771 induces tic-like behaviors: the effects of dopamine Di and D2 receptor antagonists, European Journal of Pharmacology, (1999) vol. 369, pp. 1-9.
Mcquade et al., In vivo binding of SCH 39166: a D-1 selective antagonist, J Pharmacol Exp Ther 257(1) 42-49 (1991).
Mcquade,, Robert et al., [3H]SCH 39166, A New D1-Selective Radioligand: In Vitro and In Vivo Binding Analyses, Journal of Neurochemistry, 57(6), 2001-2010, 1991.
Meneely et al. Differential Dopamine D1 and D3 Receptor Modulation and Expression in the Spinal Cord of Two Mouse Models of Restless Legs Syndrome, Frontiers in Behavioral Neuroscience vol. 12 (2018) 14 pages.
Missale et al. "The neurobiology of dopamine receptors: evolution from the dual concept to heterodimer complexes" Journal of Receptor and Signal Transduction Research, 30(5):347-354 (2010) (Abstract only).
Montplaisir et al. "Restless legs syndrome improved by pramipexole: a double-blind randomized trial" Neurology, 52(5):938-943 (1999) (Abstract only).
Mozos-Ansorena et al., "Stuttering Treated with Olanzapine: A Case Report," Actas Esp Psiquiatr, 40(4):231-233 (2012).
Müller N., Tourette's syndrome: clinical features, pathophysiology, and therapeutic approaches, Dialogues Clin Neurosci. 9(2):161-71 (2007).
Nann-Vernotica et al., "Repeated Administration of the D1/5 Antagonist Ecopipan Fails to Attenuate the Subjective Effects of Cocaine," Psychopharmacology, 155:338-347 (2001).
Newbury, D.F. et al., Genetic Advances in the Study of Speech and Language Disorders, Neuron, 68:309-320, 2010.
Notice of Final Rejection for Japanese Application No. 2015-521856, dated Nov. 16, 2016.
Notice of Final Rejection for Korean Application No. 10-2015-7001403, dated Jun. 28, 2016.
Notice of Preliminary Rejection for Korean Application No. 10-2015-7001403, dated Oct. 6, 2016.
Notice of Reasons for Rejection for Japanese Application No. 201 5-52 1856, dated Nov. 30, 2015.
Notice of Reasons for Rejection for Japanese Application No. 201 6-524108, dated Jun. 27, 2018.
Odin et al. "Restless legs syndrome" European Journal of Neurology, 9(S3):59-67 (2002) (Abstract only).
Oertel et al. "Long-term safety and efficacy of rotigotine transdermal patch for moderate-to-severe idiopathic restless legs syndrome: a 5-year open-label extension study" Lancet Neurology, 10(8):710-720 (2011) (Abstract only).
Oertel et al. "Rotigotine transdermal patch in moderate to severe idiopathic restless legs syndrome: a randomized, placebo-controlled polysomnographic study" Sleep Medicine, 11(9):848-856 (2010) (Abstract only).
Office Action and Examination Search Report in Canadian Application No. 2,879,020, dated Feb. 18, 2016, in 3 pages.
Office Action and Examination Search Report in Canadian Application No. 2,879,020, dated Jul. 14, 2017.
Office Action and Examination Search Report in Canadian Application No. 2,879,020, dated Mar. 26, 2019.
Office Action and Examination Search Report in Canadian Application No. 2,879,020, dated Oct. 25, 2016.
Office Action for Israeli Application No. 236403, dated Apr. 9, 2018.
Office Action for Israeli Application No. 236403, dated Jul. 12, 2017.
Oliveira De Almeida et al. The effects of long-term dopaminergic treatment on locomotor behavior in rats Sleep Science, 7(4):203-208 (2014).
Patent Examination Report No. 1 from Australian Patent Application No. 2013289922, dated Nov. 24, 2015 in 5 pages.
Paulus et al. (Less is more: pathophysiology of dopaminergic-therapy-related augmentation in restless legs syndrome. The Lancet Neurology vol. 5, Issue 10, Oct. 2006, pp. 878-886).

(56) References Cited

OTHER PUBLICATIONS

Paulus et al. Dopamine and the spinal cord in restless legs syndrome: does spinal cord physiology reveal a basis for augmentation, Sleep Medicine Reviews, 10(3):185-196 (2006) (Abstract only).
Pettersson, Ingrid et al., A Study on the Contribution of the 1-Phenyl Substituent to the Molecular Electrostatic Potentials of Some Benzazepines in Relation to Selective Dopamine D-1 Receptor Activity, J. Med. Chem., vol. 35, 502-507, 1992.
Pham et al. "Cu(II)-catalyzed oxidation of dopamine in aqueous solutions: mechanism and kinetics" Journal of Inorganic Biochemistry, 137:74-84 (2014) (Abstract only).
Phelps, "Tourette's Disorder: Genetic Update, Neurological Correlates, and Evidence-Based Interventions," School Psychology Quarterly, 23(2):282-289 (2008).
Phillips et al. "Prevalence and correlates of restless legs syndrome: results from the 2005 National Sleep Foundation Poll" Chest, 129(1):76-80 (2006) (Abstract only).
Picchietti et al. "Restless legs syndrome: prevalence and impact in children and adolescents—the Peds REST study" Pediatrics, 120(2):253-266 (2007) (Abstract only).
Prasse, Jane et al., Stuttering: An Overview, American Family Physician, 77:1271-1276, 2008.
Pringsheim et al., Comprehensive systematic review summary: Treatment of tics in people with Tourette syndrome and chronic tic disorders, Neurology, 92(19):907-915 (May 2019).
Rascol, O. "Dopamine agonists: what is the place of the newer compounds in the treatment of Parkinson's disease?" Journal of Neural Transmission Supplementum, 55:33-45 (1999) (Abstract only).
Ravin, L., "Preformulation," Remington's Pharmaceutical Sciences, 17th ed., Mack Publishing Company, Easton, Pa., 1985, Chapter 76, pp. 1409-1423.
Raz, "Translational Attention: From Experiments in the Lab to Helping the Symptoms of Individuals with Tourette's Syndrome," Consciousness and Cognition, (21 ):1591-1594 (2012).
Reagan-Shaw et al., "Dose translation from animal to human studies revisited," FASEB Journal: Official Publication of the Federation of American Societies for Experimental Biology, 22(3):659-661 (2008).
Risperidone, Wikipedia, Mar. 31, 2017, Retrieved from the Internet: URL:https://en.wikipedia.org/wiki/Risperidone, 17 Pages.
Romach et al , "Attenuation of the euphoric effects of cocaine by the dopamine D1/D5 antagonist ecopipam (SCH 39166)" Archives of General Psychiatry, 1999, 56(12) 1101-1106, Dec. 1999.
Salas et al. "All the wrong moves: a clinical review of restless legs syndrome, periodic limb movements of sleep and wake, and periodic limb movement disorder" Clinics in Chest Medicine, 31(2):383-395 (2010) (Abstract only).
Samir et al. "Morphine responsiveness to thermal pain stimuli is aging-associated and mediated by Dopamine D1 and D3 receptor interactions" Neuroscience, 349:87-97 (2017).
Sanberg et al., Nicotine for the treatment of Tourette's syndrome, Pharmacol. Ther., 74(1 ):21-5 (1997).
*Sanofi* v. *Glenmark Pharmaceuticals, Inc.*, USA 204 F.Supp. 3d 665 (2016).
*Sanofi* v. *Watson Laboratories, Inc.*, 875 F.3d 636 (2017).
Scahill, L. et al. "Pharmacologic treatment of tic disorders," Child Adolesc. Psychiatr. Clin. N. Am. (2000) vol. 9, No. 1, pp. 99-117.
Schindler et al., Serotonergic and dopaminergic distinctions in the behavioral pharmacology of (±)-1-(2,5-dimethoxy-4-iodophenyl)-2-aminopropane (DOI) and lysergic acid diethylamide (LSD), Pharmacol Biochem Behav 101(1): 69-76 (2012).
Scholz et al. "Dopamine agonists for restless legs syndrome" The Cochrane Database of Systematic Reviews, (3):CD006009 (2011) (Abstract only).
Scholz et al. "Levodopa for restless legs syndrome" The Cochrane Database of Systematic Reviews, (2):CD005504 (2011) (Abstract only).
Schormair et al. "MEIS1 and BTBD9: genetic association with restless leg syndrome in end stage renal disease" Journal of Medical Genetics, 48(7):462-466 (2011).
Schormair et al. "PTPRD (protein tyrosine phosphatase receptor type delta) is associated with restless legs syndrome" Nature Genetics, 40(8):946-948 (2008).
Schrieber et al., (1-(2,5-dimethoxy-4 iodophenyl)-2-aminopropane)-induced head-twitches in the rat are mediated by 5-hydroxytryptamine (5-HT) 2A receptors: modulation by novel 5-HT2A/2C antagonists, D1 antagonists and 5-HT1A agonists, J Pharmacol Exp Ther 273(1):101-112 (1995).
Second Office Action issued in Chinese Patent Application No. 2013800369039, dated Nov. 28, 2016, in 11 pages.
Shah et al., (+/−)-(N-alkylamino)benzazepine analogs: novel dopamine D1 receptor antagonists, Journal of Medicinal Chemistry 38(21):4284-93 (1995).
Shaygannejad et al., Olanzapine Versus Haloperidol: Which Can Control Stuttering Better?, Int J Prev Med. 4 (Suppl 2):S270-273, 2013.
Shin et al., "Interpretation of Animal Dose and Human Equivalent Dose for Drug Development," The Journel of Korean Oritental Medicine, 31(3):1-7 (2010).
Shreckengost et al. "Bicuculline-sensitive primary afferent depolarization remains after greatly restricting synaptic transmission in the mammalian spinal cord" The Journal of Neuroscience, 30(15):5283-5288 (2010).
Silver et al. "A 10-year, longitudinal assessment of dopamine agonists and methadone in the treatment of restless legs syndrome" Sleep Medicine, 12(5):440-444 (2011) (Abstract only).
Singer et al., "Abnormal dopamine uptake sites in postmortem striatum from patients with Tourette's syndrome," Ann. Neurol., 30:558-562 (1991).
Spieler et at. "Restless legs syndrome-associated intronic common variant in Meis1 alters enhancer function in the developing telencephalon" Genome Research, 24(4):592-603 (2014).
Staley et al., Tourette disorder: a cross-cultural review, Comprehensive Psychiatry 38(1): 6-16 (1997).
Starr et al., Differential effects of dopamine D1 and D2 agonists and antagonists on velocity of movement, earing and grooming in the mouse. Implications for the roles of D1 and D2 receptors, Neuropharmacology 25(5): 455-463 (1986).
Starr et al., Grooming in the mouse is stimulated by the dopamine D1 agonist SKF 38393 and by low doses of the D1 antagonist SCH 23390, but is inhibited by dopamine D2 agonists, D2 antagonists and high doses of SCH >3390. Pharmacology Biochemistry & Behavior 24(4):837-9(1986).
Stefansson et al. "A genetic risk factor for periodic limb movements in sleep" The New England Journal of Medicine, 357(7):639-647 (2007).
Stiasny-Kolster et al. "Low-dose pramipexole in the management of restless legs syndrome. An open label trial." Neuropsychobiology, 50(1):65-70 (2004) (Abstract only).
Stiasny-Kolster et at. "Effectiveness and tolerability of rotigotine transdermal patch for the treatment of restless legs syndrome in a routine clinical practice setting in Germany" Sleep Medicine, 14(6):475-481 (2013) (Abstract only).
Surmeier et al. "Coordinated expression of dopamine receptors in neostriatal medium spiny neurons" The Journal of Neuroscience, 16(20):6579-6591 (1996).
Swerdlow and Sutherland, Using animal models to develop therapeutics for Tourette Syndrome, Pharmacology and Therapeutics 108(3):281-93 (2005).
Taylor et al., Dopamine receptor modulation of repetitive grooming actions in the rat: potential relevance for Tourette syndrome, Brain Res 1322:92-101 (2010).
Third Office Action issued in Chinese Patent Application No. 201 3800369039, dated Aug. 21, 2017.
Thorpe et al. "Possible sites of therapeutic action in Restless Legs Syndrome: Focus on dopamine and [alpha]2 [delta] ligands" European Neurology, 66(1):18-29 (2011).
Tizabi et al., Nicotine attenuates DOI-induced head-twitch response in mice: implications for Tourette syndrome, Prog. Neuropsychopharmacol. Biol. Psychiatry, 25(7) : 1445-57 (Oct. 2001).

(56) References Cited

OTHER PUBLICATIONS

Trenkwalder et al. "Restless legs syndrome: pathophysiology, clinical presentation and management" Nature Reviews Neurology, 6(6):337-346 (2010) (Abstract only).
Trenkwalder et al. "The restless legs syndrome" Lancet Neurology, 4(8):465-475 (2005) (Abstract only).
Trotti et al. "Restless legs syndrome" Handbook of Clinical Neurology, 100:661-673 (2011) (Abstract Only).
VanHole, Nicholas. Shared Consciousness: A Social History of Tourette Syndrome and its Treatments. University of Montana. ScholarWorks at University of Montana. Theses, Dissertations, Professional Papers. 2012, 123 pages.
Wei, L. "Immunological aspect of cardiac remodeling: T lymphocyte subsets in inflammation-mediated cardiac fibrosis" Experimental and Molecular Pathology, 90(1):74-78 (2011) (Abstract only).
Weisman et al., Systematic review: pharmacological treatment of tic disorders—efficacy of antipsychotic and alpha-2 adrenergic agonist agents, Neuroscience and Biobehavioral Reviews 37(6):1162-71 (2013).
Westrich et al. "Development of tolerance in D3 dopamine receptor signaling is accompanied by distinct changes in receptor conformation" Biochemical Pharmacology 79:897-907 (2010).
Winkelmann et al. "Genome-wide association study of restless legs syndrome identifies common variants in three genomic regions" Nature Genetics, 39(8):1000-1006 (2007) (Abstract only).
Winkelmann et al. "Opioid and dopamine antagonist drug challenges in untreated restless legs syndrome patients" Sleep Medicine, 2(1):57-61 (2001) (Abstract only).
Winkelmann et al. "Sensory symptoms in restless legs syndrome: the enigma of pain" Sleep Medicine, 14(10):934-942 (2013) (Abstract only).
Winkelmann et at. "Genome-wide association study identifies novel restless legs syndrome susceptibility loci on 2p14 and 16q12.1" PLoS Genetics, 7(7):e1002171 (2011).
Winkelmann, J. "Genetics of restless legs syndrome" Current Neurology and Neuroscience Reports, 8(3):211-216 (2008) (Abstract only).
Xiong et al. "Molecular genetic studies of DMT1 on 12q in French-Canadian restless legs syndrome patients and families" American Journal of Medical Genetics Part B: Neuropsychiatric Genetics, 144B(7):911-917 (2007) (Abstract only).
Xu et al. "Dopamine D1 receptor mutant mice are deficient in striatal expression of dynorphin and in dopamine-mediated behavioral responses" Cell, 79(4):729-742 (1994).
Xu et al. "Elimination of cocaine-induced hyperactivity and dopamine-mediated neurophysiological effects in dopamine D1 receptor mutant mice" Cell, 79(6):945-955 (1994) (Abstract only).
Yamada et al., Acute immobilization stress reduces (+/−)DOI-induced 5-HT2A receptor-mediated head shakes in rats, Psychopharmacology (Berl), 1 19(1):9-14 (May 1995).
Zeng et al. "D3 Dopamine Receptor Directly Interacts With D1 Dopamine Receptor in Immortalized Renal Proximal Tubule Cells" Hypertension 47(part 2):573-579 (2006).
Zhu et al. "Expression and distribution of all dopamine receptor subtypes (D1-D5) in the mouse lumbar spinal cord: A real-time polymerase chain reaction and non-autoradiographic in situ hybridization study" Neuroscience, 149(4):885-897 (2007).
Zhu et al. "Unaltered D1, D2, D4, and D5 dopamine receptor mRNA expression and distribution in the spinal cord of the D3 receptor knockout mouse" Journal of Comparative Physiology A: Neuroethology, Sensory, Neural, and Behavioral Physiology, 194(11):957-962 (2008).
Zypadhera, European Medicines Agency, Apr. 25, 2014, XP002769139, 7 Pages.
Atkinson et al., Efficacy, Safety, and Tolerability of Ecopipam in Tourette Syndrome With Psychiatric Comorbidities, American Psychiatric Association, Poster 4519, 1 Page (May 2023).
Clinical Trials—NCT01065558, Study Details, "Safety and Tolerability of the D1 Dopamine Receptor Antagonist Ecopipam in Patients With Lesch-Nyhan Disease," <https://clinicaltrials.gov/study/NCT01065558?term=NCT01065558%27&rank=1&a=3> (posted Apr. 18, 2013).
Clinical Trials—NCT04007991, Results Posted, "Ecopipam Tablets to Study Tourette's Syndrome in Children and Adolescents (D1AMOND)" <https://clinicaltrials.gov/study/NCT04007991?term=NCT04007991&rank=1&tab=results> (posted Oct. 4, 2023).
Clinical Trials—NCT04007991, Study Details, "Ecopipam Tablets to Study Tourette's Syndrome in Children and Adolescents (D1AMOND)," <https://clinicaltrials.gov/study/NCT04007991?term=NCT04007991&rank=1&a=10> (posted Oct. 4, 2023).
Clinical Trials—NCT01065558, Results Posted, "Safety and Tolerability of the D1 Dopamine Receptor Antagonist Ecopipam in Patients With Lesch-Nyhan Disease," <https://clinicaltrials.gov/study/NCT01065558?term=NCT01065558%27&rank=1&a=3&tab=results> (posted Apr. 18, 2013).
Clinical Trials—NCT01215357, Results Posted, "Clinical Study to Determine if Ecopipam Can Reduce Urges to Gamble," <https://clinicaltrials.gov/study/NCT01215357?term=NCT01215357&rank=1&a=7&tab=results> (posted May 14, 2024).
Clinical Trials—NCT01215357, Study Details, "Clinical Study to Determine if Ecopipam Can Reduce Urges to Gamble," <https://clinicaltrials.gov/study/NCT01215357?term=NCT01215357&rank=1&a=7> (posted May 14, 2024).
Clinical Trials—NCT01244633, Results Posted, "Ecopipam Treatment of Tourette Syndrome," <https://clinicaltrials.gov/study/NCT01244633?term=NCT01244633&rank=1&tab=results> (posted Sep. 29, 2015).
Clinical Trials—NCT01244633, Study Details, "Ecopipam Treatment of Tourette Syndrome," <https://clinicaltrials.gov/study/NCT01244633?term=NCT01244633&rank=1> (posted Sep. 29, 2015).
Clinical Trials—NCT01751802, Results Posted, "Ecopipam Treatment of Self-Injurious Behavior in Subjects With Lesch-Nyhan Disease," <https://clinicaltrials.gov/study/NCT01751802?term=NCT01751802&rank=1 &tab=results> (posted Apr. 22, 2024).
Clinical Trials—NCT01751802, Study Details, "Ecopipam Treatment of Self-Injurious Behavior in Subjects With Lesch-Nyhan Disease," <https://clinicaltrials.gov/study/NCT01751802?term=NCT01751802&rank=1> (posted Apr. 22, 2024).
Clinical Trials—NCT02102698, Study Details, "Ecopipam Treatment of Tourette's Syndrome in Subjects 7-17 Years," <https://clinicaltrials.gov/study/NCT02102698?term=NCT02102698&rank=1&a=12> (posted Apr. 19, 2024).
Clinical Trials—NCT02909088, Study Details, "Efficacy and Tolerability of Ecopipam in Adults With Childhood Onset Fluency Disorder (Stuttering)." <https://clinicaltrials.gov/study/NCT02909088?term=NCT02909088&rank=1&a=2> (posted Oct. 26, 2016).
Clinical Trials—NCT03218969, Study Details, "Treatment of Restless Leg Syndrome (RLS) Augmentation With Ecopipam, a D1 Specific Antagonist (RLS-Ecopipam)," <https://clinicaltrials.gov/study/NCT03218969?term=NCT03218969&rank=1&a=4> (posted Jul. 24, 2018).
Clinical Trials—NCT04114539, Results Posted, "Ecopipam Tablets to Study Tourette Syndrome in Children and Adolescents—Open Label Extension," <https://clinicaltrials.gov/study/NCT04114539?term=NCT04114539&rank=1&tab=results> (posted Feb. 1, 2024).
Clinical Trials—NCT04114539, Study Details, "Ecopipam Tablets to Study Tourette Syndrome in Children and Adolescents—Open Label Extension," <https://clinicaltrials.gov/study/NCT04114539?term=NCT04114539&rank=1> (posted Feb. 1, 2024).
Clinical Trials—NCT04492956, Results Posted, "Effects of Ecopipam or Placebo in Adults With Stuttering (Speak Freely)," <https://clinicaltrials.gov/study/NCT04492956?term=NCT04492956&rank=1&a=11&tab=results> (posted Apr. 28, 2022).
Clinical Trials—NCT04492956, Study Details, "Effects of Ecopipam or Placebo in Adults With Stuttering (Speak Freely)," <https://clinicaltrials.gov/study/NCT04492956?term=NCT04492956&rank=1> (posted Apr. 28, 2022).
Clinical Trials—NCT04764851, Study Details, "Drug-Drug Interaction Study to Evaluate the Effects of Ecopipam on the Pharmacokinetics of Multiple Substrates," <https://clinicaltrials.gov/study/NCT04764851?term=NCT04764851&rank=1> (posted May 24, 2021).

(56) References Cited

OTHER PUBLICATIONS

Clinical Trials—NCT04881955, Study Details, “Study of the Absorption, Metabolism, and Excretion of [14C]-Ecopipam in Healthy Male Subjects,” <https://clinicaltrials.gov/study/NCT04881955?term=NCT04881955&rank=1> (posted Dec. 3, 2021).

Clinical Trials—NCT05334108, Study Details, “Drug-Drug Interaction Study to Evaluate the Effects of Ecopipam on the Pharmacokinetics of Multiple Substrates for Drug Metabolism and Transport,” <https://clinicaltrials.gov/study/NCT05334108?term=NCT05334108&rank=1> (posted Dec. 12, 2022).

Clinical Trials—NCT05615220, Results Posted “Ecopipam Tablets to Study Tourette’s Disorder in Children, Adolescents and Adults (D1AMOND),” <https:///clinicaltrials.gov/study/NCT05615220?term=NCT05615220&rank=1&tab=results> (posted Nov. 25, 2025).

Clinical Trials—NCT05615220, Study Details, “Ecopipam Tablets to Study Tourette’s Disorder in Children, Adolescents and Adults (D1AMOND),” <https://clinicaltrials.gov/study/NCT05615220?term=NCT05615220&rank=1> (Version 24 posted Nov. 30, 2024).

Clinical Trials—NCT06021522, Study Details, “A Study to Evaluate Long-term Safety of Ecopipam Tablets in Children, Adolescents and Adults With Tourette’s Disorder,” <https://clinicaltrials.gov/study/NCT06021522?term=NCT06021522&rank=1&tab=history&a=7#version-content-panel> (Version 7 posted Nov. 13, 2024).

Clinical Trials—NCT06669091, Study Details, “Food-effect Study of Ecopipam Pharmacokinetics,” <https://clinicaltrials.gov/study/NCT06669091?term=NCT06669091&rank=1> (posted Jan. 27, 2025).

Cunniff et al., Design of a Confirmatory Trial of Ecopipam in Tourette Syndrome, American Academy of Neurology, Poster 011, 1 Page (Apr. 2023).

Cunniff et al., Design of a Phase 3 Maintenance-of-Effect Trial of Ecopipam in Tourette Syndrome, 15th European Conference on Tourette Syndrome, Poster 15, 1 Page (Jun. 2023).

Dubow et al., Ecopipam, a Selective D1 Antagonist in Development for the Treatment of Tourette Syndrome in Children and Adolescents: the Phase 2b D1AMOND Study Design, International Congress of Parkinson’s Disease and Movement Disorders, Poster 1381, 1 Page (Sep. 2019).

Freidy et al., Increasing Ecopipam Exposure Improves Yale Global Tic Severity Scale-Total Tic Scores in Children and Adolescents With Tourette Syndrome: Results From a Population Pharmacokinetic Model-Based Simulation Using D1AMOND Trial Data, Poster 007, 1 Page (Apr. 2023).

Freidy et al., Population Pharmacokinetics of Ecopipam and Active Metabolite (EBS-101-40853) in Healthy Volunteers and Pediatric Patients With Tourette Syndrome, Poster W-048, 1 Page (Nov. 2023).

Gilbert et al., Ecopipam Does Not Adversely Affect Metabolic Parameters in Pediatric Patients With Tourette Syndrome: Results From a Phase 2b Randomized, Placebo-Controlled Trial With a 12-Month Open-Label Extension, Child Neurology Society, Poster 96, 1 Page (Nov. 2024).

Gilbert et al., Ecopipam Does Not Adversely Affect Metabolic Parameters in Pediatric Subjects With Tourette Syndrome: Results From a Phase 2b With 12-Month Open-Label Extension Study, International Congress of Parkinson’s Disease and Movement Disorders, Poster 632, 1 Page (Oct. 2024).

Gilbert et al., Effect of Ecopipam, a Selective Dopamine-1 Receptor Antagonist, on Tic Characteristics as Assessed by the YGTSS: Results From the Phase 2b (D1AMOND) Randomized, Double-Blind, Placebo-Controlled Clinical Trial in Tourette Syndrome, International Congress of Parkinson’s Disease and Movement Disorders, Poster 1526, 1 Page (2024).

Gilbert et al., Effect of Ecopipam, a Selective Dopamine-1 Receptor Antagonist, on Tic Characteristics as Assessed by the YGTSS: Results From the Phase 2b Randomized, Double-Blind, Placebo-Controlled Clinical Trial in Tourette Syndrome, Child Neurology Society 53rd Annual Meeting, Poster 97, 1 Page (Nov. 2024).

Gilbert et al., Effect of Ecopipam, a Selective Dopamine-1 Receptor Antagonist, on Tic Characteristics as Assessed by YGTSS: Results From the Phase 2b (D1AMOND) Randomized, Double-Blind, Placebo-Controlled Clinical Trial in Tourette Syndrome, Neurology, 102(7):12 Pages (Apr. 2024).

Gilbert et al., Long-Term Safety and Durability of Effect of Ecopipam in Pediatric Patients With Tourette Syndrome: Results of a 12-Month Open-Label Extension Study, International Congress of Parkinson’s Disease and Movement Disorders, Poster PSS943, 1 Page (Aug. 2023).

Gilbert et al., Safety and Effect of 12-Month Ecopipam Treatment in Pediatric Patients with Tourette Syndrome, Movement Disorders Clinical Practice, 12(8):1157-1166 (May 2025).

Gilbert et al., Safety and Tolerability of Ecopipam in Tourette Syndrome With Psychiatric Comorbidities, American Academy of Neurology Annual Meeting, Poster 001, 1 Page (Apr. 2024).

Gilbert et al., Safety and Tolerability of Ecopipam in Tourette Syndrome With Psychiatric Comorbidities, International Congress of Parkinson’s Disease and Movement Disorders, Poster 631, 1 Page (Oct. 2024).

Gilbert et al., Safety and Tolerability of Ecopipam in Tourette Syndrome With Psychiatric Comorbidities, Neurology, 102(7):12 Pages (Apr. 2024).

Gilbert, From D1 Receptors to Tic Reduction: Results From the Phase III Study of Ecopipam for Tourette Syndrome, European Society for the Study of Tourette, 70 Pages (2025).

Isaacs et al., Clinical Profile of Children and Adolescents Newly Diagnosed With Tourette Syndrome: Observational Cohort Study of a Large Electronic Health Records Database, American Academy of Neurology, Poster 6-005, 1 Page (Apr. 2025).

Mahableshwarkar et al., Ecopipam in Children and Adolescents with Tourette Syndrome: Results from a Randomized, Double-Blind, Placebo-Controlled Phase 2b Study, American Academy of Neurology, 1 page (Apr. 2022).

Mahableshwarkar et al., Randomized, Double-Blind, Placebo-Controlled Phase 2b Study of Ecopipam in Children and Adolescents With Tourette Syndrome, APA 2022 Annual Meeting, Poster P6-019, 1 page (May 2022).

McGuire et al., An Anchor-Based Method to Establish Clinically Meaningful Changes in YGTSS-TTS Using Data From the Phase 2b and Safety Extension Studies of Ecopipam, a Selective D1 Receptor Antagonist, in Tourette Syndrome, American Academy of Child & Adolescent Psychiatry, Poster 6.72, 1 Page (Oct. 2024).

McGuire et al., Changes in Metabolic Parameters and Determination of Minimal Clinically Important Difference in YGTSS-TTS Using Data From the Randomized Phase 2b and Open-Label Extension Studies of Ecopipam for Tourette Syndrome, American Academy of Neurology, Poster 6-002, 1 Page (Apr. 2025).

McGuire et al., Determining Clinically Meaningful Improvement in Children and Adolescents with Tourette Syndrome Receiving Pharmacotherapy, Journal of Child and Adolescent Psychopharmacology, 35(8):447-453 (Oct. 2025).

Schmith et al., Evaluation of the Effect of CYP3A4 and P-Glycoprotein Inhibition by Itraconazole or Induction by Rifampicin on the Pharmacokinetics of Ecopipam and its Metabolites, American Society for Clinical Pharmacology and Therapeutics, Poster LB-012, 1 Page (May 2025).

Schmith et al., Metabolic Profiling of Ecopipam, American Society for Clinical Pharmacology and Therapeutics, Poster PII-123, 1 Page (Mar. 2024).

Schmith et al., Microdosing Approach to Evaluate Whether Ecopipam Affects Drug Metabolism and Transport of Concomitant Medications, American Society for Clinical Pharmacology and Therapeutics Poster PII-125, 1 Page (Mar. 2024).

Schmith et al., The Effect of UGT Inhibition on the Pharmacokinetics of Ecopipam and its Metabolite, American Society for Clinical Pharmacology and Therapeutics, Poster PII-088, 1 Page (Mar. 2023).

Tomczak et al., High Rates of Discontinuation of D2 Receptor Antagonists as Treatment of Tourette Syndrome in Children: A Retrospective Database Analysis, American Academy of Neurology, Poster 6-001, 1 Page (Apr. 2025).

Wanaski et al., Effects of Ecopipam on Growth and Development in Juvenile Rats, American Academy of Neurology, Poster 010, 1 Page (Apr. 2024).

(56) References Cited

OTHER PUBLICATIONS

Wanaski et al., The Effect of Ecopipam and Its Metabolites on Cardiac Repolarization, QTcF, American Academy of Neurology Annual Meeting, Poster 5-014, 1 Page (Apr. 2025).

* cited by examiner $F_{a\ IO}$=intraoral fraction absorbed
$F_{a\ GI}$=gastrointestinal fraction absorbed
$F_g$=fraction available over gut wall
$F_h$=fraction available over liver
FPL=First pass loss
$F_{total}$=total bioavailability=$F_{IO}$ + $F_{GI}$ Responder defined as >25% decrease in the YGTSS-TTS Score
AUC = area under the concentration-time curve of ecopipam + EBS-101-40853 (assuming equipotency) during a dosing interval at steady-state; TD = Tourette's disorder; YGTSS-TTS = Yale Global Tic Severity Score-Total Tic Scale.

PHARMACEUTICAL DOSAGE FORMS AND METHODS OF USE

CROSS-REFERENCE TO RELATED APPLICATION

This application is a Continuation of International Application No. PCT/US25/20111, filed Mar. 14, 2025, which claims the benefit or priority to U.S. Provisional Patent Application No. 63/565,834 filed Mar. 15, 2024, which are hereby claimed and the disclosures are incorporated herein by reference in their entirety.

BACKGROUND

Field of the Disclosure

The disclosure relates generally to pharmaceutical dosage forms containing a D1/D5 receptor antagonist, for example ecopipam, or a salt of derivative thereof, and methods of using such dosage forms. More particularly, the disclosure relates to pharmaceutical dosage forms for use in delivering ecopipam in a dosage form that provides for intraoral absorption of the ecopipam while maintaining a reduced pH in the oral cavity.

Brief Description of Related Technology

D1/D5 receptor antagonists are described in U.S. Pat. Nos. 4,973,586, 6,262,049, 7,211,574, 7,504,391, 9,949,983, and 11,298,361 and International (PCT) Patent Application Publication WO 2014/012063 A1.

SUMMARY

One aspect of the disclosure provides a pharmaceutical dosage form for intra-oral absorption of ecopipam, comprising ecopipam or a pharmaceutically acceptable salt thereof and a pH modifier, the pH modifier being present in amount such that the pharmaceutical dosage form has a pH of 2 to 4, wherein when the dosage form is in solid form, the pH is as measured after dissolving the dosage form in 30 g of artificial saliva having a pH of 6.72.

One aspect of the disclosure provides a pharmaceutical dosage form for use in delivering an active pharmaceutical agent (API) in a manner other than oral systemic delivery, wherein the API is selected from one or more of those in Table I

TABLE I

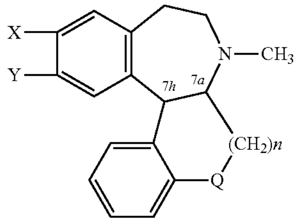

| Col. 1 Q | Col. 2 n | Col. 3 stereo-chemistry of 7a and 7b H's | Col. 4 X | Col. 5 Y |
|---|---|---|---|---|
| $CH_2$ | 1 | cis | $CH_3O$ | OH |
| $CH_2$ | 1 | cis | HO | $CH_3O$ |
| $CH_2$ | 1 | trans | $CH_3O$ | OH |

TABLE I-continued

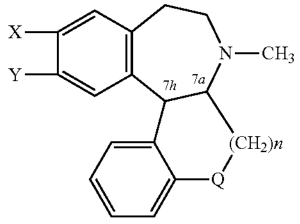

| Col. 1 Q | Col. 2 n | Col. 3 stereo-chemistry of 7a and 7b H's | Col. 4 X | Col. 5 Y |
|---|---|---|---|---|
| $CH_2$ | 1 | trans | HO | $CH_3O$ |
| $CH_2$ | 1 | trans | Cl | OH |
| $CH_2$ | 1 | 7b(S):7a(R)(+) | Cl | OH |
| $CH_2$ | 1 | 7b(R):7a(S)(−) | Cl | OH |
| $CH_2$ | 1 | cis | Cl | OH |
| $CH_2$ | 1 | trans | H | OH |
| $CH_2$ | 2 | trans | $CH_3O$ | OH |
| $CH_2$ | 2 | trans | HO | $CH_3O$ |
| $CH_2$ | 1 | trans | $CH_3$ | OH |
| $CH_2$ | 1 | trans | Cl | $NH_2$ |
| O | 1 | trans | H | OH |
| $CH_2$ | 0 | trans | Cl | OH |

;

or 6,7,7a,8,9,13b-hexahydro-2-hydroxy-3-methoxy-7-methyl-5H-benzo[d]naphtho[2,1-b]azepine;

6,7,7a,8,9,13b-hexahydro-2-hydroxy-7-methyl-5H-benzo[d]naphtho[2,1-b]azepine;

6,7,7a,8,9,13b-hexahydro-3-chloro-2-hydroxy-7-methyl-5H-benzo[d]naphtho[2,1-b]azepine;

6,7,7a,8,9,13b-hexahydro-2-hydroxy-3,7-dimethyl-5H-benzo[d]naphtho[2,1-b]azepine;

6,7,7a,8,9,13b-hexahydro-2-amino-7-methyl-5H-benzo[d]naphtho[2,1-b]azepine;

6,7,7a,8,9,13b-hexahydro-2-amino-3-chloro-7-methyl-5H-benzo[d]naphtho[2,1-b]azepine;

6,7,7a,8,9,13b-hexahydro-2-amino-3,7-dimethyl-5H-benzo[d]naphtho[2,1-b]azepine;

6,6a,7,8,9,13b-hexahydro-12-methoxy-7-methyl[1]benzopyrano[4,3-a][3]benzazepine;

6,6a, 7,8,9,13b-hexahydro-7-methyl[1]benzopyrano[4,3-a][3]benzazepin-12-ol;

6,6a,7,8,9,13b-hexahydro-3-hydroxy-2-methoxy-7-methyl-5H-benzo[d]naphtho[2,1-b]azepine;

2-hydroxy-3-methoxy-7-methyl-5,6,7,7a,8,9,10,14b-octahydro-benzo[d]benzo[3,4] cyclo-hepta[1,2-b]azepine;

3-hydroxy-2-methoxy-7-methyl-5,6,7,7a,8,9,10,14b-octahydro-benzo[d]benzo[3,4] cyclo-hepta[1,2-b]azepine;

5,6,7,7a,8,12b-hexahydro-2-hydroxy-3-chloro-7-methyl-benz[d]indeno[2,1-b]azepine;

5,6,7,7a,8,12b-hexahydro-2-hydroxy-3-methoxy-7-methyl-benz[d]indeno[2,1-b]azepine;

5,6,7,7a,8,12b-hexahydro-2-amino-3-chloro-7-methyl-benz[d]indeno[2,1-b]azepine;

5,6,7,7a,8,12b-hexahydro-2-hydroxy-7-methyl-benz[d]indeno[2,1-b]azepine;

5,6,7,7a,8,12b-hexahydro-3,7-dimethyl-2-hydroxy-benz[d]indeno[2,1-b]azepine;

5,6,7,7a,8,12b-hexahydro-3-chloro-7-cyclopropylmethyl-2-hydroxy-benz[d]indeno[2,1b]azepine;

5,6,7,7a,8,12b-hexahydro-7-allyl-3-chloro-2-hydroxy-benz[d]indeno[2,1-b]azepine;

5,6,7,7a,8,12b-hexahydro-3-chloro-2-hydroxy-7,8,8-trimethyl-benz[d]indeno[2,1-b]azepine;

5,6,7,7a,8,11b-hexahydro-3-chloro-7-methylthieno[2',3':4,5]cyclopenta[1,2-a][3]benzazepine-2-ol;

5,6,7,7a,8,12b-hexahydro-2-hydroxy-3-chloro-benz[d]indeno[2,1-b]azepine;

6,7,7a,8,9,13b-hexahydro-3-chloro-2-hydroxy-5H-benzo[d]naphtho[2,1-b]azepine; or 6,7,7a,8,9,13b-hexahydro-2-amino-3-trifluoromethyl-7-methyl-5H-benzo[d]naphtho[2,1b]azepine;

or SCH23390 and compounds related thereto, including SCH 12679 and the compounds described in U.S. Pat. No. 4,477,378 (which is hereby incorporated by reference in the present application in its entirety), BTS-73-947, NNC-22-0010, JHS-271, JHS-198, JHS-136, A69024, and NNC687. D1/D5 partial agonists include SKF38393, fenoldapam; SKF75670A; SKF 81297; SKF82958; or dinapsoline; or

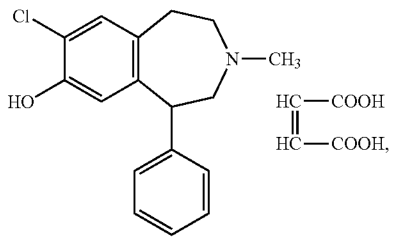

SCH 23390

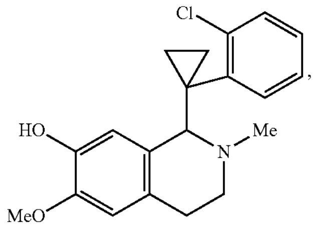

BTS-73-947

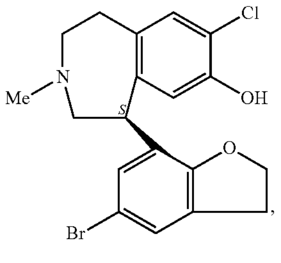

NNC-22-0010

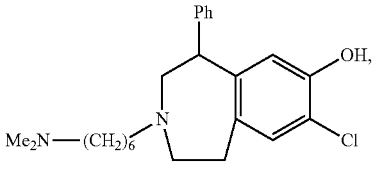

JHS 271

-continued

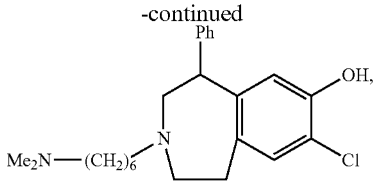

JHS 198

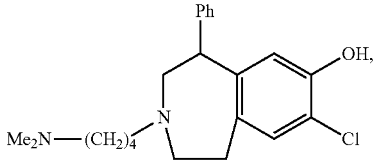

JHS 136

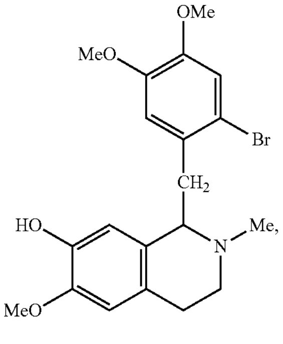

A 69024

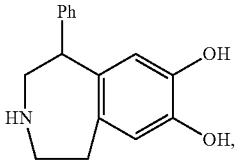

SKF 58611A

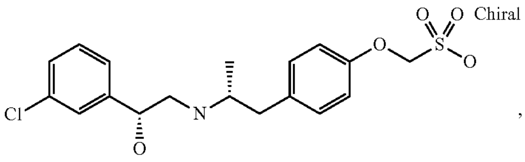

, and

BMS 196085

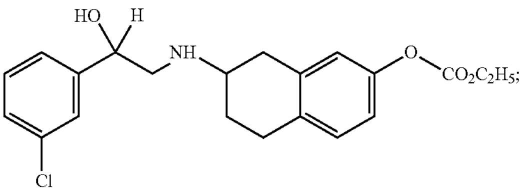

SR 58611A or a pharmaceutically acceptable salt, solvate, hydrate, prodrug, structural analog, metabolite, or polymorph of any of the foregoing, or a pharmaceutically acceptable salt of any of the foregoing.

Another aspect is a method of administering a pharmaceutical dosage form of the disclosure herein with a UGT inhibitor, or on a dosing schedule that overlaps a dosing schedule of a UGT inhibitor schedule.

Another aspect is a method of administering a pharmaceutical dosage form of the disclosure herein with a CYP3A4 inducer, or on a dosing schedule that overlaps a dosing schedule of a CYP3A4 inducer schedule.

Another aspect is a method of improving the safety profile of ecopipam comprising administering to a subject in need thereof the pharmaceutical dosage form of the disclosure.

Another aspect is a method of reducing one or more first pass metabolite concentrations in plasma comprising administering to a subject in need thereof the pharmaceutical dosage form of any one of the preceding claims. In such aspects, the first pass metabolite concentration can be an ecopipam glucuronide concentration. The glucuronide concentration can be reduced by 75-85% using pharmaceutical dosage forms in accordance with the disclosure as compared to an oral dosage form for oral systemic administration. For example, the first pass metabolite concentration can be an EBS-101-40853 concentration and the reduction can be about 48-55% as compared to an oral dosage form for oral systemic administration. For example, the first pass metabolite concentration can be an EBS-101-40853 glucuronide concentration and the reduction can be about 60-76% as compared to an oral dosage form for oral systemic administration.

In any of the aspects of the disclosure, the pharmaceutical dosage form can be administered in one or more doses. The pharmaceutical dosage forms of the disclosure can be administered using an initial dose titration schedule or without an initial dose titration schedule.

In any of the aspects of the disclosure, the pharmaceutical dosage form of the disclosure can be administered to a subject in need thereof to achieve a total daily dose of ecopipam or pharmaceutically acceptable salt thereof of about 1 mg to about 200 mg, or about 5 mg to about 100 mg. For example, a subject in need thereof can be administered the pharmaceutical dosage form to achieve a total daily dosage of ecopipam or pharmaceutically acceptable salt thereof of 200 mg or less, 125 mg or less, 100 mg or less, 50 mg or less. In any of the aspects of the disclosure, the pharmaceutical dosage form of the disclosure can be administered to a subject in need thereof to achieve a total daily dosage of ecopipam of pharmaceutically acceptable salt thereof in an amount of less than 2 mg/kg, 1.5 mg/kg or less, 1 mg/kg or less, 0.5 mg/kg or less, or any values therebetween.

Another aspect is a method of treating a subject in need of a dopamine D1 antagonist or a dopamine D1/D5 antagonist comprising administering to the subject a dosage form of any one of the disclosure herein or according to a method of any one of the disclosure herein.

Further aspects and advantages will be apparent to those of ordinary skill in the art from a review of the following detailed description. While the dosage forms and methods are susceptible of embodiments in various forms, the description hereafter includes specific embodiments with the understanding that the disclosure is illustrative, and is not intended to limit the invention to the specific embodiments described herein.

DETAILED DESCRIPTION

Pharmaceutical dosage forms in accordance with the disclosure provide for intra-oral absorption of an active pharmaceutical ingredient (API). The pharmaceutical dosage forms of the disclosure can include an active pharmaceutical ingredient and a pH modifier that is capable of modifying the pH of the oral cavity upon dissolution of the formulation to a pH at which the active pharmaceutical ingredient has improved solubility.

Embodiments of the pharmaceutical dosage forms of the disclosure are pharmaceutical dosage forms for intraoral absorption of ecopipam or a pharmaceutically acceptable salt thereof. It has been surprisingly found that ecopipam or pharmaceutically acceptable salt thereof has improved solubility in pH environments of about 2 to 4. In addition to improved solubility, the use of a pharmaceutical formulation that provides for intraoral absorption of the ecopipam or pharmaceutically acceptable salt thereof advantageously avoids first pass metabolism present with oral administration. As a result of reducing or entirely avoiding first pass metabolism, the dosage forms of the disclosure beneficially exhibit reduced side effects, with an improved safety profile, such as for example, a cardiac safety profile, as well as can have reduced drug-drug interactions as compared to an oral dosage form in which the API is absorbed in the GI tract (oral systemic administration). Dosage forms in accordance with the disclosure have also been observed to have improved bioavailability of ecopipam and/or improved central nervous system availability of ecopipam, which can improve efficacy and/or allow for reduced dosing amounts to be used as compared to oral dosage forms for oral systemic administration. This can be beneficial to patient compliance through a reduction of dosing burden.

Figure 1:
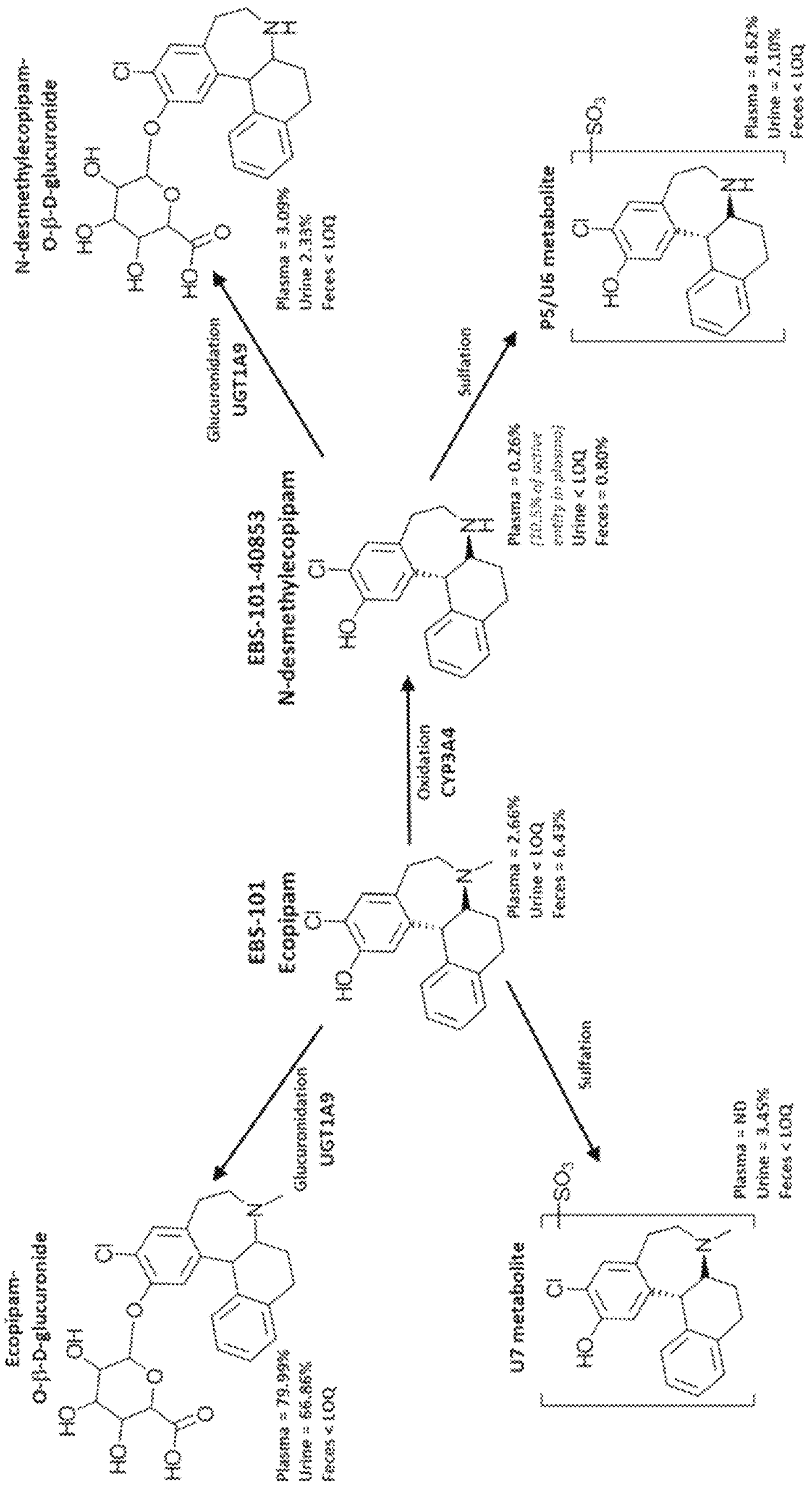
FIG. 1 is a schematic showing metabolism of ecopipam in humans.

The absolute bioavailability of ecopipam is unknown in humans, but likely low since only 1.67% of the radiolabeled dose was found as ecopipam in plasma. It has been found that ecopipam undergoes significant first-pass metabolism following oral absorption. FIG. 1 illustrates the metabolism of ecopipam in humans. It was observed that with oral administration, ecopipam is primarily eliminated through metabolism, with <1% of the dose excreted unchanged in the urine. The primary metabolite is ecopipam glucuronide, which accounted for ~80% of radioactivity in plasma and 67% of radioactivity in the urine (Example 4). Ecopipam glucuronide has the highest concentration present in human and animal plasma after oral administration and iso the metabolite with the lowest safety margin, particularly for cardiac safety. Without intending to be bound by theory, it is believed that the intraorally absorbed pharmaceutical formulations in accordance with the disclosure exhibit improved bioavailability and/or reduced side effects, such as QT effects, at least in part by avoiding the first pass metabolism seen with oral administration; in addition, improved bioavailability may occur from improved solubility and absorbance of ecopipam intraorally as a result of the dosage form maintaining a reduced pH in the oral cavity upon administration. For example, the first pass metabolite concentration can be an ecopipam glucuronide concentration. The ecopipam glucuronide concentration can be reduced by 75-85% using pharmaceutical dosage forms in accordance with the disclosure as compared to an oral dosage form for oral systemic administration. For example, the first pass metabolite concentration can be an EBS-101-40853 concentration and the reduction can be about 48-55% as compared to an oral dosage form for oral systemic administration. For example, the first pass metabolite concentration can be an EBS-101-40853 glucuronide concentration and the reduction can be about 60-76% as compared to an oral dosage form for oral systemic administration.

For example, as a result of the reduced first pass metabolite concentrations, intraoral absorption of ecopipam is believed to have reduced side effects, such as concentration-related prolongation of the QT interval and reduced drug-drug interactions originating from the gastrointestinal tract. This can improve the safety profile of ecopipam, which in turn can allow for use in a wider variety of patient populations. For example, the improved safety profile and reduced drug-drug interactions can allow for use in patients with moderate to severe hepatic and renal impairment. For example, the dosage forms of the disclosure can allow ecopipam to be dosed with UGT inhibitors or CYP3A inducers. For example, orally dissolvable pharmaceutical formulations in accordance with the disclosure can reduce drug-drug interaction of ecopipam as a perpetrator including but not limited to effects of ecopipam inducing CYP3A, P-glycoprotein, and CYP2C enzymes as well as UGT1A1.

The results shown in Example 3 revealed that upon administration of ecopipam via the oral systemic route, only about 1.69% of that active entity circulates in plasma. Most of the administered dose of drug circulates as glucuronic metabolites. Ecopipam is glucuronidated in the gastrointestinal tract and in the liver. Accordingly, dosing ecopipam, and similar compounds, such as other fused benzazepines, by routes other than oral systemic administration (in which the API is absorbed in the GI tract), can result in equivalent plasma levels of ecopipam using smaller doses, e.g. on the order of ¾, ½, ⅓, ¼, ⅕, ⅒ or any value therebetween.

Pharmaceutical dosage forms for intraoral absorption of ecopipam can include ecopipam or pharmaceutically active salt thereof and a pH modifier included in an amount such that a pH of the dosage form is about 2 to about 4. When the dosage form is provided as a solid the pH is measured after the dosage form is dissolved in 30 g of artificial *salvia* having a pH of 6.72. In any of the formulations disclosed herein, the ecopipam can be in free base form or as a pharmaceutically acceptable salt, or a solvate, hydrate, or prodrug, or pharmaceutically acceptable salt of any of the foregoing. It has advantageously been observed that improved solubility of the API, in whatever form present, can be made by adjusting the pH of the oral cavity to a pH at which the API form has the best solubility levels. Such modification of the oral cavity to provide a pH environment in which the API has improved solubility is believed to contribute to improved $C_{max}$ as compared to an oral administration where absorption occurs in the GI tract. Reference herein to ecopipam and pharmaceutically acceptable salts thereof should be understood to include solvates, hydrates, and prodrugs thereof. It has advantageously been found that when the dosage form has a pH of about 2 to about 4, the pH of the saliva in the mouth can be lowered significantly after administration of the pharmaceutical dosage form, for example, at least 0.5, at least 1, or at least 2 pH units. For example, after administration, the salvia of the subject to whom the dosage form is administered can be reduced from the natural pH of around 6-7 (with average pH being 6.7) to a pH of 6.5 or less, 6 or less, 5.5 or less, 5 or less, 4.5 or less, or a 4 or less, which is advantageous for improved solubility of ecopipam during intraoral absorption. Any known excipients for use in orally disintegrating dosage forms can be used. For example, gelatin and non-gelatin excipients as base excipients for orally disintegrating dosage forms are known in the art and can be used in the dosage forms of the disclosure. For example, the base excipients used in the Zydis® (Catalent) orally disintegrating tablet dosage form can be used. Dosage forms in accordance with the disclosure being present in a Zydis matrix further include the adjustment of pH using a pH modifier to provide for a pH reduction in the mouth during disintegration of the dosage form. Inclusion of other excipients are also contemplated herein, including, but not limited to binders, fillers, disintegrants, flavoring agents, nitrosamine scavengers, and combinations thereof.

The pharmaceutical dosage form can be provided in various dosage forms for intraoral absorption including, but not limited to, powders, sachets, sublingual tablets, orally disintegrating tablets, gels, films, buccal patches/films/tablets, oral sprays, lozenges, and the like. Excipients useful in providing such dosage forms are contemplated for use in the formulations of the disclosure.

The pharmaceutical dosage forms and methods are contemplated to include any combination of one or more of the additional optional elements, features, and steps further described below, unless stated otherwise.

Definitions

In jurisdictions that forbid the patenting of methods that are practiced on the human body, the meaning of "administering" of a composition to a human subject shall be restricted to prescribing a substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

Compounds

The active compounds for use in the dosage forms and methods described in here are referred to herein and throughout as the API, active pharmaceutical ingredient. The API for use in a dosage form and the methods described herein can include those in the generic formula in the table below.

TABLE I

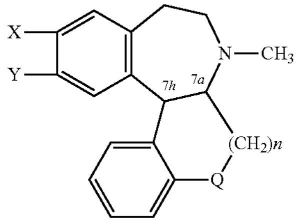

| Col. 1 Q | Col. 2 n | Col. 3 stereo-chemistry of 7a and 7b H's | Col. 4 X | Col. 5 Y | Ki (nM) Col. 6 $^3$H-23390 | Ki (nM) Col. 7 $^3$H-Spip | Col. 8 CAR (MED) |
|---|---|---|---|---|---|---|---|
| $CH_2$ | 1 | cis | $CH_3O$ | OH | 6450 | >100,000 | |
| $CH_2$ | 1 | cis | HO | $CH_3O$ | 44,800 | >100,000 | |
| $CH_2$ | 1 | trans | $CH_3O$ | OH | 23 | 2500 | 30 (po); 0.3-1 (sc) |
| $CH_2$ | 1 | trans | HO | $CH_3O$ | 2970 | >100,000 | |
| $CH_2$ | 1 | trans | Cl | OH | 5.5 | 11,500 | 30 (po); 0.3 (sc) |
| $CH_2$ | 1 | 7b(S): 7a(R)(+) | Cl | OH | 1800 | >100,000 | >30 (po) |
| $CH_2$ | 1 | 7b(R): 7a(S)(−) | Cl | OH | 12 | 14,300 | 30 (po) |
| $CH_2$ | 1 | cis | Cl | OH | 6200 | >100,000 | |
| $CH_2$ | 1 | trans | H | OH | 30 | 3500 | |
| $CH_2$ | 2 | trans | $CH_3O$ | OH | 292 | >100,000 | 10 (sc) |
| $CH_2$ | 2 | trans | HO | $CH_3O$ | 7730 | >100,000 | 10 (sc) |
| $CH_2$ | 1 | trans | $CH_3$ | OH | 119 | 7200 | |
| $CH_2$ | 1 | trans | Cl | $NH_2$ | 70 | 4175 | 3 (po) |
| O | 1 | trans | H | OH | 121 | — | |
| $CH_2$ | 0 | trans | Cl | OH | 10 | 2600 | |

Such compounds are known in the art and are more fully described in U.S. Pat. No. 4,973,586, which is hereby incorporated by reference in its entirety.

In one embodiment, the API can be a metabolite of ecopipam, or another API described herein. For example, the API can be a desmethyl compound, such as the desmethyl form of ecopipam, which has been referenced in the art as SCH 40853 or EBS-101-04853.

More specifically, the API can be:

6,7,7a,8,9,13b-hexahydro-2-hydroxy-3-methoxy-7-methyl-5H-benzo[d]naphtho[2,1-b]azepine;

6,7,7a,8,9,13b-hexahydro-2-hydroxy-7-methyl-5H-benzo[d]naphtho[2,1-b]azepine;

6,7,7a,8,9,13b-hexahydro-3-chloro-2-hydroxy-7-methyl-5H-benzo[d]naphtho[2,1-b]azepine;

6,7,7a,8,9,13b-hexahydro-2-hydroxy-3,7-dimethyl-5H-benzo[d]naphtho[2,1-b]azepine;

6,7,7a,8,9,13b-hexahydro-2-amino-7-methyl-5H-benzo[d]naphtho[2,1-b]azepine;

6,7,7a,8,9,13b-hexahydro-2-amino-3-chloro-7-methyl-5H-benzo[d]naphtho[2,1-b]azepine;

6,7,7a,8,9,13b-hexahydro-2-amino-3,7-dimethyl-5H-benzo[d]naphtho[2,1-b]azepine;

6,6a, 7,8,9,13b-hexahydro-12-methoxy-7-methyl[1]benzopyrano[4,3-a][3]benzazepine;

6,6a,7,8,9,13b-hexahydro-7-methyl[1]benzopyrano[4,3-a][3]benzazepin-12-ol;

6,6a, 7,8,9,13b-hexahydro-3-hydroxy-2-methoxy-7-methyl-5H-benzo[d]naphtho[2,1-b]azepine;

2-hydroxy-3-methoxy-7-methyl-5,6,7,7a,8,9,10,14b-octahydro-benzo[d]benzo[3,4] cyclo-hepta[1,2-b]azepine;

3-hydroxy-2-methoxy-7-methyl-5,6,7,7a,8,9,10,14b-octahydro-benzo[d]benzo[3,4] cyclo-hepta[1,2-b]azepine;

5,6,7,7a,8,12b-hexahydro-2-hydroxy-3-chloro-7-methyl-benz[d]indeno[2,1-b]azepine;

5,6,7,7a,8,12b-hexahydro-2-hydroxy-3-methoxy-7-methyl-benz[d]indeno[2,1-b]azepine;

5,6,7,7a,8,12b-hexahydro-2-amino-3-chloro-7-methyl-benz[d]indeno[2,1-b]azepine; 5,6,7,7a,8,12b-hexahydro-2-hydroxy-7-methyl-benz[d]indeno[2,1-b]azepine;

5,6,7,7a,8,12b-hexahydro-3,7-dimethyl-2-hydroxy-benz[d]indeno[2,1-b]azepine;

5,6,7,7a,8,12b-hexahydro-3-chloro-7-cyclopropylmethyl-2-hydroxy-benz[d]indeno[2,1b]azepine;

5,6,7,7a,8,12b-hexahydro-7-allyl-3-chloro-2-hydroxy-benz[d]indeno[2,1-b]azepine;

5,6,7,7a,8,12b-hexahydro-3-chloro-2-hydroxy-7,8,8-trimethyl-benz[d]indeno[2,1-b]azepine;

5,6,7,7a,8,11b-hexahydro-3-chloro-7-methylthieno[2',3':4,5]cyclopenta[1,2-a][3]benzazepine-2-ol;

5,6,7,7a,8,12b-hexahydro-2-hydroxy-3-chloro-benz[d]indeno[2,1-b]azepine;

6,7,7a,8,9,13b-hexahydro-3-chloro-2-hydroxy-5H-benzo[d]naphtho[2,1-b]azepine; or 6,7,7a,8,9,13b-hexahydro-2-amino-3-trifluoromethyl-7-methyl-5H-benzo[d]naphtho[2,1b]azepine.

The API can be in the form of a pharmaceutically acceptable salt and/or a trans isomer. An example D1/D5 receptor antagonist useful in the dosage forms and methods of the invention is SCH39166, which is also known as PSYRX101, EBS-101, or ecopipam (6,7,7a,8,9,13b-hexahydro-3-chloro-2-hydroxy-5H-benzo[d]naphtho[2,1-b]azepine or, in trans form, (−)-trans-6,7,7a,8,9,13b-hexahydro-3-chloro-2-hydroxy-5H-benzo[d]naphtho[2,1-b]azepine). Ecopipam conforms to the structure:

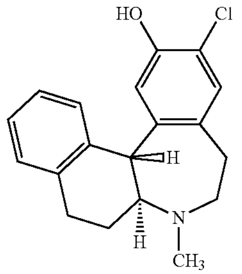

SCH 39166

Other D1/D5 receptor antagonists that are useful in the present methods include: SCH23390 and compounds related thereto, including SCH 12679 and the compounds described in U.S. Pat. No. 4,477,378 (which is hereby incorporated by reference in the present application in its entirety), BTS-73-947, NNC-22-0010, JHS-271, JHS-198, JHS-136, A69024, and NNC687. D1/D5 partial agonists include SKF38393, fenoldapam; SKF75670A; SKF 81297; SKF82958; and dinapsoline.

The structures of some of these compounds are illustrated here:

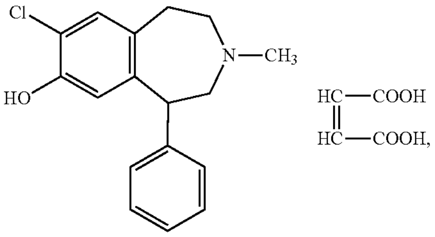

SCH 23390

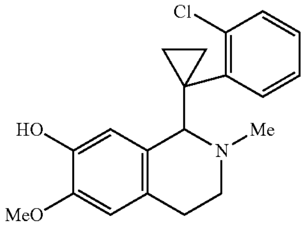

,

BTS-73-947

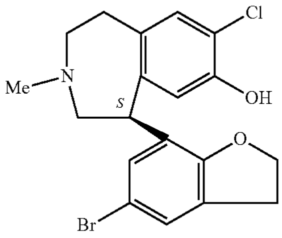

,

NNC-22-0010

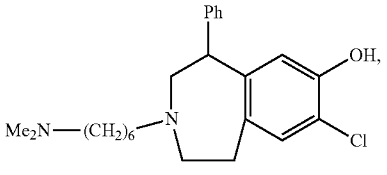

JHS 271

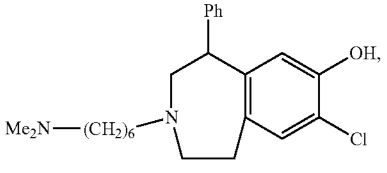

JHS 198

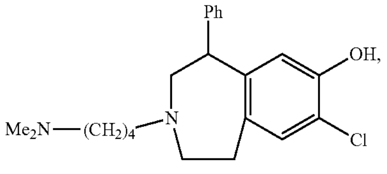

JHS 136

-continued

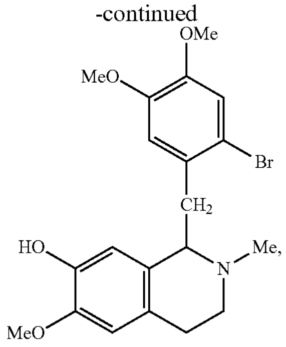

A 69024

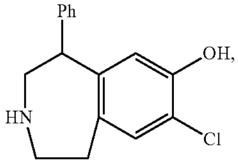

SKF 58611A

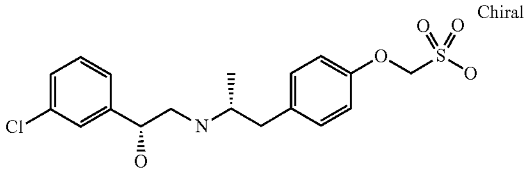

, and

BMS 196085

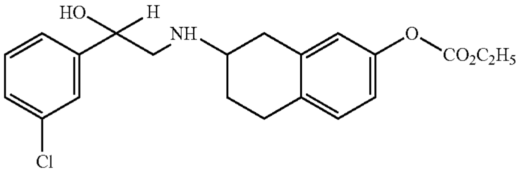

SR 58611A

A dosage form described herein can include pharmaceutically acceptable salts, solvate, hydrate, prodrug, structural analog, metabolite, or polymorphs of any of the foregoing APIs, or any other APIs described herein.

The chemical names of these APIs appear in the following Table:

| | |
|---|---|
| SCH 39166 (ecopipam) | (−)-trans-6,7,7a,8,9,13b-hexahydro-3-chloro-2-hydroxy-N-methyl-5H-benzo [d]-naphtho-[2,1-b]azepine |
| SCH 23390 | (d)-7-chloro-8-hydroxy-3-methyl-1-phenyl-2,3,4,5-tetrahydro-1H-3-benzazepine maleate |
| BTS-73-947 | 1-[1-(2-chlorophenyl)cyclopropyl]-1,2,3,4-tetrahydro-7-hydroxy-6-methoxy-2-methyl-(S)-isoquinolinol |
| NNC-22-0010 | (+)-5-(5-bromo-2,3-dihydro-7-benzofuranyl)-8-chloro-2,3,4,5-tetrahydro-3-m ethyl-1H-3-benzazepin-7-ol |
| JHS-271 | 8-chloro-3-[6-(dimethylamino)hexyl]-2,3,4,5-tetrahydro-5-phenyl-1H-3-benzazepin-7-ol |
| JHS-198 | 8-chloro-3-[6-(dimethylamino)hexyl]2,3,4,5-tetrahydro-5-phenyl-1H-3-benzazepin-7-ol with boranecarbonitrile (1:1). |
| JHS-136 | 8-chloro-3-[4-(dimethylamino)butyl]-2,3,4,5-tetrahydro-5-phenyl-1H-3-benzazepin-7-ol |
| A-69024 | 1-[(2-bromo-4,5-dimethoxyphenyl)methyl]-1,2,3,4-tetrahydro-6-methoxy-2-met hyl-7-isoquinolinol |

Compounds useful in the present invention can be prepared in a variety of ways known to one of ordinary skill in the art of organic synthesis. Starting materials are readily available, and it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures. Thus, the foregoing D1/D5 antagonists can be prepared by known methods. For example, one of ordinary skill in the art could synthesize APIs by the methods described in U.S. Pat. No. 5,302,716, which is hereby incorporated by reference in its entirety, and such APIs are useful in the present methods. One could also consult the published PCT applications WO 93/13073; WO 93/1702; WO 95/25102. One could also consult J. Med. Chem., 38 (21): 4284-4293, 1995. A D1/D5 partial agonist is SKF 38393, having the chemical name 2,3,4,5-tetrahydro-1-phenyl-1-H-3-benzazepine-7,8-diol. Other APIs useful in the present invention are those described in U.S. Pat. No. 4,477,378 (esters of substituted 8-hydroxy-1-phenyl-2,3,4,5-tetrahydro-1H-3-benzazepines), which is hereby incorporated by reference herein in its entirety.

Ecopipam free base is a benzazepine derivative that is a selective antagonist of the D1 family of receptors. Ecopipam hydrochloride (SCH 39166 HCl; C19H20NOCl·HCl) has the chemical structure:

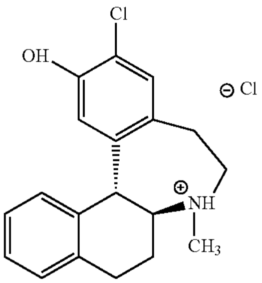

SCH 39166 HCl

The APIs described herein, including those conforming to any formula, can be asymmetric (e.g., having one or more stereocenters). All stereoisomers, such as enantiomers and diastereomers, are intended unless otherwise indicated. The present APIs that contain asymmetrically substituted carbon atoms can be used in mixed form or isolated in optically active or racemic forms. An API useful in the dosage forms described herein can have a trans configuration. Methods for preparing optically active forms from optically active starting materials are known in the art. These methods include resolution of racemic mixtures and stereoselective synthesis. For example, one can conduct fractional recrystallization using a chiral resolving acid that is an optically active, salt-forming organic acid. Suitable resolving agents for use in these methods can be, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other useful resolving agents include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). A suitable elution solvent composition can be determined by one skilled in the art.

Cis and trans geometric isomers of the present APIs are described and may be isolated as a mixture of isomers or as separated isomeric forms. Compounds for use in the dosage forms described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Tautomeric forms can be in equilibrium or sterically locked into one form by appropriate substitution.

Compounds for use in the dosage forms described herein also include all isotopes of atoms occurring in the intermediate or final compounds. Isotopes include those atoms having the same atomic number but different mass numbers. For example, isotopes of hydrogen include tritium and deuterium.

The term "compound," as used herein with respect to any compound conforming to one of the D1/D5 antagonists or partial agonists described above, is meant to include all stereoisomers, geometric isomers, tautomers, and isotopes of the structures referenced (e.g., depicted). All APIs, and all pharmaceutically acceptable salts thereof, can be used in a solvated or hydrated form. In some embodiments, the compounds for use the dosage form (regardless of form; e.g., salts) are "substantially isolated," meaning that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99%, by weight, of a compound of the invention. Methods for isolating compounds and their salts are routine in the art.

As noted, the dosage forms described herein can include "pharmaceutically acceptable salts," a term that generally refers to derivatives of the disclosed APIs wherein the parent compound is modified by converting an existing acid or base moiety to its salt form. "Pharmaceutically acceptable" generally encompasses those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit:risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts useful in the dosage forms described herein include the conventional non-toxic salts of the parent compound formed, for example, from non-toxic inorganic or organic acids. The pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in Remington's Pharmaceutical Sciences, 17th ed., Mack Publishing Company, Easton, Pa., 1985, p. 1418 and the Journal of Pharmaceutical Science, 66:2, 1977.

In addition to, or instead of, ecopipam hydrochloride, ecopipam free base may be in the form of another pharmaceutically acceptable salt. Such salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane disulfonic, oxalic, isethionic, and the like.

Dosage Forms

A pharmaceutical dosage form according to the present disclosure is one suitable for and preferably specifically designed for use in delivering such a D1/D5 antagonist described herein in a manner other than oral systemic delivery. A pharmaceutical dosage form according to the present disclosure is one suitable for and preferably specifically designed for use in delivering such an API for pulmonary, transdermal, or transmucosal delivery. Transmucosal routes contemplated include the mucosal linings of the nasal, rectal, vaginal, ocular, and oral cavities, especially the nasal, ocular and oral cavities (including sublingual or buccal), especially the nasal, and oral cavities. For example, in embodiments, the dosage form is for intraoral absorption of ecopipam. Oral dosage forms or oral tablets are made with reference herein to dosage forms which are for oral systemic administration, that is dosage forms administered orally for absorption of the API in the GI tract. By comparison, dosage forms in accordance with the disclosure are designed for absorption of the API by other means, e.g., intraoral, pulmonary, transdermal, or transmucosal.

The dosage form can include a bioadhesive, e.g. a mucoadhesive material, or a buccoadhesive material.

The bioadhesive material, mucoadhesive material, or buccoadhesive material can contain or be a polymer material. Bioadhesive polymers are polymers that can adhere to a biological substrate. Mucoadhesive materials adhere to a substrate which is mucosal tissue. The mucoadhesive polymer can have predominantly anionic hydrophilicity with hydrogen bond-forming groups. The mucoadhesive polymer can have suitable surface property for wetting mucus/mucosal tissue surfaces. The mucoadhesive polymer can have sufficient flexibility to penetrate the mucus network or tissue crevices Suitable bioadhesive materials include AB block copolymers of oligo(methyl methacrylate) and PAA, acacia, and polyvinyl alcohol, anionic types, Carbopol e.g. 934P, cationic types, chitosan (e.g. free or cross-linked by an anionic polymer), copolymers of PAA and PEG monoethylether monomethacrylate, epoxy resins, Eudragit polymers (e.g. Eudragit L-100, an anionic copolymer based on methacrylic acid and methyl methacrylate), gelatin, gellan gum, glycol, guar gum, hyaluronic acid, hydrogels of poly(N N-dimethylaminoethyl methacrylate-co-methyl methacrylate) e.g., poly(DMA/MMA) cross-linked with DVB, hydrophilic pressure-sensitive adhesives (PSAs), hydroxyethyl cellulose, hydroxyethyl methacrylate, hydroxypropyl cellulose, hydroxypropyl methylcellulose, methylcellulose, a modified starch-polyacrylic acid mixture, monomeric alpha-cyanoacrylate, PAA complexed with PEGylated drug conjugate, pectin, poly(acrylic acid/divinyl benzene), polyacrylates, polymethacrylates, polycarbophil, polyethylene carboxymethyl cellulose, polymers with thiol groups, polymethyl vinyl ether-maleic anhydride, polystyrenes, polyurethanes, polyvinyl pyrrolidone, psyllium amberlite-200 resin, sodium alginate, sodium alginate, tamarind gum, thermally modified starch, tragacanth, and xanthan gum.

A dosage form for oral cavity delivery/absorption can be designed for application or insertion in a specific region of the oral cavity, e.g. buccally or sublingually, or otherwise in the oral cavity.

A dosage form for buccal administration is inserted into the buccal pouch, the space between the lip and gum in the mouth. The dosage form can take any suitable shape, including oval, and are often relatively flat. The buccal dosage form can be hard tablet. The buccal dosage form can be formulated to dissolve slowly, or erode slowly. The buccal dosage form can be one that melts at body temperature to release an API as described herein, for example a matrix type dosage form, e.g. one in which an API as described herein is in solution as the matrix is cooled and solidified and when remelted the API is in solution and available for absorption. The buccal dosage form can be a patch. The buccal dosage form can be a compressed tablet. In addition or in the alternative, the buccal dosage form can include a bioadhesive material.

Sublingual dosage forms, e.g. tablets, are placed under the tongue. A sublingual tablet can be designed to dissolve rapidly, and the API thus released.

The dosage form for oral cavity delivery/absorption can take any suitable shape and consistency, and can be selected from one or more types in the group of a chewing gum, a chewable lozenge, a chewable tablet, a film, a gel, a liquid, a lozenge, a microporous hollow fiber, a mouthwash, an oral lyophilizate, an oral strip, an oravescent, an orodispersible, a patch, a powder, a semisolid, a sprayable liquid, a tablet, a tape, and a wafer.

The dosage form can have a monolithic design, e.g. a matrix, or can be designed with multiple functional regions and/or coatings. For example, the dosage form can be designed for unidirectional release (e.g. a unidirectional release tablet), a bilayer (e.g. a bilayer tablet with a bioadhesive layer containing API and a water impermeable coating), a triple layer (e.g. a triple layer tablet with a bioadhesive layer, an API layer, and a water impermeable coating) or with an API-containing mucoadhesive layer and an API-free backing layer (e.g. ethylcellulose). The dosage form can be a reservoir type, e.g. one that includes a cavity for the API and optional excipients separate from a bioadhesive, and optionally with an impermeable backing that can have one or more functions, e.g. to control the direction of API delivery, to reduce shape deformation, to reduce disintegration while in the mouth (e.g. as a saliva barrier). A bioadhesive can be used as an API carrier and/or as a bioadhesive for an API-loaded, non-adhesive layer. The API can be microencapsulated.

Bioadhesive microspheres can be used for buccal or nasal delivery of the API. Such microspheres can be made from albumin, chitosan, diethylaminoethyl (DEAE)-dextran, hyaluronic acid, starch, combinations thereof, and other suitable materials known in the art.

An API-loaded, optionally non-adhesive region, e.g. a layer, can be made of any suitable material, for example one or more in the group of an acrylic acid polymer, ethylcellulose, hydroxypropyl cellulose, methylcellulose, polyethylene oxide and polyvinyl pyrrolidone, poly(ethylacrylate methylmethacrylate), polyethyene glycol, and natural polymers including gaur-gum, pectins, starches, gelatin, and casein. The region can contain or be based on one or more excipients selected from lactose, glucose, sucrose, starch, crystalline cellulose, dextrin, cyclodextrin, silicic acid anhydride, aluminum silicate, talc, calcium stearate, magnesium stearate, beeswax, polyethylene glycol, and polyphosphate. The region can be water soluble, or water swellable, or water-degradable. The region can include a water soluble polymer in which the API is dispersed.

Orodispersible dosage forms include orally disintegrating tablets, and oral lyophilizates or wafers which present even faster disintegration than compressed counterparts, and thin films. Lyophilization can also produce buccal wafers that adhere to mucosa, including optionally for sustained API release.

A bioadhesive tablet is similar to conventional tablets and can be prepared by various methods, including wet granulation, dry granulation, and direct compression processes. In addition to mucoadhesive components, a tablet can contain a water-soluble excipient, e.g. a high molecular weight polyethylene glycol, or mannitol. A fast-dissolving tablet can include a mixture of a water-soluble polymer and a crystalline sugar. Mannitol and natural polysaccharides such as gelatin and alginates can be used.

A film dosage form is a solid, which dissolves in a relatively short period of time when placed in the mouth without drinking water or chewing. These can also be designed as buccal films, and can be referred to as fast dissolving oral films, and oral strips and tapes, and thin films. A bioadhesive film or patch can be prepared by solvent casting, with steps of dissolving the API in a casting solution, casting a film, and drying the film, and then optionally laminating with a backing layer or a release liner. A bioadhesive film or patch can be prepared by hot-melt extrusion method.

Chewable lozenges can be gummy-type lozenges. A chewable lozenge can be based on a modified suppository formula, e.g. including glycerin, gelatin, and water. These lozenges can be fruit-flavored and can have an acidic taste to cover the taste associated with glycerin. Soft lozenges can include ingredients such as PEG 1000 or 1450, or a sugar-acacia base. Silica gel can be added to prevent sedimentation. Soft lozenges can also include flavors and sweeteners to aid compliance, including in children and adolescents.

An adhesive gel can be based on a mixture of polyacrylic acid and polymethacrylate.

Chewing gums can include a tasteless, insoluble masticatory gum base that consists of natural or synthetic elastomers. The gum can include excipients such as fillers, softeners, and sweetening and flavoring agents. Natural gum bases include chicle and smoked natural rubber, and synthetic gum bases include styrene-butadiene rubber, polyethylene, and polyvinylacetate. The gum base can form about 20 wt. % to 80 wt. % of the gum, or 30 wt. % to 65 wt. % of the gum, or 35 wt. % to 50 wt. % of the gum, or 40 wt. % of the gum. The gum base can also include plasticizers, waxes, lipids, and emulsifiers.

The dosage form can include one or more excipients, for example selected from the groups of an absorption enhancer (also called permeation enhancer), an antioxidant, a binder, a carrier, a colorant, a diluent, a disintegrant, a flavor, a lubricant, a pH modifier, a plasticizer, a preservative, a sweetener, a taste masking agent, a taste modulating agent, and a viscosity modifier, including one or more from each group of excipients.

Antioxidants include ascorbic acid and sodium metabisulfite.

Binders include microcrystalline cellulose, mannitol, lactose, starches, including corn starch and pregelatinized starch, sorbitol, crospovidone, cross-linked povidone, polyvinylpyrrolidone, hydroxypropyl cellulose, hydroxypropyl methylcellulose, sodium starch glycolate, and silicified microcrystalline cellulose.

Coating materials include carboxymethylcellulose, polyvinyl alcohol (PVA), and ethylcellulose.

Colorants include FD&C dyes and natural colorants.

Diluents (e.g. mannitol, lactose, sucrose, and sorbitol) can aid in the formulation of chewable tablets by compression. They can facilitate disintegration with chewing and can aid taste and mouth feel. A combination of microcrystalline cellulose and guar gum (Avicel CE-15) can lead to a dosage form with reduced grittiness, resulting in a creamier mouth feel.

Disintegrants include croscarmellose sodium, croscarmellose calcium, and cross-linked sodium carboxymethylcellulose.

Flavoring agents include mint and fruit flavors.

Lubricants include magnesium stearate and stearic acid.

Modifiers of pH include, for example, citric acid, ascorbic acid, acetic acid, hydrochloric acid, salts thereof, and combinations thereof. The modifier can be present, for example, in an amount based on the total weight of the dosage form of about 0.01 wt % to about 0.8 wt %., about 0.01 wt % to about 0.05 wt %, about 0.1 wt % to about 0.5 wt %, or about 0.05 wt % to about 0.4 wt %, and any values therebetween. For example, the pH modifier can be included in an amount based on the total weight of the formulation of about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8 wt % or any values therebetween or ranges defined by such values. The selection of the amount of pH modifier to include in the formulation can be made based on ordinary skill in the art to achieve a target pH. The target pH can be selected based on identification of a pH at which solubility of the API improves and the pH of the formulation needed to achieve and maintain the saliva at the target pH alter administration of the pharmaceutical dosage form. For example, pharmaceutical dosage forms for intraoral administration of ecopipam or a pharmaceutically acceptable salt thereof can include the pH modifier in an amount sufficient to achieve a pharmaceutical formulation pH of about 2 to about 4. This has advantageously been found to reduce the pH of saliva to less than 6.5, or 6 or less, or 5.5 or less, or 5 or less, or 4.5 or less, or 4 or less, which can advantageously improve solubility of the ecopipam or pharmaceutically acceptable salt thereof, and in particular ecopipam HCl.

Plasticizers include glycerin, propylene glycol, and polyethylene glycol.

Preservatives include benzalkonium chloride, methylparaben, and propylparaben.

Taste masking agents for blocking bitterness include adenosine monophosphate, lipoproteins, phospholipids, eriodictyol, homoeriodictyol, and sodium laurylsulfate.

Viscosity modifiers include hydroxypropyl methylcellulose and sodium alginate.

Microencapsulation of an API for taste masking can be achieved by phase separation or coacervation. The same technologies may be used to encapsulate an API for formulation into chewable, softchew, and fast dissolving dosage forms. Complexation of an API with an ion exchange resin can be used for taste masking.

Xylitol (a sweet sugar alcohol), has a high negative heat of solution, making it a good excipient for chewable tablets. A compressible sugar, e.g. containing sucrose granulated with a small amount of a modified dextrin, is useful for making compressed dosage forms such as tablets. In addition or in the alternative, spray-dried crystalline maltose and directly compressible sucrose (e.g., 95% sucrose and 5% sorbitol) can be used for compressed dosage forms such as tablets.

Permeation Enhancers can include chelators (e.g., citric acid, EDTA, EGTA, methoxy salicylates, sodium salicylate); surfactants, including nonionic, e.g., polyoxyethylene vegetable-based fatty ethers derived from lauryl, cetyl, stearyl or oleyl alcohols (e.g., Brij), dodecylmaltoside, laureth-9, ethoxylated fatty acids (e.g. Myrj), poloxamer, polysorbate 80, span, sucrose esters, Tween, cationic (e.g., benzalkonium chloride, cetylmethylammonium bromide, Cetyl pyridinium chloride), and anionic (e.g., sodium dodecyl glycocholate, sodium lauryl sulfate, laureth-9 sodium dodecylsulfate); bile salts and other steroidal detergents (e.g., sodium glycocholate, sodium taurocholate, saponins, sodium taurodeoxycholate, sodium taurodihydrofusidate, and sodium glycodihydrofusidate); fatty acids (e.g., Oleic acid, Caprylic acid, Lauric acid, Lyso phosphatidyl choline, Phosphatidyl choline, sodium myristate); non-surfactants (e.g., 1-dodecylazacycloheptane-2-one (Azone), salicylates, and sulfoxides); enzymes (e.g., phopholipases, hyaluronidases, neuraminidase, and chondroitinase ABC); and Cyclodextrins (e.g., α, β, γ, Cyclodextrin, methylated β-cyclodextrins, hydroxypropyl beta-cyclodextrin), chitosan, trimethyl chitosan, poly-l-arginine, l-lysine, chondroitinase ABC, 1-dodecylazacycloheptan-2-one, quillajasaponin.

Examples of commercial formulations identified by trade name and active agent include Ativan™ (lorazepam), Buprenex™ (buprenorphine), Cardilate™ (nitroglycerine), Ergostat™ (ergotamine tartrate), Imdur™ (isosorbide mononitrate), Nicorette™ (nicotine), Testred™ (methyl testosterone); bioadhesive tablets including Bonjela™ (choline salicylate), Corsodyl™ (chlorhexidine), and Taktarin™ (miconazole); Buccal mucosa formulations including Aftach™ (triamcinolone acetonide), Buccastem™ (prochlorperazine maleate), and Suscard™ (glycerin trinitrate); and Bucaal sprays including Ambien™ (zolpidem tartrate), Imitrex™ (sumatriptan succinate), and Sativex™ (Nabiximols-1:1 THC:CBD). It is contemplated that a D1/D5 receptor antagonist described herein, including ecopipam, can be formulated in the same or similar manners.

A dosage form according to the disclosure herein can be designed for controlled release, including sustained release, extended release, and prolonged release. In embodiments, a pharmaceutical dosage form for intraoral absorption of ecopipam is designed for immediate release and intraoral absorption. It has advantageously been found that first pass metabolism can be avoided or significantly reduced with such formulations.

Amounts and Dosing

The amount of a D1/D5 receptor antagonist described herein, including ecopipam, in a dosage form according to the disclosure herein can be relatively small, e.g. less than 5 wt. %, or less than 2 wt. %, or less than 1 wt. % or less than 0.5 wt. %, for example in a range of 0.0001 wt. % to 5 wt. %, or 0.001 wt. % to 2 wt. %, 0.001 wt. % to 1 wt. %.

In embodiments, the API is ecopipam and the dosage form includes about 1 mg to about 200 mg, about 5 mg to about 100 mg, about 50 mg to about 90 mg, or any values therebetween of ecopipam or a pharmaceutically acceptable salt thereof. For example, the dosage form can include about 200 mg or less, 100 mg or less, 50 mg or less, or 10 mg or less of ecopipam or a pharmaceutically acceptable salt thereof. For example, the dosage form can include about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg or any values therebetween or ranges defined by such values of ecopipam or pharmaceutically acceptable salt thereof.

For example, the dosage forms including ecopipam or pharmaceutically acceptable salt thereof can include the ecopipam or pharmaceutically acceptable salt thereof in an amount of 1 wt % to about 40 wt %, about 10 wt % to 20 wt %, about 15 wt % to 30 wt %, about 1 wt % to about 10 wt %, about 5 wt % to about 15 wt % or any values therebetween.

The pharmaceutical dosage forms in accordance with the disclosure may allow for administration of reduced total dosing amounts, while maintaining efficacy of dosage form as compared to an oral dosage form for oral systemic administration. For example, the dosage forms in accordance with the disclosure can provide for 5% or more, 10% or more, or 20% or more, or 25% or more, or 50% or more, or 75% or more reduction in the total daily dosing amounts as compared an oral dosage form for oral systemic administration, while maintaining the same efficacy as the oral dosage form for oral systemic administration.

In any of the aspects of the disclosure, the pharmaceutical dosage form can be administered in one or more doses. The pharmaceutical dosage forms of the disclosure can be administered using an initial dose titration schedule or without an initial dose titration schedule.

In any of the aspects of the disclosure, the pharmaceutical dosage form of the disclosure can be administered to a subject in need thereof to achieve a total daily dose of ecopipam or pharmaceutically acceptable salt thereof of about 1 mg to about 200 mg, or about 5 mg to about 100 mg. For example, a subject in need thereof can be administered the pharmaceutical dosage form to achieve a total daily dosage of ecopipam or pharmaceutically acceptable salt thereof of 200 mg or less, 179.3 mg or less, 125 mg or less, 89.6 mg or less, 44.2 mg or less. For example, the total daily dose of ecopipam or pharmaceutically acceptable salt thereof can be about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 mg or any values therebetween or ranges defined by such values. In any of the aspects of the disclosure, the pharmaceutical dosage form of the disclosure can be administered to a subject in need thereof to achieve a total daily dosage of ecopipam of pharmaceutically acceptable salt thereof in an amount of less than 2 mg/kg, 1.5 mg/kg or less, 1 mg/kg or less, 0.5 mg/kg or less, or any values therebetween. For example, the total weight based daily dosing of ecopipam can be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 or less than 2 mg/kg or any values therebetween or ranges defined by such values.

Co-Administration

The dosage forms described herein, including one including ecopipam or a salt thereof, can be administered with a UGT inhibitor, or on a dosing schedule that overlaps a dosing schedule of a UGT inhibitor schedule. The dosage forms described herein can be administered at the same dose amounts and schedules described above. Ecopipam is glucuronidated in the gastrointestinal tract and in the liver, and concomitant administration of oral ecopipam with general UGT inhibitors increases bioavailability of ecopipam by 50.8%. For this drug interaction, the increase in bioavailability due to general UGT inhibition in the GI tract after oral systemic administration would not be observed upon administration according to the dosage forms and methods described herein. Examples of UGT inhibitors are in the table below.

| UGT Isoform | Inhibitor |
|---|---|
| UGT1A1 | Silybin, atazanavir |
| UGT1A3 | Ritonavir, Quinidine |
| UGT1A4 | Diclofenac, Probenecid |
| UGT1A6 | Diclofenac |
| UGT1A9 | Diclofenac, Mycophenolic, acid Mefenamic acid |
| UGT2B7 | Diclofenac, Quinidine, Probenecid |
| UGT2B15 | Probenecid |

Surprisingly it has been found that the dosage forms described herein including ecopipam or pharmaceutically acceptable salt thereof can be administered with a CYP3A4/5 inducer and/or with a CYP3A4/5 inhibitor, or on a dosing schedule that overlaps a dosing schedule of a CYP3A4/5 inducer. As detailed below, oral dosage forms (for oral systemic administration) of ecopipam were found to have adverse drug-drug interactions with CYP3A4 inducers co-administration was not advised. The pharmaceutical dosage forms for intraoral ecopipam advantageously avoid first pass metabolism, which results in glucuronide metabolites. Metabolism in the gastrointestinal tract to metabolites was identified as a source of the adverse drug-drug interaction. Thus, the ability of the intraorally absorbed formulation to reduce or avoid such metabolism was beneficially found to allow for co-administration with the CYP3A4 inducers.

CYP3A4 inducers include, for example, Apalutamide, Mitotane, Avasimibe, Rifampin, Enzalutamide, Rifapentine, Ivosidenib, St John's Wort extract, and Lumacaftor.

The dosage forms described herein, including one including ecopipam or a salt thereof, can be administered with a p-glycoprotein (PGP) inhibitor, or on a dosing schedule that overlaps a dosing schedule of a PGP inhibitor schedule. The dosage forms described herein, including one including ecopipam or a salt thereof, can be administered with a CYP3A4/5 inhibitor, or on a dosing schedule that overlaps a dosing schedule of a CYP3A4/5 inhibitor schedule.

PGP inhibitors include (for example) verapamil, cyclosporin A, reserpine, quinidine, yohimbine, tamoxifen and toremifene, dexverapamil, dexniguldipine, valspodar, and dofequidar fumarate, cyclopropyldibenzosuberane zosuquidar, laniquidar, mitotane, biricodar, elacridar, ONT-093, tariquidar, and HM30181.

CYP3A4 inhibitors include weak inhibitors, e.g. cimetidine; moderate inhibitors, e.g. amiodarone, erythromycin, fluconazole, miconazole, diltiazem, verapamil, delavirdine, amprenavir, fosamprenavir, conivaptan; and strong inhibitors, e.g. clarithromycin, telithromycin, nefazodone, itraconazole, ketoconazole, atazanavir, darunavir, indinavir, lopinavir, nelfinavir, ritonavir, saquinavir, tipranavir.

CYP3A5 inhibitors include (for example) ketoconazole, erythromycin, nefazodone, itraconazole, clarithromycin, and mibefradil.

Diseases

The dosage form can be for the treatment of a patient in need thereof, or a patient in need of a dopamine D1 antagonist, or a patient in need of a dopamine D1/D5 antagonist. A dosage form disclosed herein containing ecopipam can be for the treatment of a patient in need of a selective dopamine D1 antagonist. A dosage form described herein, including one containing ecopipam, can be for the treatment of a tic disorder or movement disorder. The tic disorder can be Tourette Syndrome, a pediatric autoimmune disorder associated with streptococcal infection (PANDAS), a transient tic disorder, a chronic tic disorder, or a Tic Disorder Not Otherwise Specified (NOS). The subject can exhibit a motor tic (e.g., a complex motor tic), a vocal tic (e.g., a complex vocal tic), or a combination thereof. A dosage form described herein, including one containing ecopipam, can be for the treatment of Childhood Onset Fluency Disorder (stuttering). A dosage form described herein, including one containing ecopipam, can be for the treatment of Restless Legs Syndrome, refractory Restless Leg Syndrome, Restless Legs Syndrome with Augmentation, or for Augmentation associated with Restless Legs Syndrome. A dosage form described herein, including one containing ecopipam, can be for the treatment of obesity, including type 2 diabetic subjects.

The dosage forms disclosed herein are generally and variously useful for treatment of fluency disorders, including stuttering, which is also variously referred to as stammering. The dosage forms disclosed herein can also be administered for the treatment of stuttering induced as a side effect of a medication; stuttering associated with autism; and stuttering as a result of another disease or condition, such as a sporadic, genetic, or neurodegenerative disorder.

In other embodiments, the dosage forms disclosed herein are useful in the treatment of speech and language disorders including expressive language disorder, mixed receptive-expressive language disorder, phonological disorder, and communication disorder not-otherwise-specified (DSM-IV). In any given disorder, there may be impaired production of fluent and comprehensible speech, a phonological disorder, or developmental verbal dyspraxia, in which the coordination and motor control of the speech organs is compromised, or problems with morphology, syntax, semantics, or pragmatics. The term specific language impairment (SLI) is often used as an umbrella term for expressive language disorder, mixed receptive-expressive language disorder, and sometimes phonological disorder. The dosage forms disclosed herein can be used to alleviate these disorders.

The dosage forms disclosed herein are contemplated to be useful in treatment of mental disorders including psychoses, schizophrenia or depression in a mammal, or for the control of pain or anxiety in a mammal, or for the control of pain or anxiety in a mammal.

A sublingual dosage form and/or a buccal dosage form could lend themselves for acute treatment of these ailments, especially stuttering and Tourette's syndrome.

Certain D1/D5 receptor antagonist APIs disclosed herein are also active as renal vasodilators. Dosage forms disclosed herein containing one or more of these compounds can thus be used in methods for controlling hypertension by administering to a mammal a renal vasodilating effective amount of such a compound in a dosage form described herein, and/or according to a method described herein.

EXAMPLES

The following examples are provided for illustration and are not intended to limit the scope of the invention.

Example 1: pH Effect on BCS Solubility of Ecopipam

BCS solubility of Ecopipam HCl (EBS-101) was performed in five different pH buffers ranging from pH 1.2 to pH 6.8 and three bio-relevant media at 37° C. for up to 24 hours. Results demonstrated that the solubility of Ecopipam HCl (EBS-101) was pH-dependent, solubility increased from pH 1.2 to pH 3.0 buffers and reached the highest solubility in pH 3.0 citrate buffer (9.4 mg/mL), then solubility decreased from pH 4.5 to pH 6.8 buffers due to crystalline form change. In bio-relevant media, Ecopipam HCl (EBS-101) exhibited the highest solubility in FaSSGF (2.0 mg/mL), followed by moderate solubility in FeSSIF-V2 (0.66 mg/mL) and the lowest solubility in FaSSIF-V2 (0.05 mg/mL), and crystalline form after solubility test also changed in FaSSIF-V2 and FeSSIF-V2. In pH buffers, it was observed to be substantially stable in the five pH buffers (pH 1.2, pH 3.0, pH 4.5, pH 5.5 and pH 6.8) at 37° C. for up to 24 hours, while in bio-relevant media, it was only stable at 37° C. for up to 1 hour, as degradation occurred from 3 hours. The results are shown in the table below. Solubility and final pH were the average of three parallel values. Purity was that of 24 hours. N/A means not performed.

| Media | Solubility (mg/mL) | Final pH | Purity (%) | Appearance | XRPD |
|---|---|---|---|---|---|
| pH 1.2 HCl buffer, 50 mM | 1.56 | 1.23 | 99.87 | White suspension | No change |
| pH 3.0 citrate buffer, 100 mM | 9.42 | 2.96 | 99.87 | White suspension | No change |
| pH 3.0 phthalate buffer, 50 mM | 0.008 | 3.05 | | White suspension | Changed |
| pH 4.5 acetate buffer, 50 mM | 3.30 | 4.50 | 99.85 | White suspension | Changed |
| pH 5.5 acetate buffer, 50 mM | 0.23 | 5.49 | 100.00 | White suspension | Changed |
| pH 6.8 phosphate buffer, 50 mM | 0.02 | 6.85 | 100.00 | White suspension | Changed |
| FaSSGF | 2.02 | 1.61 | N/A | Hazy solution | No change |
| FaSSIF-V2 | 0.05 | 6.49 | N/A | White suspension | Changed |
| FeSSIF-V2 | 0.66 | 5.84 | N/A | White suspension | Changed |

Figure 2:
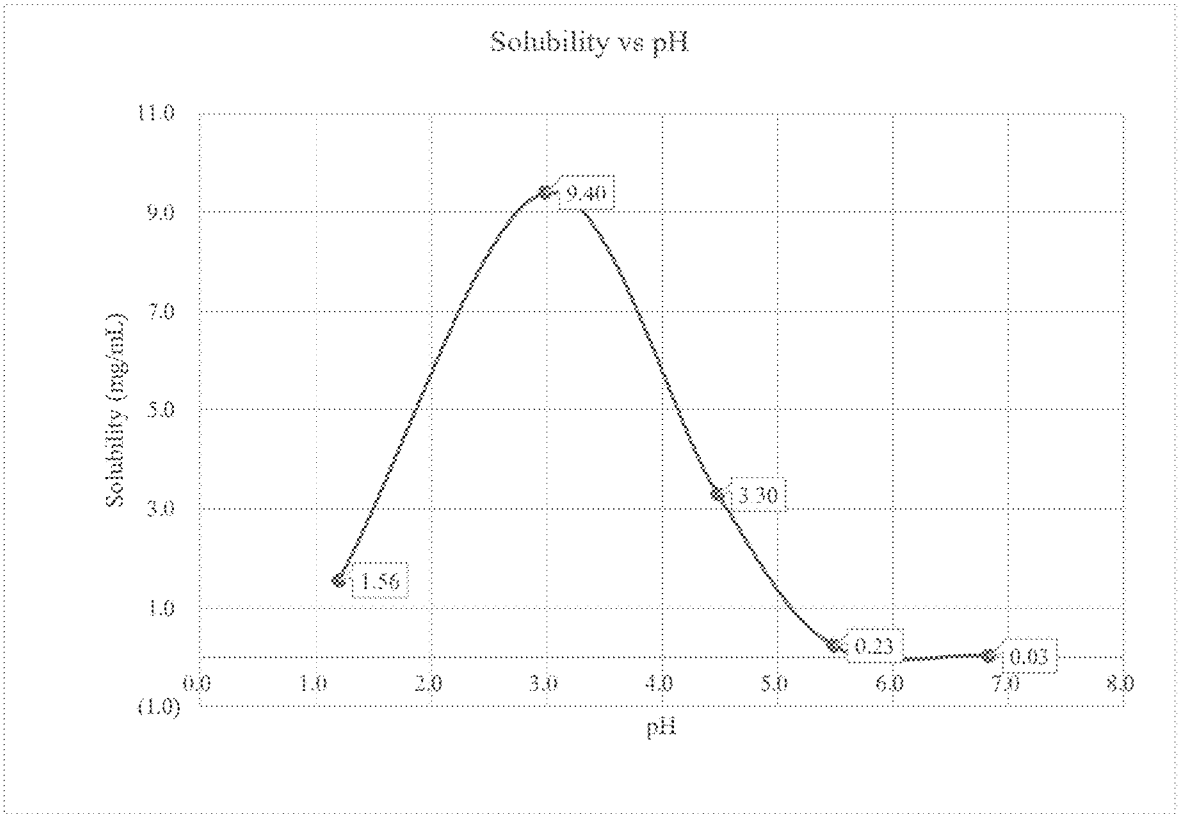
FIG. 2 is a graph showing the effect of pH on solubility for ecopipam HCl.
Figure 3:
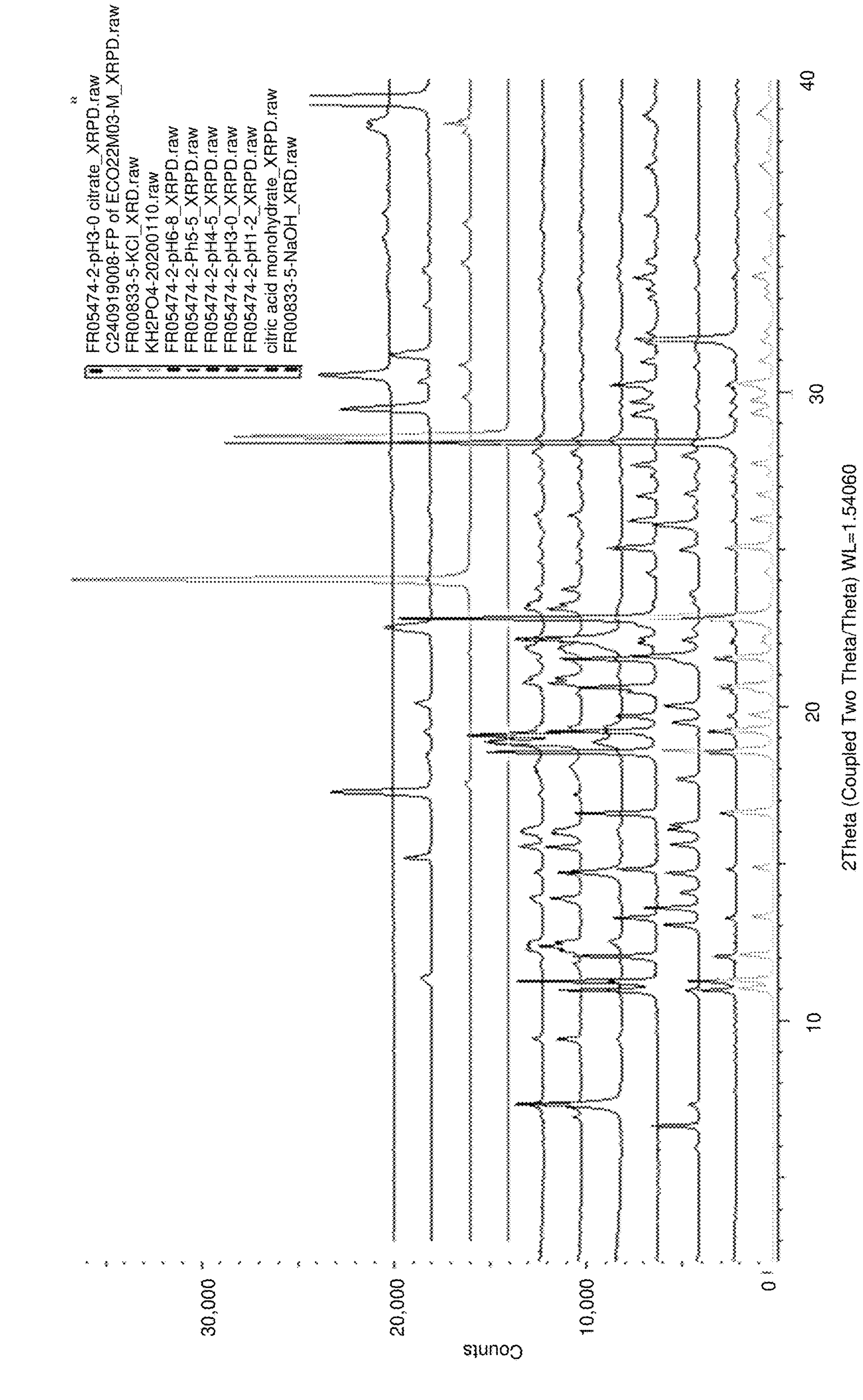
FIG. 3 is a an XRPD overlay of Ecopipam HCl (EBS-101_after solubility test in pH buffers.

FIG. 2 illustrates the trend of solubility for Ecopipam HCl (EBS-101) in the various pH buffers. It was surprisingly found that Ecopipiam HCl had significantly improved solubility in a citrate buffer at a pH of 3.05. Referring to FIG. 3, it was also observed that the Ecopipam HCl did not exhibit a change in crystallinity in citrate buffer.

Example 2: Modeling of Intraoral Absorption of Ecopipam

Figure 4:
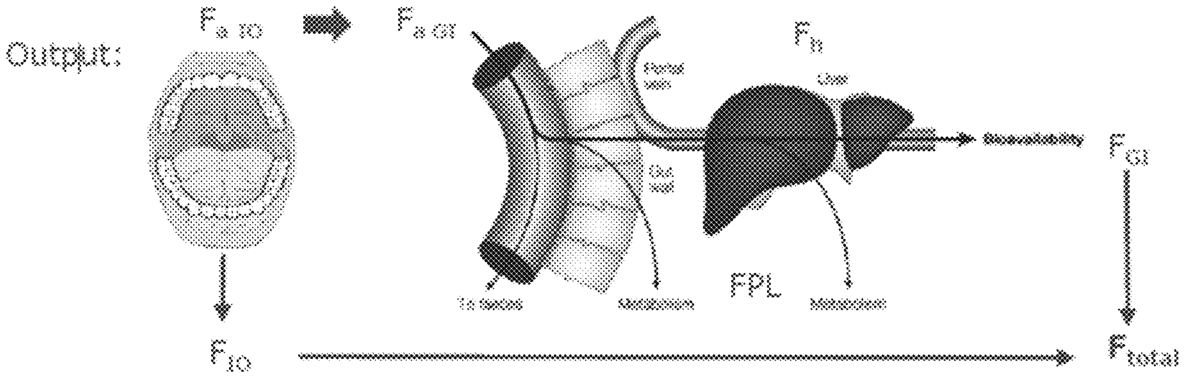
FIG. 4 is a schematic showing the absorption profiles simulated.

The intraoral absorption of ecopipam was modeled using physiologically-based pharmacokinetics (PBPK) (GastroPlus®). FIG. 4 illustrates absorption profiles simulated. The following input parameters were used in the simulation:

| Parameter | Value |
|---|---|
| logP | 4.31 |
| pKa | 8.68 (a) and 7.25 (b) |
| Particle size $D_{50}$ (μm) | 2 |
| Intraoral residence time (min) | 0.5 |
| Diffusivity (×$10^{-7}$ $cm^2$/s) | 11.2 |
| Fraction unbound in oral mucosa $F_{ut}$ | 0.06 |

The predicted intraoral fraction absorbed for ecopipam was calculated to be 23% after administration of a 20 mg orally dissolvable tablet formulation with small particle size (2 μm) comprising ecopipam HCl. This represents a significant absorption amount. This significant amount of absorption achievable intraorally with the formulations of the disclosure combined with the avoidance of first-pass metabolism results in significant and beneficial influence on the total exposure.

Figure 5A:
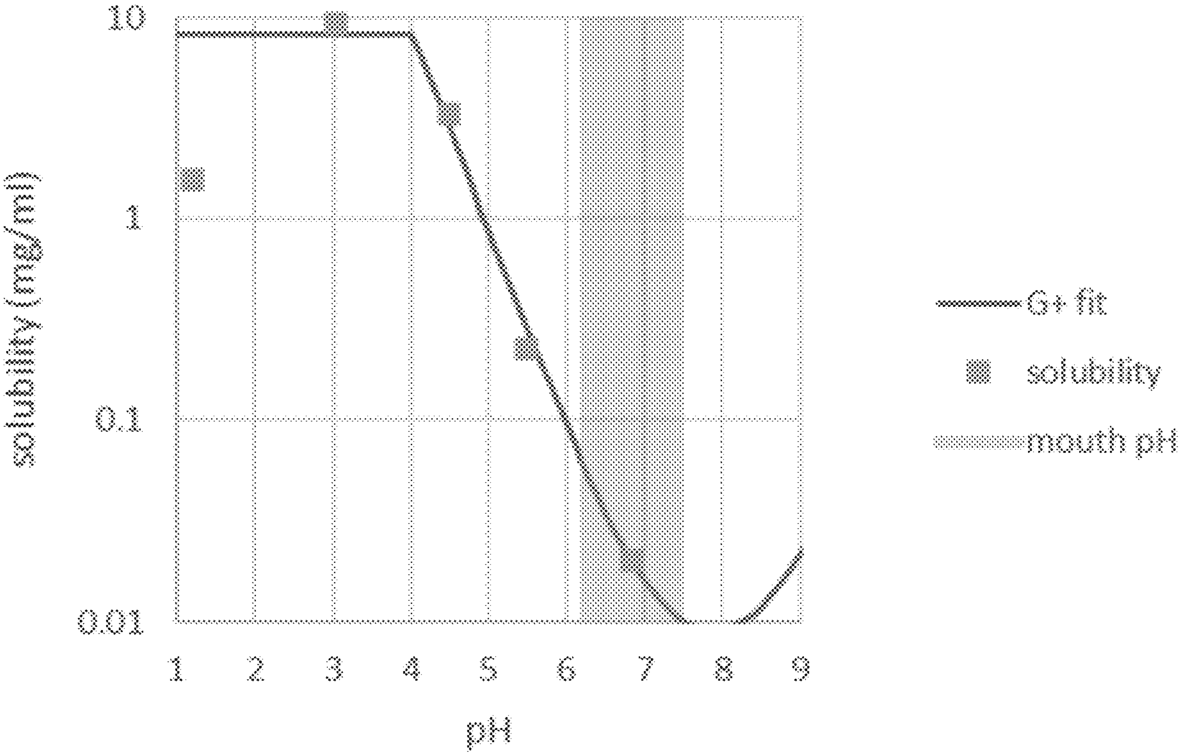
FIG. 5A is a graph showing predicted solubility of ecopipam HCl as a function of pH.
Figure 5B:
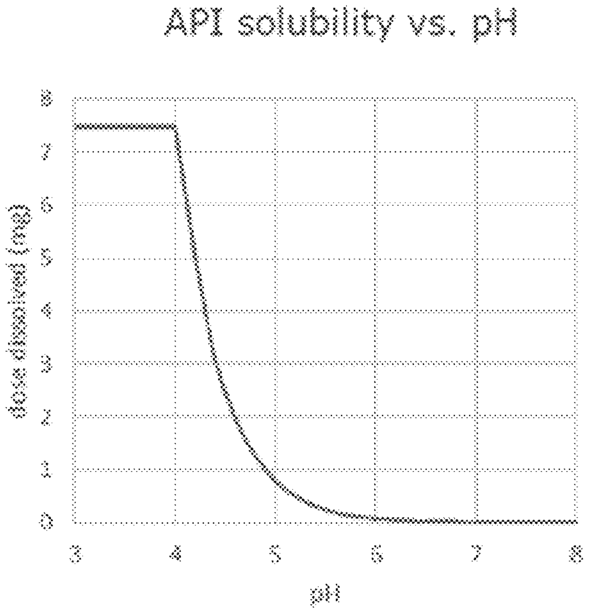
FIG. 5B is a graph showing Ecopipam HCl solubility as a function of pH.
Figure 5C:
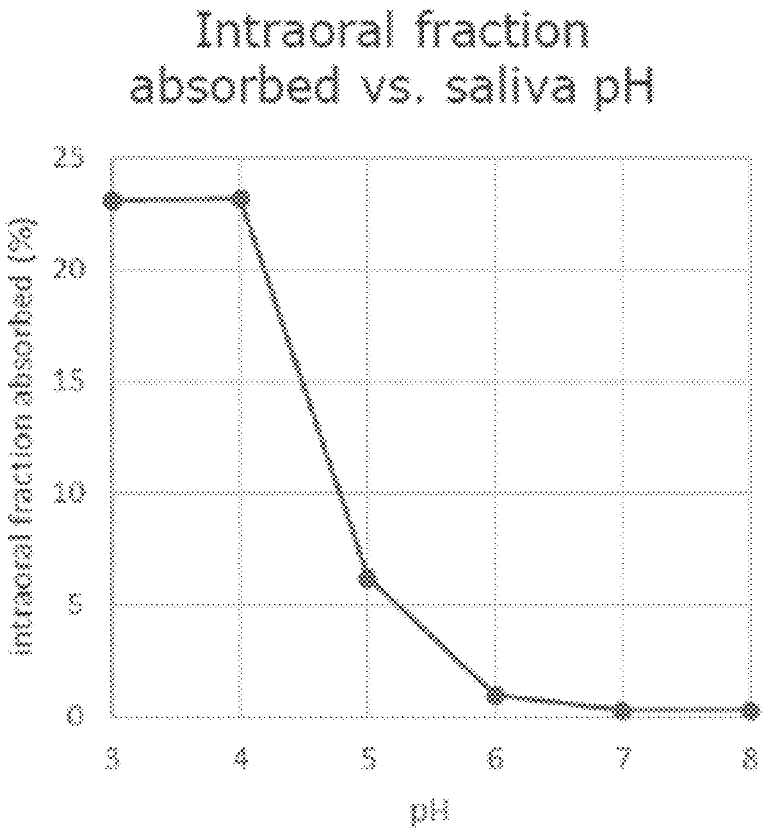
FIG. 5C is a graph showing intraoral fraction absorption percentage as a function of saliva pH.

Referring to FIGS. 5A to 5C, solubility of ecopipam, HCl at different pH was also examined through the model. It was observed that solubility of ecopipam HCl drops significantly at the natural pH of the mouth. The model predicted the best intraoral absorption of ecopipam to be at a saliva pH of 4 or lower.

Figure 6:
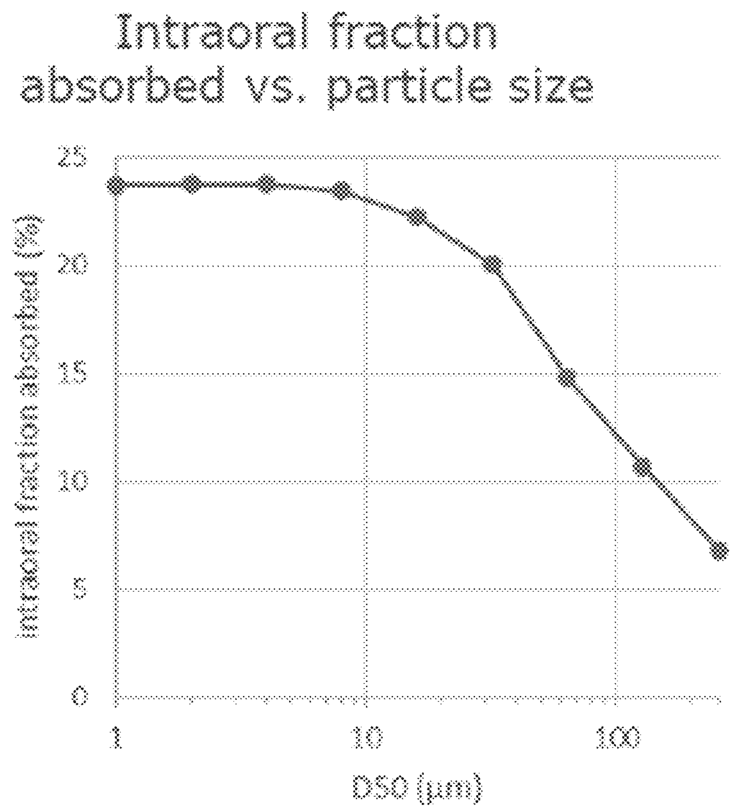
FIG. 6 is a graph showing intraoral fraction absorption percentage as a function of D50 particle size of the formulation.

Referring to FIG. 6, the particle size of the formulation was also found to affect intraoral absorption. In FIG. 6, a 22.4 mg dose was analyzed by the model and an average D50 particle size of 10 μm or lower were found to be beneficial to improve intraoral fraction absorption.

Example 3: Analysis of First Pass Metabolites After Oral Administration of Ecopipam A Phase 1, Open-label Study of the Absorption, Metabolism, and Excretion of [$^{14}$C]-Ecopipam Following a Single Oral Capsule Dose in Healthy Male Subjects Healthy subjects of any ethnic origin, aged between 35 and 55 years, inclusive, with a body mass index between 18.0 and 30.0 kg/$m^2$, inclusive, were selected for the study. Eight subjects were enrolled and dosed, and all 8 subjects completed the study as planned.

A single oral dose of [$^{14}$C]-ecopipam HCl containing approximately 88.5 μCi of [$^{14}$C] radioactivity was administered to subjects orally as a powder-filled capsule in the fasted state.

Following a single oral dose of 200 mg [$^{14}$C]-ecopipam HCl, the arithmetic mean total radioactivity recovery in urine and feces was 91.6%. Renal excretion of metabolites was the principal route of elimination of [$^{14}$C]-ecopipam, with an arithmetic mean of 83.3% of radioactivity recovered in urine and 8.27% of radioactivity recovered in feces.

The median time of the maximum observed concentration of ecopipam in plasma, total radioactivity in plasma, and total radioactivity in whole blood were similar at 2.00, 2.25, and 2.00 hours postdose, respectively. Appearance of the EBS-101-40853 metabolite in plasma peaked at 3.50 hours postdose.

The geometric mean apparent terminal elimination half-life (t½) of ecopipam and EBS-101-40853 were 17.3 and 25.6 hours, respectively. The geometric mean t½ for total radioactivity in plasma and whole blood were longer than ecopipam and EBS-101-40853, at 94.1 and 122 hours, respectively, indicating the presence of other persistent circulating metabolites.

The geometric mean area under the concentration-time curve (AUC) ratio of plasma ecopipam or EBS-101-40853 to plasma total radioactivity was 0.0169 and 0.00178, respectively, suggesting neither ecopipam nor EBS-101-40853 were the primary drug-related material in systemic circulation. Instead, ecopipam O-β-D-glucuronide was the major drug-related material in systemic circulation, accounting for 80% of radioactivity in plasma.

There was no preferential association of radioactivity with red blood cells based on the geometric mean AUC ratio of whole blood to plasma total radioactivity of 0.666.

The geometric mean percentage of dose excreted in urine as ecopipam and EBS-101-40853 was 0.115% and 0.0645%, respectively, corresponding to geometric mean renal clearance of 0.284 and 1.53 L/hour, respectively, which were lower than the typical glomerular filtration rate in the kidney.

The primary route of biotransformation of ecopipam was by glucuronidation to form ecopipam O-β-D-glucuronide, which is then excreted renally (accounting for 67% of radioactivity in the urine) along with other minor metabolites. EBS-101-40853 AUC from time zero extrapolated to infinity (AUC0-inf) accounted for 10.5% of ecopipam AUC0-inf. The main component in the feces was unchanged ecopipam, accounting for 6% of the total administered dose.

The estimated AUC of the metabolites associated with the trailing terminal phase accounts for 39.4% of the overall plasma total radioactivity AUC0-inf and triggered the post-hoc pooled metabolites analysis.

Most of the radioactivity in plasma (~80%) was accounted for by ecopipam glucuronide, with 2.66% of the radioactivity identified as ecopipam, 0.26% identified as EBS-101-40853, and 3.09% identified as EBS-101-40853 glucuronide. There were 3 peaks of unidentified metabolites in plasma: P3 representing 2.27%, P4 representing 2.82%, and P5 (EBS-101-40853 sulfate) representing 8.62%.

The $t_{1/2}$ for metabolites P3 (97.4 hours) and P5 (EBS-101-40853 sulfate; 122 hours) corrected for extraction efficiency from pooled PK samples closely resembled that observed in plasma total radioactivity (94.1 hours), indicating these are the persistent circulating metabolites accounting for the terminal phase of radioactivity. The estimated fractions of AUC0-inf values (equivalent to predicted AUC from time 0 to end of the dosing interval at steady state) for the corrected P3, P4, and P5 metabolites relative to plasma total radioactivity were 0.0462, 0.00243, and 0.0603, respectively, indicating none of these metabolites accounted for >10% of the total radioactivity in plasma.

Example 4: Mass Balance Study of Ecopipam

Referring to FIG. 1, a mass balance study of ecopipam along with in vitro studies showed the metabolic pathways for elimination of Ecopipam (FIG. 1). Ecopipam is primarily metabolized by UGT1A9 to Ecopipam glucuronide (which accounted for ~80% of radioactivity in plasma and 67% of radioactivity in the urine). In addition, Ecopipam is metabolized by CYP3A4 to form EBS-101-40853, which accounted for 10.5% of ecopipam's area under the curve $AUC_{\infty}$. There were several minor metabolites, which all account for less than 10% of the radioactivity, and were therefore, not important.

After steady-state dosing with ecopipam 1.8 mg/kg using the proposed weight-based dosing paradigm, the predicted geometric mean $C_{max}$ (3968 [range: 1679-11731] ng/ml) and $AUC_{(0-\tau)}$ (29671 [range: 14981-55254] ng*h/mL) of ecopipam glucuronide was much higher than ecopipam. The $C_{max}$ (4.1 [range: 1.37-9.9] ng/ml) and AUC (0-1) (140 [range: 47.7-351] ng*h/mL) of EBS-101-40853 was much lower than ecopipam. After steady-state dosing with ecopipam, the predicted $C_{max}$ and AUC (0-1) of EBS-101-40853 glucuronide were 92.1 (32.7-180) ng/ml and 2074 (707-5747) ng*h/mL, respectively.

Weight-Based Ecopipam Dosing Regimen for Pediatric Patients with TD (Target Dose=~1.8 mg/kg/day)

| Weight (kg) | Dose (mg) Week #1 | Dose (mg) Week #2 | Dose (mg) Week #3 | Dose (mg) Week #4 onward |
|---|---|---|---|---|
| ≥18 to ≤23 | 11.2 [a] | 22.4 [b] | 33.6 [d] | 33.6 [d] |
| >23 to ≤34 | 11.2 [a] | 22.4 [b] | 33.6 [d] | 44.8 [c] |
| >34 to ≤44 | 11.2 [a] | 22.4 [b] | 44.8 [c] | 67.2 [e] |
| >44 to ≤68 | 22.4 [b] | 44.8 [c] | 67.2 [e] | 89.6 [f] |
| >68 to ≤83 | 22.4 [b] | 44.8 [c] | 89.6 [f] | 134.4 [g] |
| >83 | 22.4 [b] | 44.8 [c] | 89.6 [f] | 179.2 [h] |

HCl = hydrochloride;
TD = Tourette's disorder
[a] Equivalent to ecopipam HCl 12.5 mg
[b] Equivalent to ecopipam HCl 25 mg
[c] Equivalent to ecopipam HCl 50 mg
[d] Equivalent to ecopipam HCl 37.5 mg
[e] Equivalent to ecopipam HCl 75 mg
[f] Equivalent to ecopipam HCl 100 mg
[g] Equivalent to ecopipam HCl 150 mg
[h] Equivalent to ecopipam HCl 200 mg

Example 5: Formulations for Intraoral Absorption of Ecopipam

Formulations in accordance with the disclosure were prepared by incorporating ecopipam HCl into a formulation premix. Premixes which were gelatin and non-gelatin based were tested. It was observed in preparing batches 1 and 2 that the ecopipam did not disperse easily in the premix. For batches 3-5, the ecopipam was manually wetted prior to bulk premix addition. For batches 2, 4, and 5, the pH modifier was then added to the suspension of ecopipam HCl in the premix to adjust the pH to a target pH of 3.30±0.2. The suspension was then filled into tablet molds and freezing was performed at −70° C. for 4 minutes. The samples were held at −15° C. or less for a minimum of 12 hours. The samples were then freeze dried at 0° C. for 12 hours to thereby produce the formulations in accordance with the disclosure in the form of a sublingual orally disintegrating tablet.

Sublingual Orally Disintegration Formulations

| | Amount of component (% w/w) | | | | |
|---|---|---|---|---|---|
| Component | Batch 1 | Batch 2 | Batch 3 | Batch 4 | Batch 5 |
| Ecopipam HCl (free base equivalent) | 8.37 (7.47) | 8.37 (7.47) | 8.37 (7.47) | 8.37 (7.47) | 8.37 (7.47) |
| Bovine Gelatin | 4.00 | 4.00 | 4.00 | 4.00 | N/A |
| Pullulan Polysaccharide | N/A | N/A | N/A | N/A | 4.00 |
| Mannitol | 3.00 | 3.00 | 3.00 | 3.00 | 3.00 |
| Citric Acid Anhydrous | N/A | 0.52 | N/A | 0.64 | 0.03 |
| Purified Water | 84.63 | 84.10 | 88.82 | 88.18 | 84.60 |
| Total | 100 | 100 | 100 | 100 | 100 |
| Dose Strength (mg) | 22.4 | 22.4 | 22.4 | 22.4 | 22.4 |
| Wet fill (mg) | 300.00 | 300.00 | 600.00 | 600.00 | 300.00 |

The pH of the suspension was tested after mixing and then again 24 hours post mixing. Batches 1 and 3 did not include the citric acid pH modifier. The pH when adjusted to the target remained stable when pH was adjusted by addition of the citric acid (batches 2, 4, 5). Batches 1 and 3, which were not adjusted for pH after mixing exhibited more pH variability 24 hours after mixing as compared to the pH adjusted samples.

pH Testing During Manufacturing Process

| Batch | Initial pH | Target pH | Adjusted pH | Citric Acid (w/w %) | pH at conclusion of mixing (SH0) | pH 24 hrs after conclusion of mixing (SH24) | Change SH0 − SH24 |
|---|---|---|---|---|---|---|---|
| 1 | — | — | — | — | 5.32 | 4.78 | −0.54 |
| 2 | 5.43 | 3.30 ± 0.20 | 3.50 | 0.52 | 3.48 | 3.52 | +0.04 |
| 3 | — | — | — | — | 5.29 | 5.42 | +0.13 |
| 4 | 5.40 | 3.30 ± 0.20 | 3.33 | 0.64 | 3.31 | 3.37 | +0.06 |
| 5 | 4.38 | 3.30 ± 0.20 | 3.01 | 0.03 | 3.03 | 3.05 | +0.02 |

Example 6: Pharmacokinetic Properties of Formulations for Intraoral Absorption of Ecopipam Pharmacokinetic properties of the pharmaceutical formulations in accordance with the disclosure, which provide for intraoral absorption of ecopipam was studied in a Naïve minipigs animal model. The minipigs were 4-5 months old with a weight range within 10-15 kg at dosing. 3 male animals were used. The minipigs were dosed with an ecopipam HCl oral tablet (Ecopipam HCl IR Tablet) on day 1, and separately an ecopipam HCl sublingual tablet (Ecopipam HCl Zydis ODT tablet), which disintegrates intraorally, on day 8. The minipigs were observed for 10 days. Ecopipam HCl Zydis ODT tablet had the formulation as identified in Batch 4 in Example 5.

| Group | 1 | 1 |
|---|---|---|
| API | Ecopipam HCl | Ecopipam HCl |
| Dose route | Oral (tablet) | Sublingual (Tablet) |
| Dose level (mg/animal) | 50 mg ecopipam HCl (44.8 mg ecopipam free base) | 25 mg ecopipam HCl (22.4 mg ecopipam free base) |
| Animal Number | 1255, 1256, 1257 | 1255, 1256, 1257 |

On dosing days, the animals were fed 1 hour post dose and then offered a second feed in the afternoon. Prior to dosing and immediately after dosing, the pH level of the salvia were tested. The pH of the minipig saliva was found to remain unchanged after dosing with the oral tablet. By comparison, the sublingual tablet in accordance with the disclosure reduced the pH of the minipig saliva significantly. As shown in the table below, the pH of the saliva after dosing with the sublingual tablet was reduced dramatically by 1-3 units. The minipig salvia prior to dosing is 1 to 3 pH units higher than the saliva of a human. It is anticipated that the formulations of the disclosure will reduce the pH of human saliva after dosing to 6.5 or less, 5 or less, or even 4 or less, providing for improved solubility of ecopipam in the human mouth.

| Animal Number | Dosing Occasion | Pre-dose Saliva pH level | Post-dose Saliva pH level |
|---|---|---|---|
| Ecopipam IR Tablet | | | |
| 1255 | 1 | 9 | 9 |
| 1256 | 1 | 9 | 9 |
| 1257 | 1 | 9 | 9 |
| Ecopipam Zydis ODT Tablet | | | |
| 1255 | 2 | 8 | 5 |
| 1256 | 2 | 8 | 7 |
| 1257 | 2 | 9 | 6 |

The minipigs were also observed for central nervous system (CNS) activity. Clinical observations indicate a more pronounced CNS effect after dosing with the sublingual tablet as compared to the orally administered tablet formulation, despite administering half of the dosing amount in the sublingual formulation.

| Animal No. | Days | Dose Administered | Observation |
|---|---|---|---|
| 1255 | 1 | Ecopipam IR Tablet | Decreased general activity |
| | 2-7 | NONE | Normal - no remarkable observation |
| | 8 | Ecopipam Zydis ODT Tablet | Decreased general activity, whole body tremor |
| | 9-10 | NONE | Normal - no remarkable observation |
| 1256 | 1 | Ecopipam IR Tablet | Decreased general activity |
| | 2-7 | NONE | Normal - no remarkable observation |
| | 8 | Ecopipam Zydis ODT Tablet | Decreased general activity, whole body tremor |
| | 9-10 | NONE | Normal - no remarkable observation |

-continued

| Animal No. | Days | Dose Administered | Observation |
|---|---|---|---|
| 1256 | 1 | Ecopipam IR Tablet | Decreased general activity |
| | 2-7 | NONE | Normal - no remarkable observation |
| | 8 | Ecopipam Zydis ODT Tablet | Decreased general activity, whole body tremor |
| | 9-10 | NONE | Normal - no remarkable observation |

Consistent with the clinical observations, concentration-time pharmacokinetic data indicated a more rapid and increased exposure to ecopipam after administration of the sublingual formulation as compared to the oral tablet. There was a dramatic decrease in the concentration of glucuronide metabolites observed after the sublingual formulation administration, as well.

The observance of CNS side effects demonstrates that ecopipam in a sublingual formulation has increased CNS availability as compared to the oral formulation. While CNS side effects are to be avoided in patients, this data is indicative of the improved efficacy of the sublingual formulation, which can result in reduced dosing amounts being needed for effective treatment of patients, particularly for acute use.

The reduction of glucuronide metabolites with the formulations of the disclosure can result in reduced side effects, such as those relating to cardiac safety concerns, as well as reduced potential drug-drug interactions.

The concentration-time data were normalized for differences in dose. The ratio of Cmax and AUC after SL:oral dosing is summarized below

| | Ecopipam | Ecopipam Glucuronide | EBS-101-40853 | EBS-101-40853 Glucuronide |
|---|---|---|---|---|
| Ratio of SL/oral Cmax | 2.83 | 0.24 | 0.45 | 0.24 |
| Ratio of SL/oral AUC | 0.73 | 0.15 | 0.52 | 0.4 |

The data demonstrates that the amount of ecopipam glucuronide metabolites is significantly reduced (76-85% reduction) after sublingual administration as compared to oral administration. There was also an observed reduction in other metabolites.

Example 7: Exposure Response Study for Efficacy in Tourette's Disorder

Figure 7:
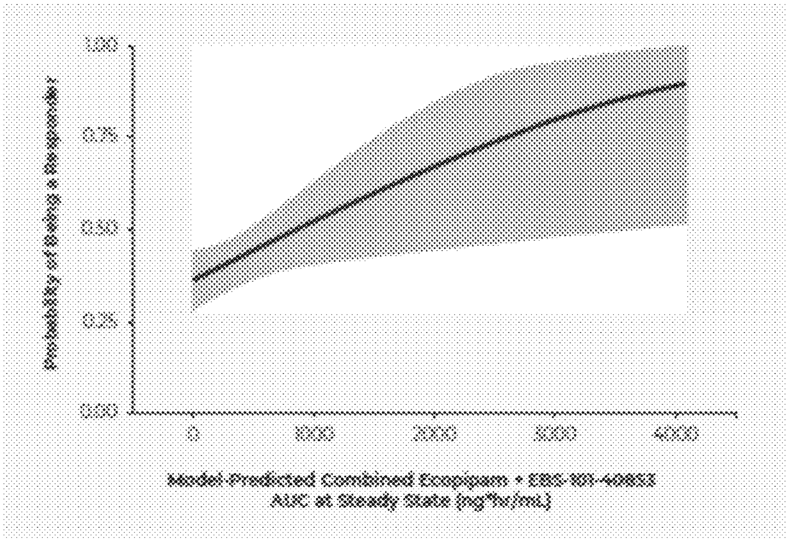
FIG. 7 is a graph showing the predicted probabilities and 90% confidence interval for exposure-response of efficacy on Tourette's Disorder.

A Phase 2 [Clinical Study] showed that there was an exposure-response for efficacy in Tourette's Disorder (TD). A logistic regression model showed that combined steady-state AUC (0-1) of ecopipam and EBS-101-40835 (assuming equipotence) was a predictor of being a responder at week 12 (FIG. 2). Based on this model, the odds of being a responder at 12 weeks increase by 6.8% for each 100 unit increase in the combined steady-state AUC (0-1) of ecopipam and EBS-101-40853 (Dumetrescu, 2023). FIG. 7 shows a plot of predicted probabilities and 90% confidence interval for exposure-response of efficacy in Tourette's Disorder.

Exposure-response analyses have been conducted for safety using sedation as an endpoint and cardiac safety (QTc). There was no relationship between plasma Cmax or $AUC_{inf}$ and the choice reaction time or visual analogue scale for sedation. There was an exposure-response relationship for QTc.

A randomized, double-blind, single dose, 4-way crossover thorough QT study was conducted with an open-label active control (EBS-101-HV-105, 2024). Subjects received single doses of ecopipam 179.2 mg, ecopipam 537.6 mg, moxifloxacin 400 mg, and placebo. There is no effect of ecopipam on HR, QRS, or PR intervals, but there is an increase in QTcF after a single dose of ecopipam 537.6 mg.

The primary endpoint for this study was pre-specified to be based on C-QT analysis using the methods outlined in the white paper (Garnett C, 2018) (Garnett C B. P., 2018). Models were developed for each single analyte including ecopipam, EBS-101-40853, ecopipam glucuronide, and EBS-101-40853 glucuronide and for 4 combination models (2 metabolites each). The best model appeared to be the model with ecopipam glucuronide and EBS-101-40853.

The most appropriate model describing the concentration-QT effects of ecopipam at increased doses and exposures was consistent with the nonclinical hERG data in vitro, which has been used as a surrogate for predicting QT prolongation. The hERG $IC_{50}$/free $C_{max}$ ratios for ecopipam and its main metabolites (indicative of the safety margins for predicting QT prolongation) were:

$$\text{Ecopipam} = 1166$$

$$EBS\text{-}101\text{-}40853 = 7303$$

$$\text{Ecopipam glucuronide} = 62 \text{ (lowest safety margin, and highest concentrations in human, and animal plasma)}$$

$$EBS\text{-}101\text{-}40853 \text{ glucuronide} = 652$$

The study showed that a 10 msec increase in ΔΔQTcF interval can be ruled out after a single ecopipam dose at the top end of the range for the therapeutic dose (ecopipam 179.2 mg) but cannot be ruled out after a single dose at the top end of the high clinical exposure (ecopipam 179.2 mg+a general UGT inhibitor) using the primary model. After steady-state dosing of ecopipam 1.8 mg/kg using the clinical weight-based dosing paradigm, a 10 msec increase in ΔΔQTcF can be ruled out using the primary model and all but one (EBS-101-40853 glucuronide alone) of the secondary models.

For the high clinical exposure (steady-state dosing of ecopipam 1.8 mg/kg with a general UGT inhibitor), a 10 msec increase can be ruled out by 5 of 8 models, including the primary model. The other 3 of 8 models, which could not rule out a 10 msec increase, resulted in an upper 90% confidence interval of 10.06 to 11.64 msec, which is not considered clinically relevant. At higher doses, there is the potential for increases in the ΔΔQTcF interval with up to 20.4 msec predicted after administration of a single dose of ecopipam 537.6 mg.

Example 8: Drug-Drug Interaction Studies

Ecopipam when administered orally is metabolized to ecopipam glucuronide by UGT1A9 and to EBS-101-40853 by CYP3A4 and both ecopipam and EBS-101-40853 are P-gp substrates. Two clinical studies were conducted to assess the resulting effects of UGT inhibition or CYP3A induction on the pharmacokinetics of ecopipam and its metabolites. One study evaluated whether a specific UGT1A9 inhibitor (mefenamic acid) or a general UGT inhibitor (divalproate sodium) affected the PK of ecopipam or its metabolites. The other study evaluated whether CYP3A4 induction influenced the PK of ecopipam and its metabolites. The results from these studies are summarized in Table 7 below along with clinical recommendations.

Clinical Studies Conducted to Evaluate the PK of Orally Administered Ecopipam and its Metabolites in the Presence and Absences of Specific Inducers and Inhibitors

| Concomitant Medication [Inducer/Inhibitor] (Study Number) | Results | Clinical Recommendations for oral systemically administered ecopipam |
|---|---|---|
| Rifampicin [strong inducer of CYP3A4 and P-gp, moderate inducer of CYP2C8, CYP2C9, and CYP2C19] (EBS-101-HV-106) | When rifampicin is co-administered with ecopipam, there was a substantially (72-77%) lower $C_{max}$ and $AUC_\infty$ of ecopipam, a substantially (71%) higher $C_{max}$ with no change in $AUC_\infty$ of EBS-101-40853, only a 22% lower $C_{max}$ and no change in $AUC_\infty$ of ecopipam glucuronide, and a more substantial impact on EBS-101-40853 glucuronide (with an increase of 2.8x in $C_{max}$ and 86% in $AUC_\infty$) | Co-administration of ecopipam with an inducer is not recommended. |
| Divalproate Sodium [General UGT Inhibitor] (EBS-101-HV-102) | When divalproate sodium was co-administered with ecopipam, there was a 40%-66% increases in $C_{max}$ of ecopipam and EBS-101-40853 and a 23% and 32% lower $C_{max}$ of ecopipam glucuronide and EBS-101-40853 glucuronide, a ~2.1x increase in $AUC_\infty$ of ecopipam, an ~86% increase in $AUC_\infty$ of EBS-101-40853 and no changes in the $AUC_\infty$ for the glucuronide conjugates | If ecopipam is administered concomitantly with general UGT inhibitors (e.g., VPA), the ecopipam dose should be decreased by 50%.. |
| Mefenamic Acid [Specific UGT1A9 Inhibitor] (EBS-101-HV-102) | When mefenamic acid was co-administered with ecopipam, there was a small increase (12-21%) in the $C_{max}$ of ecopipam and EBS-101-40853 and a 15% and 12% lower $C_{max}$ of ecopipam glucuronide and EBS-101-40853 glucuronide, a 42-45% increase in the $AUC_\infty$ of ecopipam and EBS-101-40853, no change in the $AUC_\infty$ of ecopipam glucuronide and a 14% increase in the $AUC_\infty$ of EBS-101-40853 glucuronide | If ecopipam is administered concomitantly with a UGT1A9 inhibitor (e.g., mefenamic acid), the ecopipam dose should be decreased by 50%. |

The intra-orally absorbing formulations in accordance with the disclosure can advantageously reduce such drug-drug interactions through bypass of the first pass metabolism.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

Aspects of the Disclosure

1. A pharmaceutical dosage form for use in delivering an active pharmaceutical agent (API) in a manner other than oral systemic delivery, wherein the API is selected from one or more of those in Table I, or 6,7,7a,8,9,13b-hexahydro-2-hydroxy-3-methoxy-7-methyl-5H-benzo[d]naphtho[2,1-b]azepine;

6,7,7a,8,9,13b-hexahydro-2-hydroxy-7-methyl-5H-benzo[d]naphtho[2,1-b]azepine;

6,7,7a,8,9,13b-hexahydro-3-chloro-2-hydroxy-7-methyl-5H-benzo[d]naphtho[2,1-b]azepine;

6,7,7a,8,9,13b-hexahydro-2-hydroxy-3,7-dimethyl-5H-benzo[d]naphtho[2,1-b]azepine;

6,7,7a,8,9,13b-hexahydro-2-amino-7-methyl-5H-benzo[d]naphtho[2,1-b]azepine;

6,7,7a,8,9,13b-hexahydro-2-amino-3-chloro-7-methyl-5H-benzo[d]naphtho[2,1-b]azepine;

6,7,7a,8,9,13b-hexahydro-2-amino-3,7-dimethyl-5H-benzo[d]naphtho[2,1-b]azepine;

6,6a,7,8,9,13b-hexahydro-12-methoxy-7-methyl[1]benzopyrano[4,3-a][3]benzazepine;

6,6a,7,8,9,13b-hexahydro-7-methyl[1]benzopyrano[4,3-a][3]benzazepin-12-ol;

6,6a, 7,8,9,13b-hexahydro-3-hydroxy-2-methoxy-7-methyl-5H-benzo[d]naphtho[2,1-b]azepine;

2-hydroxy-3-methoxy-7-methyl-5,6,7,7a,8,9,10,14b-octahydro-benzo[d]benzo[3,4] cyclo-hepta[1,2-b]azepine;

3-hydroxy-2-methoxy-7-methyl-5,6,7,7a,8,9,10,14b-octahydro-benzo[d]benzo[3,4] cyclo-hepta[1,2-b]azepine;

5,6,7,7a,8,12b-hexahydro-2-hydroxy-3-chloro-7-methyl-benz[d]indeno[2,1-b]azepine;

5,6,7,7a,8,12b-hexahydro-2-hydroxy-3-methoxy-7-methyl-benz[d]indeno[2,1-b]azepine;

5,6,7,7a,8,12b-hexahydro-2-amino-3-chloro-7-methyl-benz[d]indeno[2,1-b]azepine;

5,6,7,7a,8,12b-hexahydro-2-hydroxy-7-methyl-benz[d]indeno[2,1-b]azepine;

5,6,7,7a,8,12b-hexahydro-3,7-dimethyl-2-hydroxy-benz[d]indeno[2,1-b]azepine;

5,6,7,7a,8,12b-hexahydro-3-chloro-7-cyclopropylmethyl-2-hydroxy-benz[d]indeno[2,1b]azepine;

5,6,7,7a,8,12b-hexahydro-7-allyl-3-chloro-2-hydroxy-benz[d]indeno[2,1-b]azepine;

5,6,7,7a,8,12b-hexahydro-3-chloro-2-hydroxy-7,8,8-trimethyl-benz[d]indeno[2,1-b]azepine;

5,6,7,7a,8,11b-hexahydro-3-chloro-7-methylthieno[2',3':4,5]cyclopenta[1,2-a][3]benzazepine-2-ol;

5,6,7,7a,8,12b-hexahydro-2-hydroxy-3-chloro-benz[d]indeno[2,1-b]azepine;

6,7,7a,8,9,13b-hexahydro-3-chloro-2-hydroxy-5H-benzo[d]naphtho[2,1-b]azepine;

or 6,7,7a,8,9,13b-hexahydro-2-amino-3-trifluoromethyl-7-methyl-5H-benzo[d]naphtho[2,1b]azepine;

or SCH23390 and compounds related thereto, including SCH 12679 and the compounds described in U.S. Pat. No. 4,477,378 (which is hereby incorporated by reference in the present application in its entirety), BTS-73-947, NNC-22-0010, JHS-271, JHS-198, JHS-136, A69024, and NNC687. D1/D5 partial agonists include SKF38393, fenoldapam; SKF75670A; SKF 81297; SKF82958; or dinapsoline; or

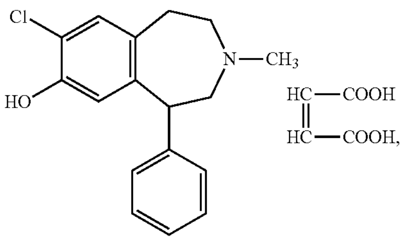

SCH 23390

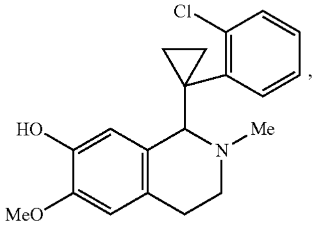

BTS-73-947

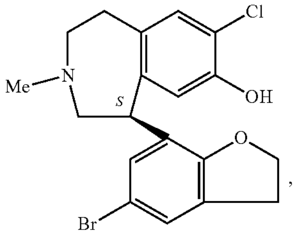

NNC-22-0010

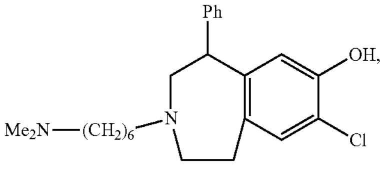

JHS 271

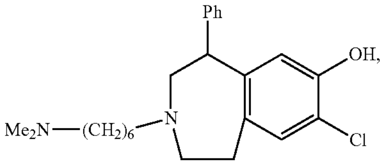

JHS 198

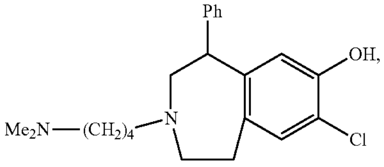

JHS 136

-continued

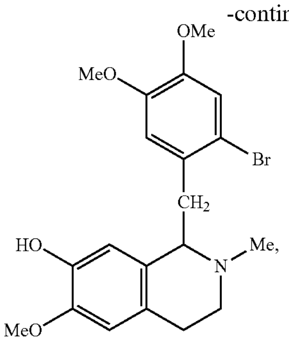

A 69024

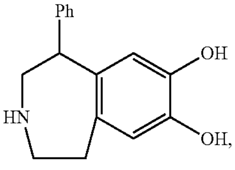

SKF 58611A

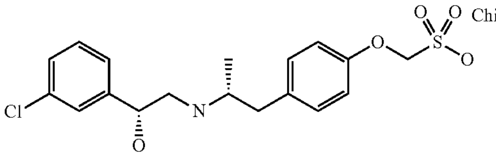

Chiral, and

BMS 196085

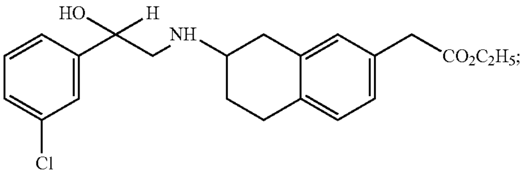

SR 58611A or a pharmaceutically acceptable salt, solvate, hydrate, prodrug, structural analog, metabolite, or polymorph of any of the foregoing, or a pharmaceutically acceptable salt of any of the foregoing.

2. The pharmaceutical dosage form of aspect 1, wherein the API is selected from one or more of those in Table I or a pharmaceutically acceptable salt, solvate, hydrate, prodrug, structural analog, metabolite, or polymorph of any of the foregoing, or a pharmaceutically acceptable salt of any of the foregoing.

3. The pharmaceutical dosage form of aspect 1, wherein the API comprises 6,7,7a,8,9,13b-hexahydro-2-hydroxy-3-methoxy-7-methyl-5H-benzo[d]naphtho[2,1-b]azepine;

6,7,7a,8,9,13b-hexahydro-2-hydroxy-7-methyl-5H-benzo[d]naphtho[2,1-b]azepine;

6,7,7a,8,9,13b-hexahydro-3-chloro-2-hydroxy-7-methyl-5H-benzo[d]naphtho[2,1-b]azepine;

6,7,7a,8,9,13b-hexahydro-2-hydroxy-3,7-dimethyl-5H-benzo[d]naphtho[2,1-b]azepine;

6,7,7a,8,9,13b-hexahydro-2-amino-7-methyl-5H-benzo[d]naphtho[2,1-b]azepine;

6,7,7a,8,9,13b-hexahydro-2-amino-3-chloro-7-methyl-5H-benzo[d]naphtho[2,1-b]azepine;

6,7,7a,8,9,13b-hexahydro-2-amino-3,7-dimethyl-5H-benzo[d]naphtho[2,1-b]azepine;

6,6a, 7,8,9,13b-hexahydro-12-methoxy-7-methyl[1]benzopyrano[4,3-a][3]benzazepine;

6,6a, 7,8,9,13b-hexahydro-7-methyl[1]benzopyrano[4,3-a][3]benzazepin-12-ol;

6,6a, 7,8,9,13b-hexahydro-3-hydroxy-2-methoxy-7-methyl-5H-benzo[d]naphtho[2,1-b]azepine;

2-hydroxy-3-methoxy-7-methyl-5,6,7,7a,8,9,10,14b-octahydro-benzo[d]benzo[3,4] cyclo-hepta[1,2-b]azepine;

3-hydroxy-2-methoxy-7-methyl-5,6,7,7a,8,9,10,14b-octahydro-benzo[d]benzo[3,4] cyclo-hepta[1,2-b]azepine;

5,6,7,7a,8,12b-hexahydro-2-hydroxy-3-chloro-7-methyl-benz[d]indeno[2,1-b]azepine;

5,6,7,7a,8,12b-hexahydro-2-hydroxy-3-methoxy-7-methyl-benz[d]indeno[2,1-b]azepine;

5,6,7,7a,8,12b-hexahydro-2-amino-3-chloro-7-methyl-benz[d]indeno[2,1-b]azepine;

5,6,7,7a,8,12b-hexahydro-2-hydroxy-7-methyl-benz[d]indeno[2,1-b]azepine;

5,6,7,7a,8,12b-hexahydro-3,7-dimethyl-2-hydroxy-benz[d]indeno[2,1-b]azepine;

5,6,7,7a,8,12b-hexahydro-3-chloro-7-cyclopropylmethyl-2-hydroxy-benz[d]indeno[2,1b]azepine;

5,6,7,7a,8,12b-hexahydro-7-allyl-3-chloro-2-hydroxy-benz[d]indeno[2,1-b]azepine;

5,6,7,7a,8,12b-hexahydro-3-chloro-2-hydroxy-7,8,8-trimethyl-benz[d]indeno[2,1-b]azepine;

5,6,7,7a,8,11b-hexahydro-3-chloro-7-methylthieno[2',3':4,5]cyclopenta[1,2-a][3]benzazepine-2-ol;

5,6,7,7a,8,12b-hexahydro-2-hydroxy-3-chloro-benz[d]indeno[2,1-b]azepine;

6,7,7a,8,9,13b-hexahydro-3-chloro-2-hydroxy-5H-benzo[d]naphtho[2,1-b]azepine;

or 6,7,7a,8,9,13b-hexahydro-2-amino-3-trifluoromethyl-7-methyl-5H-benzo[d]naphtho[2,1b]azepine or a pharmaceutically acceptable salt, solvate, hydrate, prodrug, structural analog, metabolite, or polymorph of any of the foregoing, or a pharmaceutically acceptable salt of any of the foregoing.

4. The pharmaceutical dosage form of aspect 1, wherein the API is selected from one or more of:

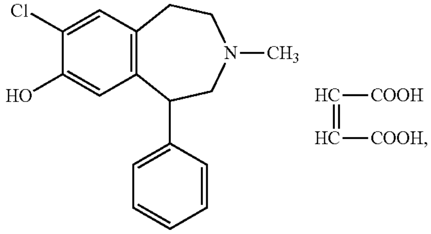

SCH 23390

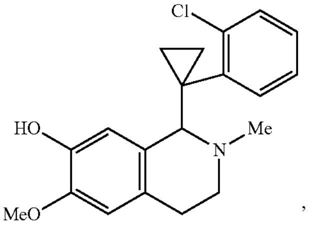

,

BTS-73-947

-continued

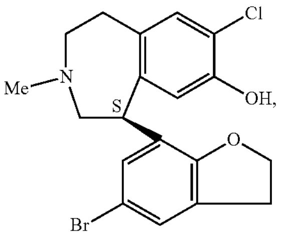

NNC-22-0010

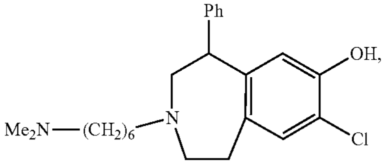

JHS 271

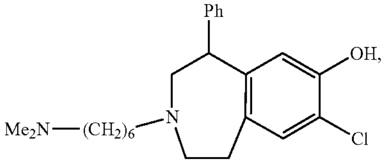

JHS 198

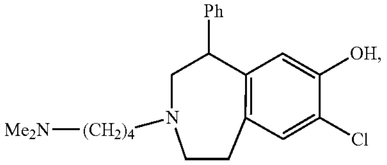

JHS 136

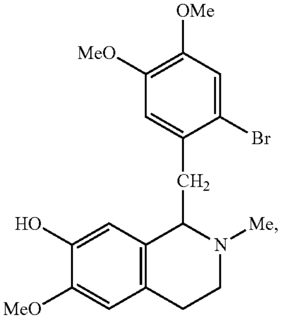

A 69024

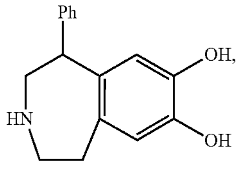

SKF 58611A

-continued

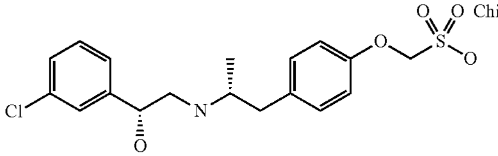

Chiral, and

BMS 196085

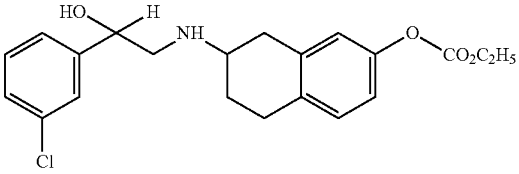

SR 58611A or a pharmaceutically acceptable salt, solvate, hydrate, prodrug, structural analog, metabolite, or polymorph of any of the foregoing, or a pharmaceutically acceptable salt of any of the foregoing.

5. The pharmaceutical dosage form of aspect 1, wherein the API comprises ecopipam or a pharmaceutically acceptable salt, solvate, hydrate, prodrug, structural analog, metabolite, or polymorph thereof, or a pharmaceutically acceptable salt thereof.

6. The pharmaceutical dosage form of any one of the preceding aspects, wherein the pharmaceutical dosage form is for pulmonary, transdermal, or transmucosal delivery.

7. The pharmaceutical dosage form of any one of the preceding aspects, wherein the pharmaceutical dosage form is for transmucosal delivery, (e.g., buccal and/or sublingual).

8. The pharmaceutical dosage form of any one of the preceding aspects, wherein the pharmaceutical dosage form is for delivery to the mucosal lining of the nasal, rectal, vaginal, ocular, or oral cavity.

9. The pharmaceutical dosage form of any one of the preceding aspects, wherein the pharmaceutical dosage form is for topical oral delivery.

10. The pharmaceutical dosage form of any one of the preceding aspects, wherein the pharmaceutical dosage form comprises a bioadhesive.

11. The pharmaceutical dosage form of any one of the preceding aspects, wherein the pharmaceutical dosage form comprises a mucoadhesive.

12. The pharmaceutical dosage form of any one of the preceding aspects, wherein the pharmaceutical dosage form comprises a buccoadhesive.

13. The pharmaceutical dosage form of any one of aspects 1-12, wherein the pharmaceutical dosage form comprises one or more compounds selected from AB block copolymers of oligo(methyl methacrylate) and PAA, acacia, and polyvinyl alcohol, anionic types, Carbopol e.g. 934P, cationic types, chitosan (e.g. free or cross-linked by an anionic polymer), copolymers of PAA and PEG monoethylether monomethacrylate, epoxy resins, Eudragit polymers (e.g. Eudragit L-100, an anionic copolymer based on methacrylic acid and methyl methacrylate), gelatin, gellan gum, glycol, guar gum, hyaluronic acid, hydrogels of poly(N N-dimethylaminoethyl methacrylate-co-methyl methacrylate) e.g., poly(DMA/MMA) cross-linked with DVB, hydrophilic pressure-sensitive adhesives (PSAs), hydroxyethyl cellulose, hydroxyethyl methacrylate, hydroxypropyl cellulose, hydroxypropyl methylcellulose, methylcellulose, a modified starch-polyacrylic acid mixture, monomeric alpha-cyanoacrylate, PAA complexed with PEGylated drug conjugate, pectin, poly(acrylic acid/divinyl benzene), polyacrylates, polymethacrylates, polycarbophil, polyethylene carboxymethyl cellulose, polymers with thiol groups, polymethyl vinyl ether-maleic anhydride, polystyrenes, polyurethanes, polyvinyl pyrrolidone, psyllium amberlite-200 resin, sodium alginate, sodium alginate, tamarind gum, thermally modified starch, tragacanth, and xanthan gum.

14. The pharmaceutical dosage form of any one of aspects 10-13 wherein the bioadhesive, mucoadheasive, or bucco adhesive comprises the API dispersed therein.

15. The pharmaceutical dosage form of any one of the preceding aspects, wherein the pharmaceutical dosage form is a dosage form selected from a chewing gum, a chewable lozenge, a chewable tablet, a film, a gel, a liquid, a lozenge, a microporous hollow fiber, a mouthwash, an oral lyophilizate, an oral strip, an oravescent, an orodispersible, a patch, a powder, a semisolid, a sprayable liquid, a tablet, a tape, and a wafer.

16. The pharmaceutical dosage form of any one of the preceding aspects, wherein the pharmaceutical dosage form is a tablet.

17. The pharmaceutical dosage form of any one of the preceding aspects, wherein the pharmaceutical dosage form is a fast-dissolving tablet.

18. The pharmaceutical dosage form of any one of the preceding aspects, wherein the pharmaceutical dosage form is a buccal tablet.

19. The pharmaceutical dosage form of any one of the preceding aspects, wherein the pharmaceutical dosage form is a nasal spray.

20. The pharmaceutical dosage form of any one of the preceding aspects, wherein the pharmaceutical dosage form is a matrix dosage form.

21. The pharmaceutical dosage form of any one of the preceding aspects, wherein the pharmaceutical dosage form is a unidirectional release dosage form.

22. The pharmaceutical dosage form of any one of the preceding aspects, wherein the pharmaceutical dosage form is a bilayer tablet.

23. The pharmaceutical dosage form of any one of the preceding aspects, wherein the pharmaceutical dosage form comprises a bioadhesive layer containing drug and a water impermeable coating.

24. The pharmaceutical dosage form of any one of the preceding aspects, wherein the pharmaceutical dosage form is a triple layer tablet.

25. The pharmaceutical dosage form of any one of the preceding aspects, wherein the pharmaceutical dosage form comprises a bioadhesive layer, a drug layer, and a water impermeable coating.

26. The pharmaceutical dosage form of any one of the preceding aspects, wherein the pharmaceutical dosage form comprises a microsphere containing the API.

27. The pharmaceutical dosage form of any one of the preceding aspects, wherein the microsphere comprises a mucoadhesive.

28. The pharmaceutical dosage form of any one of the preceding aspects, wherein a region of the pharmaceutical dosage form comprising the API comprises one or more materials selected from acrylic acid polymer, ethylcellulose, hydroxypropyl cellulose, methylcellulose, polyethylene oxide and polyvinyl pyrrolidone, poly(ethylacrylate methylmethacrylate), polyethyene glycol, and natural polymers including gaur-gum, pectins, starches, gelatin, and casein. The region can contain or be based on one or more excipients selected from lactose, glucose, sucrose, starch, crystalline cellulose, dextrin, cyclodextrin, silicic acid anhydride, aluminum silicate, talc, calcium stearate, magnesium stearate, beeswax, polyethylene glycol, and polyphosphate.

29. The pharmaceutical dosage form of any one of the preceding aspects, wherein the pharmaceutical dosage form further comprises one or more excipients.

30. The pharmaceutical dosage form of aspect 29, wherein the one or more excipients are selected from the groups of an absorption enhancer (also called permeation enhancer), an antioxidant, a binder, a carrier, a colorant, a diluent, a disintegrant, a flavor, a lubricant, a pH modifier, a plasticizer, a preservative, a sweetener, a taste masking agent, a taste modulating agent, and a viscosity modifier, including one or more from each group of excipients.

31. The pharmaceutical dosage form of any one of the preceding aspects, wherein the pharmaceutical dosage form comprises an absorption enhancer selected from one or more in the group of chelators (e.g., citric acid, EDTA, EGTA, methoxy salicylates, sodium salicylate); surfactants, including nonionic, e.g., polyoxyethylene vegetable-based fatty ethers derived from lauryl, cetyl, stearyl or oleyl alcohols (e.g., Brij), dodecylmaltoside, laureth-9, ethoxylated fatty acids (e.g. Myrj), poloxamer, polysorbate 80, span, sucrose esters, Tween, cationic (e.g., benzalkonium chloride, cetylmethylammonium bromide, Cetyl pyridinium chloride), and anionic (e.g., sodium dodecyl glycocholate, sodium lauryl sulfate, laureth-9 sodium dodecylsulfate); bile salts and other steroidal detergents (e.g., sodium glycocholate, sodium taurocholate, saponins, sodium taurodeoxycholate, sodium taurodihydrofusidate, and sodium glycodihydrofusidate); fatty acids (e.g., Oleic acid, Caprylic acid, Lauric acid, Lyso phosphatidyl choline, Phosphatidyl choline, sodium myristate); non-surfactants (e.g., 1-dodecylazacycloheptane-2-one (Azone), salicylates, and sulfoxides); enzymes (e.g., phopholipases, hyaluronidases, neuraminidase, and chondroitinase ABC); and Cyclodextrins (e.g., α, β, γ, Cyclodextrin, methylated β-cyclodextrins, hydroxypropyl beta-cyclodextrin), chitosan, trimethyl chitosan, poly-l-arginine, l-lysine, chondroitinase ABC, 1-dodecylazacycloheptan-2-one, and quillajasaponin.

32. The pharmaceutical dosage form of any one of the preceding aspects, wherein the API is microencapsulated.

33. The pharmaceutical dosage form of any one of the preceding aspects, wherein the API forms a complex with an ion exchange resin.

34. The pharmaceutical dosage form of any one of the preceding aspects, wherein the pharmaceutical dosage form is controlled release dosage form, optionally a sustained release, extended release, or prolonged release dosage form.

35. The pharmaceutical dosage form of any one of the preceding aspects, wherein the dosage form comprises an amount of API, e.g. ecopipam or a pharmaceutically acceptable salt thereof, about 1 wt % to about 40 wt %

36. The pharmaceutical dosage form of any one of the preceding aspects, wherein the dosage form comprises an amount of API, e.g. ecopipam or a pharmaceutically acceptable salt thereof, of about 1 mg to about 200 mg.

37. A method of administering a pharmaceutical dosage form of any one of the preceding aspects with a UGT inhibitor, or on a dosing schedule that overlaps a dosing schedule of a UGT inhibitor schedule.

38. A method of administering a pharmaceutical dosage form of any one of the preceding aspects with a CYP3A4 inducer, or on a dosing schedule that overlaps a dosing schedule of a CYP3A4 inducer schedule.

39. A method of administering a pharmaceutical dosage form of any one of aspects 37-38, wherein the dosage form comprises an amount of API, e.g. ecopipam or a pharmaceutically acceptable salt thereof, of about 1 mg to about 200 mg 40. A method of treating a subject in need of a dopamine D1 antagonist or a dopamine D1/D5 antagonist comprising administering to the subject a dosage form of any one of the preceding aspects 1-36 or according to a method of any one of aspects 37-39.

41. The method of aspect 40, wherein the subject has one or more disorders selected from the group of Tourette syndrome, transient tic disorder, chronic tic disorder, childhood onset fluency disorder (stuttering), Restless Legs Syndrome, refractory Restless Leg Syndrome, Restless Legs Syndrome with Augmentation, Augmentation associated with Restless Legs Syndrome, or a speech disorder selected from one or more of expressive language disorder, mixed receptive-expressive language disorder, phonological disorder and communication disorder not-otherwise-specified.

42. The method of aspect 41, wherein the subject has Tourette syndrome.

43. The method of aspect 41, wherein the subject has one or more disorders selected from the group of childhood onset fluency disorder (stuttering).

44. The method of aspect 41, wherein the subject has one or more disorders selected from the group of Restless Legs Syndrome, refractory Restless Leg Syndrome, Restless Legs Syndrome with Augmentation, or Augmentation associated with Restless Legs Syndrome.

What is claimed is:

1. A pharmaceutical dosage form for intra-oral absorption of ecopipam, comprising ecopipam or a pharmaceutically acceptable salt thereof and a pH modifier, the pH modifier being present in amount such that the pharmaceutical dosage form has a pH of about 2 to about 4, wherein when the dosage form is in solid form, the pH is as measured after dissolving the dosage form in 30 g of artificial saliva having a pH of 6.72, wherein the pH modifier comprises one or more of citric acid, hydrochloric acid, ascorbic acid, and acetic acid or a salt thereof.

2. The pharmaceutical dosage form of claim 1, comprising ecopipam HCl.

3. The pharmaceutical dosage form of claim 1, wherein the pharmaceutical dosage form comprises about 0.01 to about 0.8 wt % pH modifier based on the total weight of the formulation.

4. The pharmaceutical dosage form of claim 1, wherein the pharmaceutical dosage form has a pH of about 2 to about 3.5.

5. The pharmaceutical dosage form of claim 1, wherein the pharmaceutical dosage form is a tablet, powder, sachet, film, gel, gum, aerosol, oral lyophilizate, oravescent, sprayable liquid, wafer, mouthwash, or lozenge.

6. The pharmaceutical dosage form of claim 5, wherein the tablet is an orally dissolvable tablet, a fast-dissolving tablet, a buccal tablet, or a sublingual tablet, or wherein the film is a bioadhesive film, mucoadhesive film, or bucco adhesive film.

7. The pharmaceutical dosage form of claim 1, wherein the pharmaceutical dosage form comprise one or more excipients selected from the group an absorption enhancer (also called permeation enhancer), an antioxidant, a binder, a carrier, a colorant, a diluent, a disintegrant, a flavor, a lubricant, a pH modifier, a plasticizer, a preservative, a sweetener, a taste masking agent, a taste modulating agent, a viscosity modifier, a lyophilization agent, and nitrosamine scavengers, and including one or more from each group of excipients.

8. The pharmaceutical dosage form of claim 1, wherein the pharmaceutical dosage form comprises an absorption enhancer selected from one or more in the group of chelators; nonionic surfactants; cationic surfactants; anionic surfactants; fatty acids; non-surfactants; enzymes, chitosan, trimethyl chitosan, poly-l-arginine, l-lysine, chondroitinase ABC, 1-dodecylazacycloheptan-2-one, and quillajasaponin.

9. The pharmaceutical dosage form of claim 1, wherein upon administration, the pharmaceutical dosage form reduces a pH of saliva of a subject by at least 1 pH unit.

10. The pharmaceutical dosage form of claim 1, wherein upon administration, the pharmaceutical dosage form reduces a pH of saliva of a subject to 6.5 or less, 6 or less, 5.5 or less, 5 or less, 4.5 or less, or 4 or less.

11. The pharmaceutical dosage form of claim 1, wherein the pharmaceutical dosage form comprises one or more compounds selected from AB block copolymers of oligo (methyl methacrylate) and PAA, acacia, and polyvinyl alcohol, anionic types, Carbopol e.g. 934P, cationic types, chitosan, copolymers of PAA and PEG monoethylether monomethacrylate, epoxy resins, Eudragit polymers, gelatin, gellan gum, glycol, guar gum, hyaluronic acid, hydrogels of poly(N N-dimethylaminoethyl methacrylate-co-methyl methacrylate), hydrophilic pressure-sensitive adhesives (PSAs), hydroxyethyl cellulose, hydroxyethyl methacrylate, hydroxypropyl cellulose, hydroxypropyl methylcellulose, methylcellulose, a modified starch-polyacrylic acid mixture, monomeric alpha-cyanoacrylate, PAA complexed with PEGylated drug conjugate, pectin, poly (acrylic acid/divinyl benzene), polyacrylates, polymethacrylates, polycarbophil, polyethylene carboxymethyl cellulose, polymers with thiol groups, polymethyl vinyl ether-maleic anhydride, polystyrenes, polyurethanes, polyvinyl pyrrolidone, psyllium amberlite-200 resin, sodium alginate, sodium alginate, tamarind gum, thermally modified starch, tragacanth, and xanthan gum.

12. The pharmaceutical dosage form of claim 1, wherein the pharmaceutical dosage form comprises an amount of ecopipam or a pharmaceutically acceptable salt thereof, of about 1 wt % to about 40 wt % based on the total weight of the pharmaceutical dosage form.

13. The pharmaceutical dosage form of claim 1, wherein the pharmaceutical dosage form comprises an amount of ecopipam or a pharmaceutically acceptable salt thereof, of about 1 mg to about 200 mg.

14. A method of improving a safety profile of ecopipam, comprising administering to a subject in need thereof the pharmaceutical dosage form of claim 1, wherein the ecopipam is intraorally absorbed, wherein the safety profile is improved as compared to an oral dosage form of ecopipam or pharmaceutically acceptable salt in which ecopipam is absorbed in the GI tract.

15. The method of claim 14, wherein the improved safety profile is improved cardiac safety.

16. The method of claim 15, wherein administering the pharmaceutical dosage form reduces risk of QT prolongation.

17. A method of reducing one or more first pass metabolite concentrations in plasma when administering to a subject in need thereof the pharmaceutical dosage form of claim 1 for intraoral absorption of the ecopipam, wherein the one or more first pass metabolite concentrations are reduced after administration of the pharmaceutical dosage from as compared to after administration of an oral dosage form of ecopipam or pharmaceutically acceptable salt in which ecopipam is absorbed in the GI tract.

18. The method of claim 17, wherein the one or more first pass metabolites comprises ecopipam glucuronide.

19. The method of claim 18, wherein a concentration of ecopipam glucuronide is reduced by 75% to 85% after administration of the pharmaceutical dosage form as compared to a concentration of ecopipam glucuronide after administration of the oral dosage form.

20. The method of claim 17, wherein the first pass metabolites comprise EBS-101-40853 and/or EBS-101-40853 glucuronide.

21. The method of claim 20, wherein a concentration of EBS-101-40853 is reduced by 48% to 55% after administration of the pharmaceutical dosage form as compared to a concentration of EBS-101-40853 after administration of the oral dosage form and/or wherein a concentration of EBS-101-40853 glucuronide is reduced by 60% to 76% after administration of the pharmaceutical dosage form as compared to a concentration of EBS-101-40853 glucuronide after administration of the oral dosage form.

22. A method of administering a pharmaceutical dosage form of claim 1 to a subject in need thereof with a UGT inhibitor, or on a dosing schedule that overlaps a dosing schedule of a UGT inhibitor schedule.

23. A method of administering a pharmaceutical dosage form of claim 1 to a subject in need thereof with a CYP3A4 inducers, or on a dosing schedule that overlaps a dosing schedule of a CYP3A4 inducer schedule.

24. The method of claim 14, wherein the subject in has one or more disorders selected from the group of Tourette syndrome, transient tic disorder, chronic tic disorder, childhood onset fluency disorder (stuttering), Restless Legs Syndrome, refractory Restless Leg Syndrome, Restless Legs Syndrome with Augmentation, Augmentation associated with Restless Legs Syndrome, or a speech disorder selected from one or more of expressive language disorder, mixed receptive-expressive language disorder, phonological disorder and communication disorder not-otherwise-specified.

25. The method of claim 24, wherein the subject has Tourette syndrome.

26. The method of claim 24, wherein the subject has one or more disorders selected from the group of childhood onset fluency disorder (stuttering).

27. The method of claim 24, wherein the subject has one or more disorders selected from the group of Restless Legs Syndrome, refractory Restless Leg Syndrome, Restless Legs Syndrome with Augmentation, or Augmentation associated with Restless Legs Syndrome.

28. The method of claim 14, comprising administering the pharmaceutical dosage form to achieve a total daily dose of less than 2 mg/kg, 1.5 mg/kg or less, 1 mg/kg or less, or 0.5 mg/kg or less.

29. The method of claim 14, comprising administering the pharmaceutical dosage form to achieve a total daily dose of at least 25% less, or at least 50% less, or at least 75% less than a total daily dose needed for an oral dosage form which provides for absorption of ecopipam in the GI tract.

30. A method of treating of treating a disorder comprising administering to a subject in need thereof the pharmaceutical dosage form of claim 1, wherein the subject has one or more disorders selected from the group of Tourette syndrome, transient tic disorder, chronic tic disorder, childhood onset fluency disorder (stuttering), Restless Legs Syndrome, refractory Restless Leg Syndrome, Restless Legs Syndrome with Augmentation, Augmentation associated with Restless Legs Syndrome.

* * * * *